(12) United States Patent
Jiang et al.

(10) Patent No.: US 11,342,047 B2
(45) Date of Patent: May 24, 2022

(54) USING CELL-FREE DNA FRAGMENT SIZE TO DETECT TUMOR-ASSOCIATED VARIANT

(71) Applicant: Illumina, Inc., San Diego, CA (US)

(72) Inventors: Tingting Jiang, San Diego, CA (US); Chen Zhao, San Diego, CA (US); Han-Yu Chuang, San Diego, CA (US)

(73) Assignee: Illumina, Inc., San Diego, CA (US)

(*) Notice: Subject to any disclaimer, the term of this patent is extended or adjusted under 35 U.S.C. 154(b) by 1071 days.

(21) Appl. No.: 15/957,622

(22) Filed: Apr. 19, 2018

(65) Prior Publication Data

US 2018/0307796 A1 Oct. 25, 2018

Related U.S. Application Data

(60) Provisional application No. 62/488,549, filed on Apr. 21, 2017.

(51) Int. Cl.

| G01N 33/48 | (2006.01) |
|---|---|
| G01N 33/50 | (2006.01) |
| G16B 20/20 | (2019.01) |
| G06N 3/04 | (2006.01) |
| G06N 3/12 | (2006.01) |
| G16B 40/00 | (2019.01) |
| G16B 20/00 | (2019.01) |
| G16B 30/00 | (2019.01) |
| G16B 30/10 | (2019.01) |
| G16B 35/00 | (2019.01) |
| G16C 20/60 | (2019.01) |

(52) U.S. Cl.
CPC ........... *G16B 20/20* (2019.02); *G06N 3/0472* (2013.01); *G06N 3/126* (2013.01); *G16B 20/00* (2019.02); *G16B 30/00* (2019.02); *G16B 30/10* (2019.02); *G16B 40/00* (2019.02); *G16B 35/00* (2019.02); *G16C 20/60* (2019.02)

(58) Field of Classification Search
CPC ........ G16B 30/00; G16B 40/00; G16B 20/00; G06N 3/0472; G06N 3/126
See application file for complete search history.

(56) References Cited

U.S. PATENT DOCUMENTS

| 7,601,499 | B2 | 10/2009 | Berka et al. |
|---|---|---|---|
| 8,620,593 | B2 | 12/2013 | Lo et al. |
| 10,095,831 | B2 | 10/2018 | Duenwald et al. |
| 11,072,814 | B2 | 7/2021 | Chudova et al. |
| 2011/0319272 | A1 | 12/2011 | Fan et al. |
| 2012/0053063 | A1 | 3/2012 | Rigatti et al. |
| 2013/0237431 | A1 | 9/2013 | Lo et al. |
| 2013/0310260 | A1 | 11/2013 | Kim et al. |
| 2014/0038830 | A1 | 2/2014 | Srinivasan et al. |
| 2014/0051154 | A1 | 2/2014 | Hyland et al. |
| 2014/0100121 | A1 | 4/2014 | Lo et al. |
| 2014/0180594 | A1 | 6/2014 | Kim et al. |
| 2014/0371078 | A1 | 12/2014 | Abdueva |
| 2015/0126379 | A1 | 5/2015 | Liang et al. |
| 2016/0019338 | A1 | 1/2016 | Chudova et al. |
| 2016/0201142 | A1 | 7/2016 | Lo et al. |
| 2017/0220735 | A1 | 8/2017 | Duenwald et al. |
| 2017/0362638 | A1 | 12/2017 | Chudova et al. |
| 2019/0065676 | A1 | 2/2019 | Duenwald et al. |

FOREIGN PATENT DOCUMENTS

| CA | 2878246 | 1/2014 |
|---|---|---|
| CA | 2922005 | 4/2014 |
| CN | 103201744 A | 7/2013 |
| EP | 2 772 549 A1 | 9/2014 |
| EP | 3 202 915 A1 | 8/2017 |
| TW | I661049 B | 6/2019 |
| WO | WO 2009/051842 A2 | 4/2009 |
| WO | WO 2013/000100 A1 | 1/2013 |
| WO | WO 2013/015793 A1 | 1/2013 |
| WO | WO 2013/052913 A2 | 4/2013 |
| WO | WO 2013/097062 A1 | 7/2013 |
| WO | WO 2013/109981 A1 | 7/2013 |
| WO | WO 2014/014498 A1 | 1/2014 |
| WO | WO 2014/015319 A1 | 1/2014 |
| WO | WO 2014/039556 A1 | 3/2014 |
| WO | WO 2014/149134 A2 | 9/2014 |
| WO | WO 2015/061359 A1 | 4/2015 |
| WO | WO 2015/184404 A1 | 12/2015 |
| WO | WO 2016/094853 A1 | 6/2016 |
| WO | WO 2017/136059 A1 | 8/2017 |

OTHER PUBLICATIONS

English machine translation of WO 2013/097062. (Year: 2021).*
Notice of Allowance dated Mar. 17, 2021 issued in U.S. Appl. No. 15/534,449.
Chinese Second Office Action [Translation Only] dated Mar. 2, 2021 issued in Application No. CN 20158075794.0.
Saudi Arabian First Office Action dated Feb. 17, 2021 issued in Application No. SA 518392138.
U.S. Appl. No. 17/350,768, filed Jun. 17, 2021, Chudova et al.
Office Action dated May 30, 2017 issued in U.S. Appl. No. 15/382,508.
Office Action dated Jan. 22, 2018 issued in U.S. Appl. No. 15/382,508.
Notice of Allowance dated Aug. 27, 2018 issued in U.S. Appl. No. 15/382,508.
International Search Report and Written Opinon dated Jun. 27, 2018 issued in Application No. PCT/US2018/028654.
International Search Report and Written Opinion dated Mar. 8, 2016 issued in Application No. PCT/US2015/065362.

(Continued)

*Primary Examiner* — Russell S Negin
(74) *Attorney, Agent, or Firm* — Weaver Austin Villeneuve & Sampson LLP

(57) ABSTRACT

Methods and systems are provided for determining a variant of interest by analyzing sizes and sequences of cfDNA fragments obtained from a test sample. The methods and systems provided herein implement processes that synergistically combine size and sequence information, thereby improving specificity and sensitivity of assays over conventional methods.

34 Claims, 20 Drawing Sheets

(56) References Cited

OTHER PUBLICATIONS

International Preliminary Report on Patentability dated Jun. 22, 2017 issued in Application No. PCT/US2015/065362.
Canadian Office Action and Examination Search Report dated Feb. 21, 2018 issued in Application No. CA 2,970,501.
European Examination Report dated Oct. 6, 2017 issued in Application No. EP 15819994.3-1404.
European Search Report dated Jun. 28, 2017 issued in Application No. EP 16205580.0-1404.
European First Office Action dated Jul. 21, 2017 issued in Application No. EP 16205580.0-1404.
European Second Office Action dated Apr. 5, 2018 issued in Application No. EP 16205580.0-1404.
International Search Report and Written Opinion dated Jul. 13, 2017 issued in Application No. PCT/US2016/067886.
Invitation to Pay Additional Fees and Partial International Search Report dated Apr. 26, 2017 issued in Application No. PCT/US2016/067886.
International Preliminary Report on Patentability dated Aug. 16, 2018 issued in Application No. PCT/US2016/067886.
Agostini, et al. "Circulating cell-free DNA: a promising marker of pathologic tumor response in rectal cancer patients receiving preoperative chemoradiotherapy," Ann. Surg. Oncol., Sep. 18, 2011, vol. 9, pp. 2461-2468. <DOI: 10.1245/s10434-011-1638-y>.
Allen, et al. "Persistent Aberrations in Circulating DNA Integrity after Radiotherapy Are Associated with Poor Prognosis in Nasopharyngeal Carcinoma Patients," Clin Cancer Res 2008; 14(13) Jul. 1, 2008. <DOI:10.1158/1078-0432.CCR-08-0182>.
Anderson, et al. [Abstract-Only] "Improved sensitivity of circulating tumor DNA measurement using short PCR amplicons," Clin Chim Acta. Jan. 15, 2015;439:97-101. <DOI:10.1016/j.cca.2014.10.011>.
Breitbach, et al. "Direct Quantification of Cell-Free, Circulating DNA from Unpurified Plasma," PLoS ONE, vol. 9, No. 3, Mar. 3, 2014, pp. 1-11.
Casadio, et al. "Urine cell-free DNA integrity as a marker for early bladder cancer diagnosis: preliminary data," Urol Oncol., Nov. 2013, vol. 31, No. 8, pp. 1744-1750, <DOI:10.1016/j.urolonc.2012.07.013>.
Casadio, et al. "Urine Cell-Free DNA Integrity as a Marker for Early Prostate Cancer Diagnosis: A Pilot Study," Hindawi Publishing Corp., BioMed Research International, vol. 2013, Jan. 2013, No. 270457, pp. 1-5.
Chaing, et al. "High Resolution mapping of copy-number alterations with massively parallel sequencing," Nature Methods, vol. 6, No. 1, Jan. 2009, pp. 99-103.
Chan, et al. "Size distributions of maternal and fetal DNA in maternal plasma," Clin Chem. Jan. 2004;50(1):88-92. <DOI:10.1373/clinchem.2003.024893>.
Diehl, et al. "Detection and quantification of mutations in the plasma of patients with colorectal tumors," PNAS—Nov. 8, 2005, vol. 102, No. 45 16368-16373. <DOI:10.1073/pnas.0507904102>.
Dobrzycka, et al. "Circulating free DNA, p53 antibody and mutations of KRAS gene in endometrial cancer," International Journal of Cancer, vol. 127, No. 3, Aug. 1, 2010, pp. 612-621.<DOI:10.1002/ijc.25077>.
Ellinger, et al. [Abstract-Only]"Apoptotic DNA fragments in serum of patients with muscle invasive bladder cancer: a prognostic entity," Cancer Lett. Jun. 18, 2008;264(2):274-80. <DOI:10.1016/j.canlet.2008.01.038>.
El-Shazly, et al. "Evaluation of serum DNA integrity as a screening and prognostic tool in patients with hepatitis C virus-related hepatocellular carcinoma," Int J Biol Markers. Apr.-Jun. 2010; 25(2): 79-86.
Fan, et al. "Analysis of the Size Distribution of Fetal and Maternal Cell-Free DNA by Paired-End Sequencing," Clinical Chemistry, 56:8 (2010) pp. 1-8.
Gang, et al. [Abstract-Only] "Prediction of Clear Cell Renal Cell Carcinoma by Integrity of Cell-Free DNA in Serum," Urology. Feb. 2010;75(2), pp. 262-265. <doi:10.1016/j.urology.2009.06.048>.

Gao, YJ., et al. [Abstract-Only] "Increased integrity of circulating cell-free DNA in plasma of patients with acute leukemia," Clin Chem Lab Med. Nov. 2010;48(11):1651-6. <DOI:10.1515/CCLM.2010.311. Epub Sep. 13, 2010>.
Giacona, et al. [Abstract-Only] "Cell-free DNA in human blood plasma: length measurements in patients with pancreatic cancer and healthy controls," Pancreas. Jul. 1998;17(1):89-97.
Hahn, et a. "Cell-Free DNA in Maternal Plasma: Has the Size-Distribution Puzzle Been Solved?" Clinical Chemistry, 56:8, (2010), pp. 1210-1211.
Hauser, et al. "Cell-free Circulating DNA: Diagnostic Value in Patients with Renal Cell Cancer," Anticancer Research, Jul. 2010, vol. 30, No. 7, pp. 2785-2789.
Holdenrieder, et al. [Abstract-Only] "DNA Integrity in Plasma and Serum of Patients with Malignant and Benign Diseases," Article first published online: Sep. 16, 2008. <DOI: 10.1196/annals.1448.013>.
Holdhoff, et al. "Analysis of Circulating Tumor DNA to Confirm Somatic KRAS Mutations," J Natl Cancer Inst., Sep. 16, 2009, vol. 101, No. 18, pp. 1284-1285. <DOI: 10.1093/jnci/djp240>.
Jiang, et al. "Increased plasma DNA integrity index in head and neck cancer patients," Int J Cancer, Dec. 1, 2006;119(11):2673-6.
Jiang, et al. "Lengthening and shortening of plasma DNA in hepatocellular carcinoma patients," PNAS, Feb. 2, 2015, pp. E1317-E1325.
Jiang, et al. "Noninvasive Fetal Trisomy (NIFTY) test: an advanced noninvasive prenatal diagnosis methodology for fetal autosomal and sex chromosomal aneuploidies," BMC Medical Genomics, vol. 5, No. 57, 2012, pp. 2-11.
Lun, et al. "Noninvasive prenatal diagnosis of monogenic diseases by digital size selection and relative mutation dosage on DNA in maternal plasma," Proc Natl Acad Sci USA. Dec. 16, 2008; 105(50): 19920-19925. <DOI:10.1073/pnas.0810373105>.
Mead, et al. "Circulating tumour markers can define patients with normal colons, benign polyps, and cancers," British Journal of Cancer, vol. 105, Jun. 28, 2011, pp. 239-245.
Milbury, et al. "Ice-Cold-PCR enables rapid amplification and robust enrichment for low-abundance unknown DNA mutations," Nucleic Acids Res. Jan. 2011; 39(1):e2. <DOI:10.1093/nar/gkq899>.
Mouliere, et al. "Circulating Cell-Free DNA from Colorectal Cancer Patients May Reveal High KRAS or BRAF Mutation Load," Translational Oncology, Jun. 2013, vol. 6, No. 3, pp. 319-328. <DOI 10.1593/tlo.12445>.
Mouliere, et al. "Circulating tumor-derived DNA is shorter than somatic DNA in plasma," PNAS, vol. 112, No. 11, Mar. 17, 2015, pp. 3178-3179.
Mouliere, et al. "High Fragmentation Characterizes Tumour-Derived Circulating DNA," PLoS ONE 6(9), e23418. <DQI:10.1371/journal.pone.0023418>.
Mouliere, et al. "Multi-marker analysis of circulating cell-free DNA toward personalized medicine for colorectal cancer," Molecular Oncology, Jul. 2014, vol. 8, No. 5, pp. 927-941. <DOI:10.1016/j.molonc.2014.02.005>.
Narayan, et al. "Ultrasensitive measurement of hotspot mutations in tumor DNA in blood using error-suppressed multiplexed deep sequencing," Cancer Res. Jul. 15, 2012; 72(14): 3492-3498. <DOI: 10.1158/0008-5472.CAN-11-4037>.
Pang, et al. "DNA studies using atomic force microscopy: capabilities for measurement of short DNA fragments," Front MolBioSci., Jan. 2015, vol. 2, No. 1, pp. 1-7. <DOI:10.3389/fmolb.2015.00001>.
Park, et al. "Quantitative analysis of cell-free DNA in the plasma of gastric cancer patients," Oncol. Lett., Apr. 1, 2012; 3(4), pp. 921-926. <DOI:10.3892/ol.2012.592>.
Payne, et al. "The presence of disseminated tumour cells in the bone marrow is inversely related to circulating free DNA in plasma in breast cancer dormancy," Br J Cancer. Jan. 17, 2012; 106(2), pp. 375-382. <doi: 10.1038/bjc.2011.537>.
Sai, et al. "Quantification of Plasma Cell-free DNA in Patients with Gastric Cancer," Anticancer Research 27: 2747-2752 (2007).
Salani, et al. "Measurement of Cyclin E Genomic Copy Number and Strand Length in Cell-Free DNA Distinguish Malignant versus

(56) References Cited

OTHER PUBLICATIONS

Benign Effusions," Imaging, Diagnosis, Prognosis, Clin. Cancer Res. 2007, vol. 13, No. 19, Oct. 1, 2017, pp. 5805-5809.
Schmidt, et al. "A Blood-based DNA Test for Colorectal Cancer Screening," Discovery Medicine, 7(37); Jul. 28, 2007, pp. 7-12.
Schmidt, et al. [Abstract-Only] "Integrity of Cell-Free Plasma DNA in Patients with Lung Cancer and Nonmalignant Lung Disease," Ann N Y Acad Sci. Aug. 2008;1137:207-13. <DOI:10.1196/annals. 1448.034>.
Shendure, et al. "Next-generation DNA sequencing," Nature Biotechnology, vol. 26, 2008, pp. 1135-1145.
Sikora, et al. "Detection of Increased Amounts of Cell-Free Fetal DNA with Short PCR Amplicons," Clinical Chemistry, Jan. 2010, vol. 56 No. 1, pp. 136-138. <DOI:10.1373/clinchem.2009.132951>.
Tsui, et al. "High Resolution Size Analysis of Fetal DNA in the Urine of Pregnant Women by Paired-End Massively Parallel Sequencing," PLoS One, vol. 7, No. 10, e48319. <doi:10.1371/journal.pone. 0048319>.
Umetani, et al. "Increased integrity of free circulating DNA in sera of patients with colorectal or periampullary cancer: direct quantitative PCR for ALU repeats," Clinical Chemistry Jun. 2006 vol. 52 No. 6 1062-1069. <DOI:10.1373/clinchem.2006.068577>.
Underhill, et al., "Fragment Length of Circulating Tumor DNA," PLoS Genetics, vol. 12, No. 7, Jul. 18, 2016, pp. 1-24.
Vu, et al. "Recovery of Small DNA Fragments from Serum Using Compaction Precipitation," PLoS One, vol. 7, No. 12, e51863. <DOI:10.1371/journal.pone.0051863>.
Wang, et al. "Human urine contains small, 150 to 250 nucleotide-sized, soluble DNA derived from the circulation and may be useful in the detection of colorectal cancer," Journal of Molecular Diagnostics, vol. 6, No. 2, May 2004:101-7. <DOI: 10.1016/S1525-1578(10)60497-7>.
Wang, et al. "Increased plasma DNA integrity in cancer patients," Cancer Res. Jul. 15, 2003;63(14):3966-8.
Xue, et al. "Optimizing the yield and utility of circulating cell-free DNA from plasma and serum," Clinica Chimica Acta 404 (2009) 100-104.
Yu, et al. "Recent Advances in Clinical Applications of Circulating Cell-free DNA Integrity," LabMedicine, (2014), vol. 45, pp. 6-12. <DOI:10.1309/LMKKOX6UJZQGW0EA>.
Yu, et al. "Size-based molecular diagnostics using plasma DNA for noninvasive prenatal testing," PNAS Early Edition, May 19, 2014, pp. 1-6.
Zaher, et al. "Cell-free DNA concentration and integrity as a screening tool for cancer," Indian J Cancer. Jul.-Sep. 2013, vol. 50, No. 3, pp. 175-183. <doi:10.4103/0019-509X.118721>.
Zhang, et al. "A novel real-time quantitative PCR method using attached universal template probe," Nucleic Acids Res. Oct. 15, 2003; 31(20): e123. <DOI:10.1093/nar/gng123>.
Australia First Office Action dated Jan. 8, 2019 issued in Application No. AU 2016391100.
Canadian First Office Action dated Feb. 28, 2019 issued in Application No. CA 3,013,572.
Chinese First Office Action dated Apr. 4, 2019 issued in Application No. CN 201680084307.1.
Eurasian First Office dated Jan. 30, 2019 issued in Application No. EA 201891580.
Extended European Search Report dated May 10, 2019 issued in Application No. EP 19161739.8.
Israel First Office Action dated Nov. 6, 2018 issued in Application No. IL 260938.
Israel Second Office Action dated Apr. 10, 2019 issued in Application No. IL 260938.
Singapore Notice of Eligibility for Grant dated Mar. 26, 2019 issued in Application No. SG 11201806595U.
Taiwanese First Office Action dated Nov. 30, 2018 issued in Application No. TW 105142299.
New Zealand First Examination Report dated Dec. 18, 2018 issued in Application No. NZ 745637.
U.S. Appl. No. 16/395,066, filed Apr. 25, 2019, Chudova et al.
Office Action dated Aug. 19, 2020 issued in U.S. Appl. No. 15/534,449.
Final Office Action dated Jan. 13, 2021 issued in U.S. Appl. No. 15/534,449.
International Preliminary Report on Patentability dated Oct. 31, 2019 issued in Application No. PCT/US2018/028654.
Argentina First Office Action dated Feb. 26, 2019 issued in Application No. AR 20160104015.
Australian Examination Report No. 1 dated Feb. 2, 2021 issued in Application No. AU 2019203491.
Canadian Second Office Action dated Jun. 30, 2019 issued in Application No. CA 3,013,572.
Canadian Third Office Action dated Nov. 9, 2020 issued in Application No. CA 3,013,572.
Chinese Second Office Action dated Sep. 26, 2019 issued in Application No. CN 201680084307.1.
Chinese Third Office Action dated May 22, 2020 issued in Application No. AU 2019203491.
Chinese Notice of Allowance [No Translation] dated Feb. 8, 2021 issued in Application No. CN 201680084307.1.
European First Office Action dated Dec. 23, 2020 issued in Application No. EP 19161739.8.
Israeli First Office Action dated Jul. 30, 2020 issued in Application No. IL 272710.
Thai First Office Action dated Nov. 25, 2020 issued in Application No. TH 1801004624.
Taiwanese First Office Action dated Apr. 6, 2020 issued in Application No. TW 108113871.
New Zealand First Examination Report dated May 20, 2020 issued in Application No. NZ 752319.
New Zealand Second Office Action dated Sep. 2, 2020 issued in Application No. NZ 752319.
Korean First Office Action dated Jun. 13, 2019 issued in Application No. KR 10-2018-7025212.
Korean First Office Action dated Feb. 19, 2020 issued in Application No. KR 10-2019-7034142.
European Extended Search Report dated Jul. 26, 2019 issued in Application No. EP 19164987.0.
Chinese First Office Action dated Aug. 7, 2020 issued in Application No. CN 201580075794.0.
Li, et al., ""A Survey of sequence alignment algorithms for next-generation sequencing"" Briefings in Bioinformatics, vol. 11 (2010) pp. 473-483.
Office Action dated Nov. 22, 2021 issued in U.S. Appl. No. 16/119,993.
Chinese Decision to Grant dated Aug. 13, 2021 issued in Application No. CN 20158075794.0.
Canadian Fourth Office Action dated Sep. 21, 2021 issued in Application No. CA 3,013,572.

\* cited by examiner

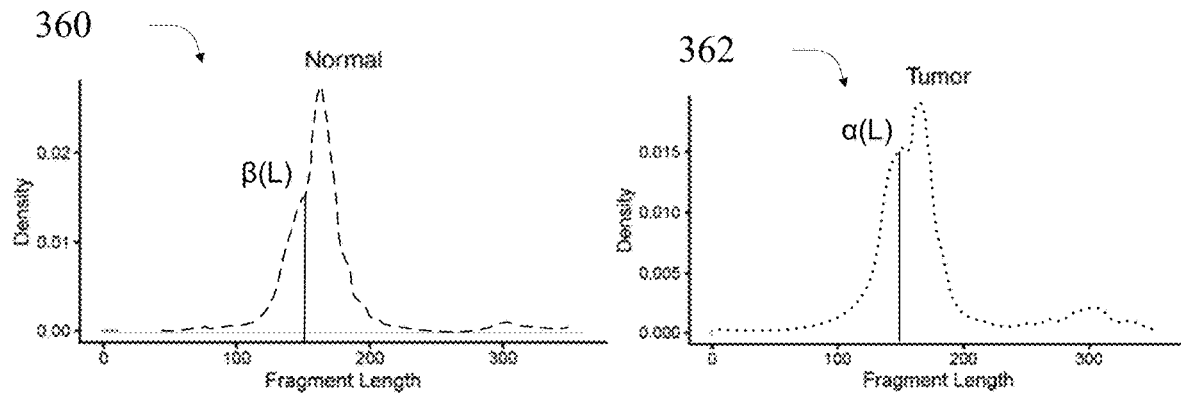

In a given bin L:

$$AF_{tumor} = AF_{plasma}/f_{tumor}$$

$$N_{mut}(L) \sim Binomial\,(DP * f_{tumor} * a(L), AF_{tumor})$$

$$AF(L) = \frac{N_{mut}(L)}{DP * [f_{tumor} * a(L) + (1 - f_{tumor}) * \beta(L)]}$$

With a sets of bins $L_{b1}, L_{b2} .. L_{bk}$:

$$N_{mut}(L_{b1,b2..bk}) \sim Binomial\left(\sum_{b1}^{bk} DP * f_{tumor} * a(L_{bi}), AF_{tumor}\right)$$

Bin selection Critieria:
1. Limit the probability (P1) that $N_{mut}(L_{b1,b2..bk})$ is below the LOD
2. Maximize the probability (P2) that $N_{mut}(L_{b1,b2..bk})$ is above the $AF_{plasma}$

Figure 3E

USING CELL-FREE DNA FRAGMENT SIZE TO DETECT TUMOR-ASSOCIATED VARIANT

CROSS REFERENCE TO RELATED APPLICATIONS

This application claims benefits under 35 U.S.C. § 119(e) to U.S. Provisional Patent Application No. 62/488,549, entitled: USING CELL-FREE DNA FRAGMENT SIZE TO DETECT TUMOR-ASSOCIATED VARIANT, filed Apr. 21, 2017, which is herein incorporated by reference in its entirety for all purposes.

BACKGROUND

The advent of technologies that allow for sequencing entire genomes in relatively short time, and the discovery of circulating cell-free DNA (cfDNA) have provided the opportunity to analyze genetic materials without the risks associated with invasive sampling methods.

Small quantities of circulating tumor DNA (ctDNA) originating from tumors, especially malignant tumors (or cancers), can be found among the cfDNA in the blood of cancer patients. The ctDNA may be identified by sequencing cfDNA to detect sequence variants that are known to be specifically associated with various types of tumors. Assays that interrogate ctDNA from blood in order to diagnose or stratify diseases are also known as liquid biopsies. Limitations of existing methods in liquid biopsies for diagnosing cancers include insufficient sensitivity stemming from the limited levels of ctDNA, and the sequencing bias of the technology stemming from the inherent nature of genomic information. These limitations underlie the continuing need for methods that would improve specificity, sensitivity, and applicability, to reliably analyze cancer related variants in a variety of clinical settings.

SUMMARY

The average lengths of ctDNA fragments are shorter than the cfDNA fragments from cells unaffected by cancers. Some implementations disclosed herein exploit this difference between unaffected cfDNA and ctDNA to detect the existence of cancer associated-variants (or calling the variants). This disclosure provides processes and systems for liquid biopsies that effectively combine size information with sequence information of cfDNA, thereby achieving high analytical sensitivity and specificity for calling tumor-associated variants and determining cancers. Because various methods and systems provided herein implement algorithms and processes that synergistically combine size and sequence information, the embodiments achieve analytical sensitivity and specificity that are improved over conventional methods using either sequence or size information alone, overcoming some of the limitations in liquid biopsies for diagnosing cancers.

One aspect of the disclosure relates to methods for determining a presence or a copy number of a genetic sequence variant associated with a tumor in a test sample by analyzing sizes and sequences of cfDNA fragments obtained from the test sample. In some implementations, the test sample may be peripheral blood, saliva, urine, and other biological fluid, as described below.

In some embodiments, the method is implemented at a computer system that includes one or more processors and system memory to determining a presence or a copy number of a genetic sequence variant associated with a tumor in a test sample, which includes cell free nucleic acid fragments that originate from tumor cells.

Some embodiments provide a method for detecting a simple nucleotide variant associated with tumor in a test sample including cell-free nucleic acid fragments. The method involves: (a) enriching cfDNA fragments having sequences corresponding to one or more selected genomic regions where simple nucleotide variants associated with tumors are located; (b) preparing a library from cfDNA fragments extracted from a sample, wherein the library preserves fragment lengths of the cfDNA fragments; (c) sequencing the cfDNA fragments to obtain sequences and sizes of the cfDNA fragments; and (d) producing a call that a tumor variant exists in the cfDNA fragments using the sequences and sizes of the cfDNA fragments.

In some implementations, the method involves: (a) retrieving, by the one or more processors, sequence reads and fragment sizes of cfDNA fragments obtained from a test sample; (b) assigning, by the one or more processors, the cfDNA fragments into a plurality of bins representing different fragment sizes; and (c) determining, using the sequence reads and by the one or more processors, an allele frequency of the variant of interest in a prioritized set of bins selected from the plurality of bins, wherein the prioritized set of bins was selected to (i) limit a probability that a quantity of the variant of interest in the prioritized set of bins is below a limit of detection and (ii) increase a probability that a quantity of the variant of interest in the prioritized set of bins is higher than in all bins of the plurality of bins.

In some implementations, the test sample is a plasma sample. In some implementations, the variant of interest is known or suspected to be associated with a cancer. In some implementations, the variant of interest is known or suspected to be associated with a genetic disorder.

In some implementations, the method further includes comparing the allele frequency of the variant of interest in the prioritized set of bins to a criterion, and making, based on the comparing, a call of the variant of interest in the test sample. In some implementations, the limit of detection of the method is about 0.05%-0.2%.

In some implementations, the prioritized set of bins was selected by a process including: providing a plurality of candidate sets, each candidate set including non-identical bins from the plurality of bins; for each candidate set, calculating a first probability that an allele frequency of the variant of interest in bins of the candidate set in a modeled sample is below a limit of detection, wherein the modeled sample includes both cfDNA originating from cells harboring the variant of interest and cfDNA originating from cells not harboring the variant of interest; for each candidate set, calculating a second probability that the allele frequency of the variant of interest in the bins of the candidate set in the modeled sample is above an allele frequency of the variant of interest in the plurality of bins in the modeled sample; and selecting a candidate set as the prioritized set based on the first probability and the second probability. Each candidate set including non-identical bins from the plurality of bins means that each candidate set has bins that are not identical to bins of other candidate sets.

In some implementations, the prioritized set has a largest value of the second probability among candidate sets whose values of the first probability do not exceed a criterion.

In some implementations, the plurality of candidate sets was obtained by a greedy process. In some implementations, the greedy process includes: obtaining sequence reads and fragment sizes of cfDNA fragments obtained from one or more unaffected training samples known to not be affected by a condition of interest and one or more affected training samples known to be affected by the condition of interest; assigning the cfDNA fragments obtained from the one or more unaffected training samples based on their sizes into the plurality of bins; assigning the cfDNA fragments obtained from the one or more affected training samples based on their sizes into the plurality of bins; ranking each bin of the plurality of bins based on a ratio of a frequency of fragments of the one or more affected training samples over a frequency of fragments of the one or more unaffected training samples; selecting a bin having the highest rank as a candidate set; adding a bin having a next highest rank to the last candidate set to provide a next candidate set; and repeating the last step until all bins of the plurality of bins are added, each repetition providing a candidate set.

In some implementations, the condition of interest includes one or more cancers. In some implementations, the condition of interest includes a cancer associated with the variant of interest. In some implementations, the affected training samples include cancer tissues and the unaffected training samples include non-cancer tissues.

In some implementations, the allele frequency of the variant of interest in the bins of the candidate set in the modeled sample is estimated as:

$$AF(L_{b1,b2\ldots bk}) = \frac{N_{mut}(L_{b1,b2\ldots bk})}{DP*[f_{tumor}*\Sigma_{b1}^{bk}\alpha(L_{bi}) + (1-f_{tumor})*\Sigma_{b1}^{bk}\beta(L_{bi})]}$$

wherein $AF(L_{b1,b2\ldots bk})$ is an allele frequency for bins $L_{b1}$, $L_{b2}\ldots L_{bk}$, $N_{mut}(L_{b1,b2\ldots bk})$ is a count of the variant of interest in bins $L_{b1}, L_{b2}\ldots L_{bk}$, DP is a sequencing depth, $f_{tumor}$ is a fraction of cfDNA from cells harboring the variant of interest, $\alpha(L_{bi})$ is a density of fragments in bin $L_{bi}$ in a fragment length distribution of one or more affected samples known to be affected by a condition of interest, and $\beta(L_{bi})$ is a density of fragments in bin $L_{bi}$ in a fragment length distribution of one or more unaffected samples known not to be affected by a condition of interest.

In some implementations, the cells harboring the variant of interest are cancer cells, and the modeled sample includes a plasma sample including cfDNA from cancer cells and cfDNA from non-cancer cells.

In some implementations, the count of the variant of interest in bins $L_{b1}, L_{b2}\ldots L_{bk}$ is modeled as a binomial distribution:

$$N_{mut}(L_{b1,b2\ldots bk}) \sim \text{Binomial}(\Sigma_{b1}^{bk}DP*f_{tumor}*\alpha(L_{bi}), AF_{tumor})$$

wherein $AF_{tumor}$ is the allele frequency of the variant of interest in the tissues harboring the variant of interest.

In some implementations, $AF_{tumor}$ is calculated as:

$$AF_{tumor} = AF_{plasma}/f_{tumor}$$

wherein $AF_{plasma}$ is the allele frequency of the variant of interest in the modeled sample.

In some implementations, the method further includes, after selecting the candidate set as the prioritized set, removing one or more bins that do not include a variant sequence of interest from the prioritized set.

In some implementations, the variant of interest includes a simple nucleotide variant (SNV). In some implementations, the SNV is a single nucleotide variant, a phased sequential variant, or a small indel.

In some implementations, the sequence reads are paired end reads, and the sizes of the cfDNA fragments are derived from read pairs.

In some implementations, the cfDNA fragments obtained from the sample have been enriched.

In some implementations, the method further includes, before (a), extracting the cfDNA fragments from the test sample.

In some implementations, the cfDNA fragments include circulating tumor DNA (ctDNA) fragments.

Another aspect of the disclosure provides a method of analyzing cell-free DNA (cfDNA) to determine a variant of interest, the method including: (a) obtaining sequence reads and fragment sizes of cfDNA fragments obtained from a test sample; (b) assigning the cfDNA fragments based on their sizes into a plurality of bins representing different fragment sizes; and (c) determining, using the sequence reads, an allele frequency of the variant of interest in a prioritized set of bins selected from the plurality of bins, wherein the prioritized set of bins are selected by a process including: (i) providing a plurality of candidate sets, each candidate set including non-identical bins from the plurality of bins; (ii) for each candidate set, calculating a second probability that an allele frequency of the variant of interest in bins of the candidate set in a modeled sample is above an allele frequency of the variant of interest in the plurality of bins in the modeled sample, wherein the modeled sample includes both tissues harboring the variant of interest and tissues harboring a wildtype sequence of the variant of interest; and (iii) selecting a candidate set having a largest value of the second probability.

In some implementations, the method further includes, before (iii) and for each candidate set, calculating a first probability that the allele frequency of the variant of interest in the bins of the candidate set in the modeled sample does not exceed a limit of detection, wherein (iii) includes selecting a candidate set having a largest value of the second probability among candidate sets whose values of the first probability do not exceed a criterion.

The disclosed embodiments also provide a computer program product including a non-transitory computer readable medium on which is provided program instructions for performing the recited operations and other computational operations described herein.

Some embodiments provide a system for evaluation of copy number of a nucleic acid sequence of interest in a test sample. The system includes a sequencer for receiving nucleic acids from the test sample providing nucleic acid sequence information from the sample, a processor; and one or more computer-readable storage media having stored thereon instructions for execution on the processor to evaluate copy number in the test sample using the method recited herein.

Although the examples herein concern humans and the language is primarily directed to human concerns, the concepts described herein are applicable to genomes from any plant or animal. These and other objects and features of the present disclosure will become more fully apparent from the following description and appended claims, or may be learned by the practice of the disclosure as set forth hereinafter.

INCORPORATION BY REFERENCE

All patents, patent applications, and other publications, including all sequences disclosed within these references, referred to herein are expressly incorporated herein by reference, to the same extent as if each individual publication, patent or patent application was specifically and individually indicated to be incorporated by reference. All documents cited are, in relevant part, incorporated herein by reference in their entireties for the purposes indicated by the context of their citation herein. However, the citation of any document is not to be construed as an admission that it is prior art with respect to the present disclosure.

BRIEF DESCRIPTION OF THE DRAWINGS

FIG. 3E shows a frequency length distribution of normal samples and frequency length distribution of tumor samples, and how probability data can be obtained from the distributions.

DETAILED DESCRIPTION

Definitions

Figure 1A:
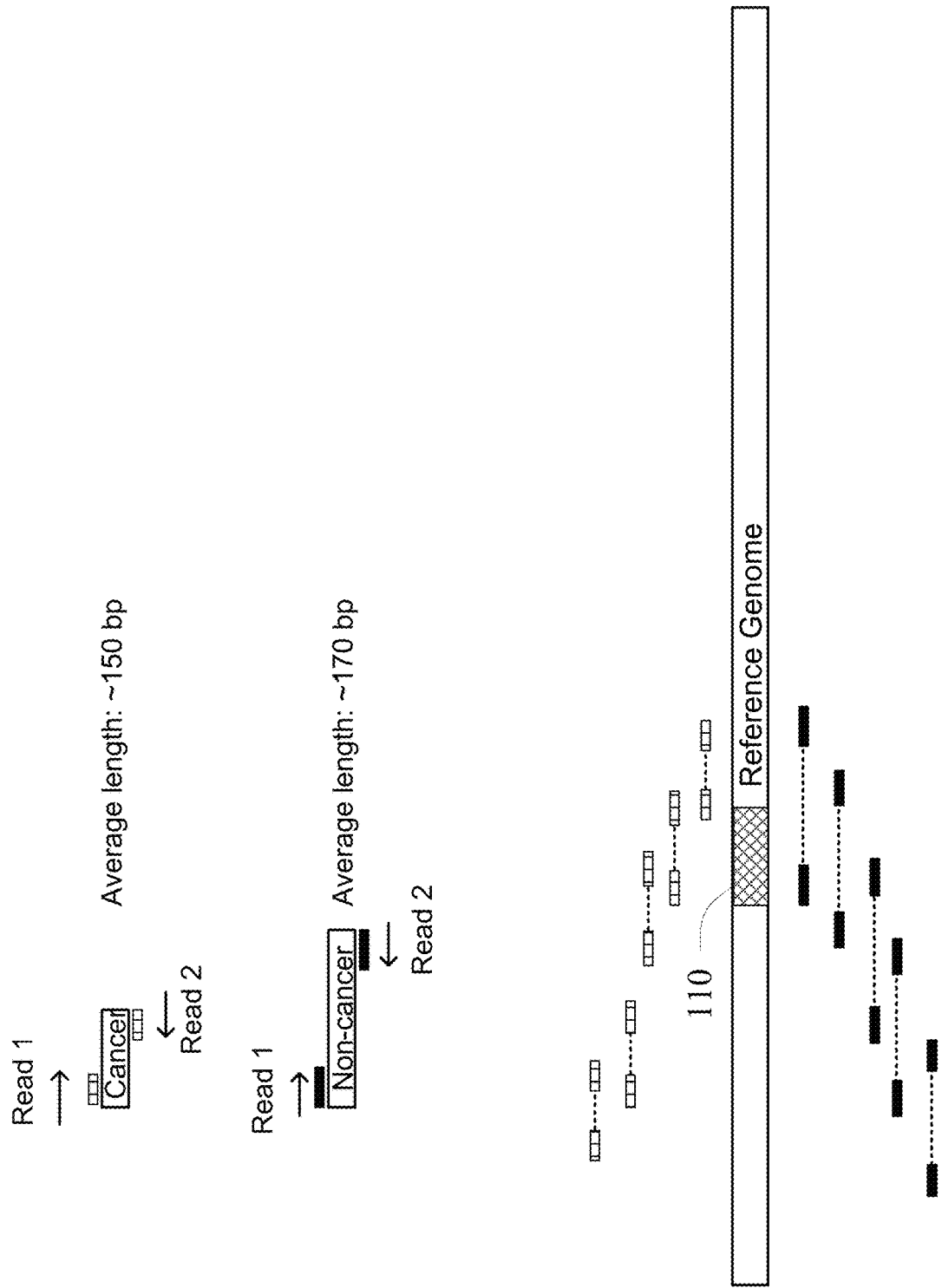
FIG. 1A thematically illustrates how paired end sequencing may be used to determine both fragment size and sequence.

Unless otherwise indicated, the practice of the method and system disclosed herein involves conventional techniques and apparatus commonly used in molecular biology, microbiology, protein purification, protein engineering, protein and DNA sequencing, and recombinant DNA fields, which are within the skill of the art. Such techniques and apparatus are known to those of skill in the art and are described in numerous texts and reference works (See e.g., Sambrook et al., "Molecular Cloning: A Laboratory Manual," Third Edition (Cold Spring Harbor), [2001]); and Ausubel et al., "Current Protocols in Molecular Biology" [1987]).

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the Specification as a whole. It is to be understood that this disclosure is not limited to the particular methodology, protocols, and reagents described, as these may vary, depending upon the context they are used by those of skill in the art. As used herein, the singular terms "a," "an," and "the" include the plural reference unless the context clearly indicates otherwise.

Unless otherwise indicated, nucleic acids are written left to right in 5' to 3' orientation and amino acid sequences are written left to right in amino to carboxy orientation, respectively.

A sequence of interest as used herein indicates a nucleic acid sequence in a genome of an organism such as a human. In some implementations, the sequence of interest is a gene, a SNP, an exon, a regulatory sequence of a gene, etc. In some implementations, the sequence of interest is a chromosome or a sub-chromosomal region.

A variant of interest is particular variant of a genetic sequence that is to be measured, qualified, quantified, or detected. In some implementations, a variant of interest is a variant known or suspected to be associated with a condition, such as a cancer, a tumor, or a genetic disorder.

A gene is a locus (or region) of DNA which is made up of nucleotides and is the molecular unit of heredity.

Genes can acquire mutations in their sequence, leading to different variants, known as alleles, in the population. These alleles encode slightly different versions of a protein, which cause different phenotype traits.

Allele frequency or gene frequency, is the frequency of an allele of a gene (or a variant of the gene) relative to other alleles of the gene, which can be expressed as a fraction or percentage. An allele frequency is often associated with a particular genomic locus, because a gene is often located at with one or more locus. However, an allele frequency as used herein can also be associated with a size-based bin of DNA fragments. In this sense, DNA fragments such as cfDNA containing an allele are assigned to different size-based bins. The frequency of the allele in a size-based bin relative to the frequency of other alleles is an allele frequency. In some implementations, the frequency of an allele or a variant is a proportion of reads supporting the variant calls out of all reads in multiple bins, such as a prioritized set of bins.

The term "parameter" herein refers to a numerical value that characterizes a property of a system such as a physical feature whose value or other characteristic has an impact on a relevant condition such as a sample or DNA fragments having a simple nucleotide variant or a copy number variant. In some cases, the term parameter is used with reference to a variable that affects the output of a mathematical relation or model, which variable may be an independent variable (i.e., an input to the model) or an intermediate variable based on one or more independent variables. Depending on the scope of a model, an output of one model may become an input of another model, thereby becoming a parameter to the other model.

The term "fragment size parameter" refers to a parameter that relates to the size or length of a fragment or a collection of fragments such nucleic acid fragments; e.g., a cfDNA fragments obtained from a bodily fluid. A fragment size or size range may be a characteristic of an aberrant genome or a portion thereof when the genome produces nucleic acid fragments having a higher concentration of the size or size range relative to nucleic acid fragments from another genome or another portion of the same genome. Various implementations disclosed herein provide methods to combine size information with sequence information to determine simple nucleotide variants. Additionally, the abundance of sequences can also be combined with size information to determine a structural variation or a copy number variation. Various implementations combine fragment size information and sequence information in innovative ways that are more efficient than simple additions or alternative selections of the two kinds of information, thereby providing improved performance over conventional assays for detecting cancer variants having low variant frequency.

"Simple Nucleotide Variants" or "SNVs" are genetic variants that differ from a reference sequence by one or more nucleotides in a relatively short genetic sequence. SNVs include single nucleotide variants, phased sequential variants and small insertions and deletions (indels). SNVs are distinct from structural variant and copy number variant in that structural variants include chromosomal structural rearrangements such as large indels, duplications, inversions, and transversions, and copy number variants include abnormal copy numbers of normally diploid regions of the genome. Some SNVs known to or suspected to be associated with tumors, also referred to as tumor SNVs, are targeted for analysis in various implementations.

The term "potentially variant-containing fragment" is used herein to refer to fragments that are identified as cfDNA fragments that are suspected of harboring a sequence mutation corresponding to a cancer variant. In various implementations, a cfDNA fragment is identified as a potentially variant-containing fragment when it is determined that the fragment provides a sequence read that includes a sequence of a known cancer variant and that the sequence read's genomic coordinate matches that of the cancer variant. Because sequencing and other processing sometimes introduces errors, there is uncertainty that a fragment sequence showing a cancer mutation actually corresponds to a fragment originating from a cancer cell. There is some chance that a cancer variant-containing sequence read from a fragment is in fact due to sequencing errors instead of an actual somatic mutation.

The term "copy number variation" or "CNV" herein refers to variation in the number of copies of a nucleic acid sequence present in a test sample in comparison with the copy number of the nucleic acid sequence present in a reference sample. In certain embodiments, the nucleic acid sequence is 1 kb or larger. In some cases, the nucleic acid sequence is a whole chromosome or significant portion thereof. A "copy number variant" refers to the sequence of nucleic acid in which copy-number differences are found by comparison of a nucleic acid sequence of interest in test sample with an expected level of the nucleic acid sequence of interest. For example, the level of the nucleic acid sequence of interest in the test sample is compared to that present in a qualified sample. Copy number variants/variations include deletions, including microdeletions, insertions, including microinsertions, duplications, multiplications, and translocations. CNVs encompass chromosomal aneuploidies and partial aneuploidies.

The term "aneuploidy" herein refers to an imbalance of genetic material caused by a loss or gain of a whole chromosome, or part of a chromosome.

The term "plurality" refers to more than one element. For example, the term is used herein in reference to a number of nucleic acid molecules or sequence tags that are sufficient to identify significant differences in SNVs or CNVs in test samples and qualified samples using the methods disclosed herein. In some embodiments, at least about $3\times10^6$ sequence tags of between about 20 and 40 bp are obtained for each test sample. In some embodiments, each test sample provides data for at least about $5\times10^6$, $8\times10^6$, $10\times10^6$, $15\times10^6$, $20\times10^6$, $30\times10^6$, $40\times10^6$, or $50\times10^6$ sequence tags, each sequence tag comprising between about 20 and 40 bp.

The term "paired end reads" refers to reads from paired end sequencing that obtains one read from each end of a nucleic acid fragment. Paired end sequencing may involve fragmenting strands of polynucleotides into short sequences called inserts. Fragmentation is optional or unnecessary for relatively short polynucleotides such as cell free DNA molecules.

The terms "polynucleotide," "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The nucleotides include sequences of any form of nucleic acid, including, but not limited to RNA and DNA molecules such as cfDNA molecules. The term "polynucleotide" includes, without limitation, single- and double-stranded polynucleotide.

The term "test sample" herein refers to a sample, typically derived from a biological fluid, cell, tissue, organ, or organism, comprising a nucleic acid or a mixture of nucleic acids comprising at least one nucleic acid sequence that is to be screened for SNVs or CNVs. In certain embodiments the sample comprises at least one nucleic acid sequence whose copy number is suspected of having undergone variation. Such samples include, but are not limited to sputum/oral fluid, amniotic fluid, blood, a blood fraction, or fine needle biopsy samples (e.g., surgical biopsy, fine needle biopsy, etc.), urine, peritoneal fluid, pleural fluid, and the like.

Although the sample is often taken from a human subject (e.g., patient), the assays can be used to SNVs or CNVs in samples from any mammal, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc. If such methods of pretreatment are employed with respect to the sample, such pretreatment methods are typically such that the nucleic acid(s) of interest remain in the test sample, sometimes at a concentration proportional to that in an untreated test sample (e.g., namely, a sample that is not subjected to any such pretreatment method(s)). Such "treated" or "processed" samples are still considered to be biological "test" samples with respect to the methods described herein.

The term "training set" herein refers to a set of training samples that can comprise affected and/or unaffected samples and are used to develop a model for analyzing test samples. In some embodiments, the training set includes unaffected samples. In these embodiments, thresholds for detecting SNV or CNV are established using training sets of samples that are unaffected for the SNV or CNV of interest. The unaffected samples in a training set may be used as the qualified samples to identify normalizing sequences, e.g., normalizing chromosomes, and the chromosome doses of unaffected samples are used to set the thresholds for each of the sequences, e.g., chromosomes, of interest. In some embodiments, the training set includes affected samples. The affected samples in a training set can be used to verify that affected test samples can be easily differentiated from unaffected samples.

A training set is also a statistical sample in a population of interest, which statistical sample is not to be confused with a biological sample. A statistical sample often comprises multiple individuals, data of which individuals are used to determine one or more quantitative values of interest generalizable to the population. The statistical sample is a subset of individuals in the population of interest. The individuals may be persons, animals, tissues, cells, other biological samples (i.e., a statistical sample may include multiple biological samples), and other individual entities providing data points for statistical analysis.

Usually, a training set is used in conjunction with a validation set. The term "validation set" is used to refer to a set of individuals in a statistical sample, data of which individuals are used to validate or evaluate the quantitative values of interest determined using a training set. In some embodiments, for instance, a training set provides data for calculating a mask for a reference sequence, while a validation set provides data to evaluate the validity or effectiveness of the mask.

The term "sequence of interest" or "nucleic acid sequence of interest" herein refers to a nucleic acid sequence that is associated with a difference in sequence representation between healthy and diseased individuals. A sequence of interest can be a sequence on a chromosome that is misrepresented, i.e., over- or under-represented, in a disease or genetic condition. A sequence of interest may be a portion of a chromosome, i.e., chromosome segment, or a whole chromosome. For example, a sequence of interest can be a chromosome that is over-represented in an aneuploidy condition, or a gene encoding a tumor-suppressor that is under-represented in a cancer. Sequences of interest include sequences that are over- or under-represented in the total population, or a subpopulation of cells of a subject. A "qualified sequence of interest" is a sequence of interest in a qualified sample. A "test sequence of interest" is a sequence of interest in a test sample.

The term "coverage" refers to the abundance of sequence tags mapped to a defined sequence. Coverage can be quantitatively indicated by sequence tag density (or count of sequence tags), sequence tag density ratio, normalized coverage amount, adjusted coverage values, etc.

The term "Next Generation Sequencing (NGS)" herein refers to sequencing methods that allow for massively parallel sequencing of clonally amplified molecules and of single nucleic acid molecules. Non-limiting examples of NGS include sequencing-by-synthesis using reversible dye terminators, and sequencing-by-ligation.

The terms "threshold value" and "qualified threshold value" herein refer to any number that is used as a cutoff to characterize a sample such as a test sample containing a nucleic acid from an organism suspected of having a medical condition. The threshold may be compared to a parameter value to determine whether a sample giving rise to such parameter value suggests that the organism has the medical condition. In certain embodiments, a qualified threshold value is calculated using a qualifying data set and serves as a limit of diagnosis of a SNV or CNV. If a threshold is exceeded by results obtained from methods disclosed herein, a subject can be diagnosed with a SNV or CNV. Appropriate threshold values for the methods described herein can be identified by analyzing normalized values (e.g. chromosome doses, NCVs or NSVs) calculated for a training set of samples. Threshold values can be identified using qualified (i.e., unaffected) samples in a training set which comprises both qualified (i.e., unaffected) samples and affected samples. The samples in the training set known to have chromosomal aneuploidies (i.e., the affected samples) can be used to confirm that the chosen thresholds are useful in differentiating affected from unaffected samples in a test set (see the Examples herein). The choice of a threshold is dependent on the level of confidence that the user wishes to have to make the classification. In some embodiments, the training set used to identify appropriate threshold values comprises at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 2000, at least 3000, at least 4000, or more qualified samples. It may be advantageous to use larger sets of qualified samples to improve the diagnostic utility of the threshold values.

The term "read" refers to a sequence obtained from a portion of a nucleic acid sample. Typically, though not necessarily, a read represents a short sequence of contiguous base pairs in the sample. The read may be represented symbolically by the base pair sequence (in A, T, C, or G) of the sample portion. It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

The term "genomic read" is used in reference to a read of any segments in the entire genome of an individual.

The term "sequence tag" is herein used interchangeably with the term "mapped sequence tag" to refer to a sequence read that has been specifically assigned, i.e., mapped, to a larger sequence, e.g., a reference genome, by alignment. Mapped sequence tags are uniquely mapped to a reference genome, i.e., they are assigned to a single location to the reference genome. Unless otherwise specified, tags that map to the same sequence on a reference sequence are counted once. Tags may be provided as data structures or other assemblages of data. In certain embodiments, a tag contains a read sequence and associated information for that read such as the location of the sequence in the genome, e.g., the position on a chromosome. In certain embodiments, the location is specified for a positive strand orientation. A tag may be defined to allow a limited amount of mismatch in aligning to a reference genome. In some embodiments, tags that can be mapped to more than one location on a reference genome, i.e., tags that do not map uniquely, may not be included in the analysis.

As used herein, the terms "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

Aligned reads or tags are one or more sequences that are identified as a match in terms of the order of their nucleic acid molecules to a known sequence from a reference genome. Alignment can be done manually, although it is typically implemented by a computer algorithm, as it would be impossible to align reads in a reasonable time period for implementing the methods disclosed herein. One example of an algorithm from aligning sequences is the Efficient Local Alignment of Nucleotide Data (ELAND) computer program distributed as part of the Illumina Genomics Analysis pipeline. Alternatively, a Bloom filter or similar set membership tester may be employed to align reads to reference genomes. See U.S. Patent Application No. 61/552,374 filed Oct. 27, 2011 which is incorporated herein by reference in its entirety. The matching of a sequence read in aligning can be a 100% sequence match or less than 100% (non-perfect match).

The term "mapping" used herein refers to specifically assigning a sequence read to a larger sequence, e.g., a reference genome, by alignment.

As used herein, the term "reference genome" or "reference sequence" refers to any particular known genome sequence, whether partial or complete, of any organism or virus which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences.

In various embodiments, the reference sequence is significantly larger than the reads that are aligned to it. For example, it may be at least about 100 times larger, or at least about 1000 times larger, or at least about 10,000 times larger, or at least about $10^5$ times larger, or at least about $10^6$ times larger, or at least about $10^7$ times larger.

In one example, the reference sequence is that of a full length human genome. Such sequences may be referred to as genomic reference sequences. In another example, the reference sequence is limited to a specific human chromosome such as chromosome 13. In some embodiments, a reference Y chromosome is the Y chromosome sequence from human genome version hg19. Such sequences may be referred to as chromosome reference sequences. Other examples of reference sequences include genomes of other species, as well as chromosomes, sub-chromosomal regions (such as strands), etc., of any species.

In various embodiments, the reference sequence is a consensus sequence or other combination derived from multiple individuals. However, in certain applications, the reference sequence may be taken from a particular individual.

The term "clinically-relevant sequence" herein refers to a nucleic acid sequence that is known or is suspected to be associated or implicated with a genetic or disease condition. Determining the absence or presence of a clinically-relevant sequence can be useful in determining a diagnosis or confirming a diagnosis of a medical condition, or providing a prognosis for the development of a disease.

The term "derived" when used in the context of a nucleic acid or a mixture of nucleic acids, herein refers to the means whereby the nucleic acid(s) are obtained from the source from which they originate. For example, in one embodiment, a mixture of nucleic acids that is derived from two different genomes means that the nucleic acids, e.g., cfDNA, were naturally released by cells through naturally occurring processes such as necrosis or apoptosis. In another embodiment, a mixture of nucleic acids that is derived from two different genomes means that the nucleic acids were extracted from two different types of cells from a subject.

The term "based on" when used in the context of obtaining a specific quantitative value, herein refers to using another quantity as input to calculate the specific quantitative value as an output.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

As used herein, the term "corresponding to" sometimes refers to a nucleic acid sequence, e.g., a gene or a chromosome, that is present in the genome of different subjects, and which does not necessarily have the same sequence in all genomes, but serves to provide the identity rather than the genetic information of a sequence of interest, e.g., a gene or chromosome.

As used herein the term "chromosome" refers to the heredity-bearing gene carrier of a living cell, which is derived from chromatin strands comprising DNA and protein components (especially histones). The conventional internationally recognized individual human genome chromosome numbering system is employed herein.

As used herein, the term "polynucleotide length" refers to the absolute number of nucleotides in a sequence or in a region of a reference genome. The term "chromosome length" refers to the known length of the chromosome given in base pairs, e.g., provided in the NCBI36/hg18 assembly of the human chromosome found at |genome|.|ucsc|.|edu|/cgi-bin/hgTracks?hgsid=167155613&chromInfoPage=on the World Wide Web.

The term "subject" herein refers to a human subject as well as a non-human subject such as a mammal, an invertebrate, a vertebrate, a fungus, a yeast, a bacterium, and a virus. Although the examples herein concern humans and the language is primarily directed to human concerns, the concepts disclosed herein are applicable to genomes from any plant or animal, and are useful in the fields of veterinary medicine, animal sciences, research laboratories and such.

The term "condition" herein refers to "medical condition" as a broad term that includes all diseases and disorders, but can include injuries and normal health situations, such as pregnancy, that might affect a person's health, benefit from medical assistance, or have implications for medical treatments.

The term "sensitivity" as used herein refers to the probability that a test result will be positive when the condition of interest is present. It may be calculated as the number of true positives divided by the sum of true positives and false negatives.

The term "specificity" as used herein refers to the probability that a test result will be negative when the condition of interest is absent. It may be calculated as the number of true negatives divided by the sum of true negatives and false positives.

The term "enrich" herein refers to the process of amplifying polymorphic target nucleic acids contained in a portion of a maternal sample, and combining the amplified product with the remainder of the maternal sample from which the portion was removed. For example, the remainder of the maternal sample can be the original maternal sample.

The term "primer," as used herein refers to an isolated oligonucleotide that is capable of acting as a point of initiation of synthesis when placed under conditions inductive to synthesis of an extension product (e.g., the conditions include nucleotides, an inducing agent such as DNA polymerase, and a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, use of the method, and the parameters used for primer design.

Introduction

Cancer genome sequencing studies have collectively identified various genetic mutations that make human tumors grow and progress. As a result of their findings, scientists have discovered that most cancers carried somatic DNA mutations. Unlike hereditary or germline mutations that are passed from parent to child, somatic mutations form in the DNA of individual cells during a person's life and are not passed from parent to child. Therefore, sequence variants due to somatic DNA mutations that are associated with cancers provide biomarkers to detect cancers and measure development of cancers.

Tumor tissues per se include large amount of DNA materials that may be analyzed to detect cancer variants, or sequence variants that are known to or suspected to be associated with various cancers. This can be performed through biopsy of tumor tissues. However, due to the continuously changing location and form of cancers, it is often difficult to continuously obtain biopsy samples at various locations to obtain cancer tissues and cancer originating DNA. Scientists have discovered that dying tumor cells release small pieces of their DNA into the bloodstream and other bodily fluids. These pieces are called cell free circulating tumor DNA (ctDNA), which coexists with cell-free DNA (cfDNA) from non-cancer cells. Methods are being developed for screening ctDNA related to somatic mutations as a way to detect and follow the progression of a patient's tumor. These methods are also referred to as liquid biopsy.

Various current liquid biopsy methods utilize high throughput sequencing to analyze cfDNA collected from patients. However, the ability to detect tumor-specific variants is bounded by several factors. Liquid biopsy methods utilizing high throughput sequencing are limited by sequencing error rate and sequencing depth. In some cancer patients, tumor load may be very load for some tumor variant. For instance, the ctDNA may be fewer than 0.1%, or 0.01% in some samples. So the fraction of cfDNA originating from tumors can fall below the margin of error of sequencing pipeline. Tumor-specific variants called from low tumor burden patients can be plagued by high false positive rates, because there is small but existing chance that a sequence matching the tumor variant in a putative read is in fact due to sequencing errors instead of an actual mutation. It is desirable to increase true positive to improve sensitivity and decrease false positive to improve selectivity.

Recent studies have observed that ctDNA fragments are generally shorter than cfDNA fragments originating from non-tumor cells. It has been observed that ctDNA fragments are on average about 20 bp shorter than background cfDNA (e.g., about 145 bp vs 165 bp). The distributions of ctDNA and cfDNA are broad and overlapping. However, these observations alone have not provided means to improving the performance of liquid biopsy assays. Presented below are methods that characterize insert size distribution of reads supporting variants. These methods utilize the difference in fragment size by applying specific processes and algorithms which synergistically and effectively combine fragment size and fragment abundance information to improve performance of variant calling using high throughput sequencing. Some implementations provide improved sensitivity and/or selectivity as compared to using either sequence or size information alone or in the alternatives.

In various applications, ctDNA assays require detection of mutant fragments at very low frequencies, 0.1-0.01% or even lower for screening applications. Distinguishing true positives from false positives (specificity) is challenging given errors from library preparation, clustering, and sequencing. By building assays that utilize cfDNA fragment size, we can increase the likelihood that a call of a cancer variant is correct. For example, if a potential somatic mutation is called in a fragment and the fragment is short, it's more likely to be a true tumor fragment than if the fragment was long. This type of weighting can be used to improve the specificity of the assay. Another way to exploit the fragment size difference is to only use or more heavily weight fragments that are shorter. This effectively enriches ctDNA information relative to non-tumor cfDNA.

Other potential benefits of using size information include: 1) reducing sequencing requirements, 2) estimating total tumor burden, and 3) distinguishing germline variants from true somatic variants, where germline variants have normal fragment lengths and somatic variants have shorter fragments.

The problem of analyzing tumor heterogeneity in metastatic cancer patients can be also be addressed using ctDNA measurements. Metastatic cancer patients have multiple tumors sometimes with different driver mutations. Since, these driver mutations are often the targets of drugs, it is highly desirable to identify and characterize the driver mutation(s) in a patient. Moreover, it would be valuable to know which drivers are coming from the same tumor and which are from different tumors. Further, there is evidence that when the driver mutation being targeted with a drug is present in the dominant clone within a tumor, the therapeutic response is better than when the driver mutation is from a minor clone. Conventional methods are ineffective for determining these measures of heterogeneity. It is not practical or safe to biopsy a patient for a large number of times to determine these measures. Moreover, a biopsy only samples a small part of one tumor. ctDNA in the blood is the superposition of ctDNA from all the tumors in the body.

Preliminary data using targeted sequencing in an example below show that the relative allele frequencies in the ctDNA data may represent different clones or tumors. Some implementation provided herein can determine tumor heterogeneity, mutations that are from the same clone, and which clone is likely to be the dominant one.

In certain embodiments, whole genome sequencing aids in determining tumor heterogeneity. The vast majority of solid tumors develop somatic copy number alterations greater than 10 Mb in size. These are detectable using whole genome sequencing, providing an orthogonal measure of ctDNA fraction. Different levels of copy number that are region specific could be used to determine tumor heterogeneity. Moreover, this measure of genome-wide copy number alterations and measure of tumor heterogeneity could be compared to the deeper targeted sequencing described above. When the focal somatic alterations measured using the targeted method are compared to the copy number changes, it will likely increase the ability to distinguish multiple clones.

This disclosure provides analytical methodology in liquid biopsy for deriving fragment size information from, e.g., paired-end reads, and using this information in an analysis pipeline. Improved analytical sensitivity provides the ability to apply liquid biopsy methods with improved selectivity. And by adjusting decision criterion, sensitivity may also be improved over conventional methods using sequence information alone.

Fragment Size of cfDNA

As mentioned above, fragment size parameters, as well as sequences and abundance in cfDNA, may be used to evaluate tumor variants. Fragment size of a cfDNA fragment may be obtained by pair end sequencing, electrophoresis (e.g., microchip-based capillary electrophoresis), and other methods known in the art. FIG. 1A thematically illustrates how paired end sequencing may be used to determine fragment size, fragment sequence, and sequence coverage.

Figure 1B:
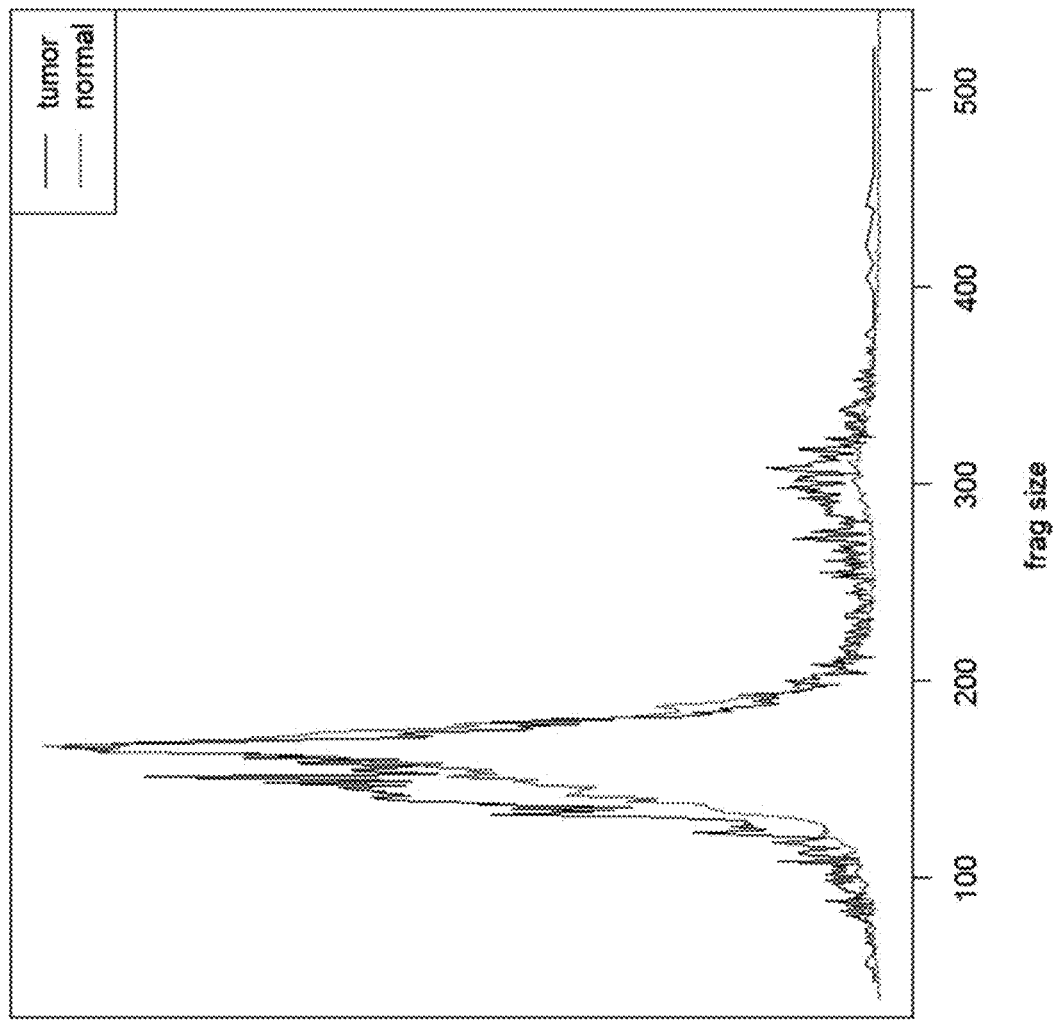
FIG. 1B shows a density plot of empirical data for fragment size from reads supporting a tumor variant (dark gray) and reads supporting non-tumor variants or a reference sequence (light gray).

The top half of FIG. 1A a shows a diagram of a ctDNA fragment and a non-cancer cfDNA fragment providing a template for a paired end sequencing process. Conventionally, long nucleic acid sequences are fragmented into shorter sequences to be read in a paired end sequencing process. Such fragments are also referred to as inserts. In some implementations, fragmenting is unnecessary for cell free DNA because they already exist in fragments mostly shorter than 300 base pairs. As schematically shown at the top of FIG. 1A, ctDNA fragments are shorter than background cfDNA. Some observations have seen about 20 bp differences, e.g., about 145 bp for ctDNA and 165 bp for non-cancer cfDNA. FIG. 1B shows a density plot of empirical data for fragment size from reads derived from a cancer or tumor variant (dark gray) and reads derived from non-cancer variants or a reference sequence (light gray). Here the cancer variant shows an enrichment of smaller fragment sizes.

In the applications of implementations disclosed herein, the precise and absolute sizes of the two sources of DNA are not as important as a relative difference between the two. In one hypothesis, the DNA fragment size relates to the different cell types associated with the cancer cells versus the normal cells. Non-cancer cfDNA in plasma may originate from blood cells, while cancer cfDNA in plasma may originate from epithelial cells. The nucleosome structure of blood cells can be different from that of epithelial cells. Such structural difference may cause the DNA to be cleaved into different sizes. In another hypothesis, the fragment size difference may result from interactions between cancer cells and nucleosomes.

A nucleosome is a basic unit of DNA packaging in eukaryotes, including a segment of DNA wound in sequence around a histone octamer consisting of 2 copies each of the core histones H2A, H2B, H3, and H4. The nucleosome core particle consists of approximately 147 base pairs of DNA wrapped in 1.67 left-handed superhelical turns around the histone octamer. Core particles are connected by up to about 80 bp of linker DNA. Technically, a nucleosome is defined as the core particle plus one of these linker regions; however the word is also sometimes used to refer to a nucleosome core. It is possible that apoptosis or other cellular mechanisms in cancer cells and non-cancer cells differentially disrupt the structure of nucleosomes. One skilled in the art understands that the underlying mechanisms of this size difference do not affect the utilities of this disclosure.

In paired end sequencing on certain platforms, such as the Illumina's sequencing by synthesis platform as described further hereinafter, adaptor sequences, index sequences, and/or prime sequences are ligated to the two ends of a fragment. A fragment is first read in one direction, providing read 1 from one end of the fragment. Then a second read starts from the opposite end of the fragment, providing the read 2 sequence. The correspondence between read 1 and read 2 can be identified by their coordinates in the flow cell. Then read 1 and read 2 are mapped to a reference sequence as a pair of tags that are near each other, as shown in the bottom half of FIG. 1A. In some embodiments, if the reads are long enough, the two reads can overlap in a middle portion of the insert. After the pair is aligned to the reference sequence, the relative distance between the two reads and the length of the fragment from which the reads are derived can be determined from the positions of the two reads. Because paired end reads provide twice as many base pairs as single end reads of the same read length, they help to improve alignment qualities, especially for sequences with many repeats or non-unique sequences. After paired end reads are aligned to the reference sequence, the number of reads aligned to a bin can be determined. The number as well as the lengths of inserts (e.g., cfDNA fragments) can also be determined for a bin. In some embodiments, if an insert straddles two bins, half of an insert may be attributed to each bin. In various embodiments, both sequence information and alignment location of an insert are used to determine whether an insert includes a variant of interest, e.g., a cancer-associated variant of a sequence of interest 110 in the reference genome. For instance, in some implementations, if a read of a cfDNA fragment includes the sequence of a tumor variant, and the sequence matches the cancer variant's genomic coordinates, the cfDNA is identified with determined as a potentially variant-containing fragment. The potentially variant-containing fragment's sequence and size are used in downstream processes to analyze the cfDNA fragments for determining the existence or abundance of the cancer variant in the sample.

Figure 1C:
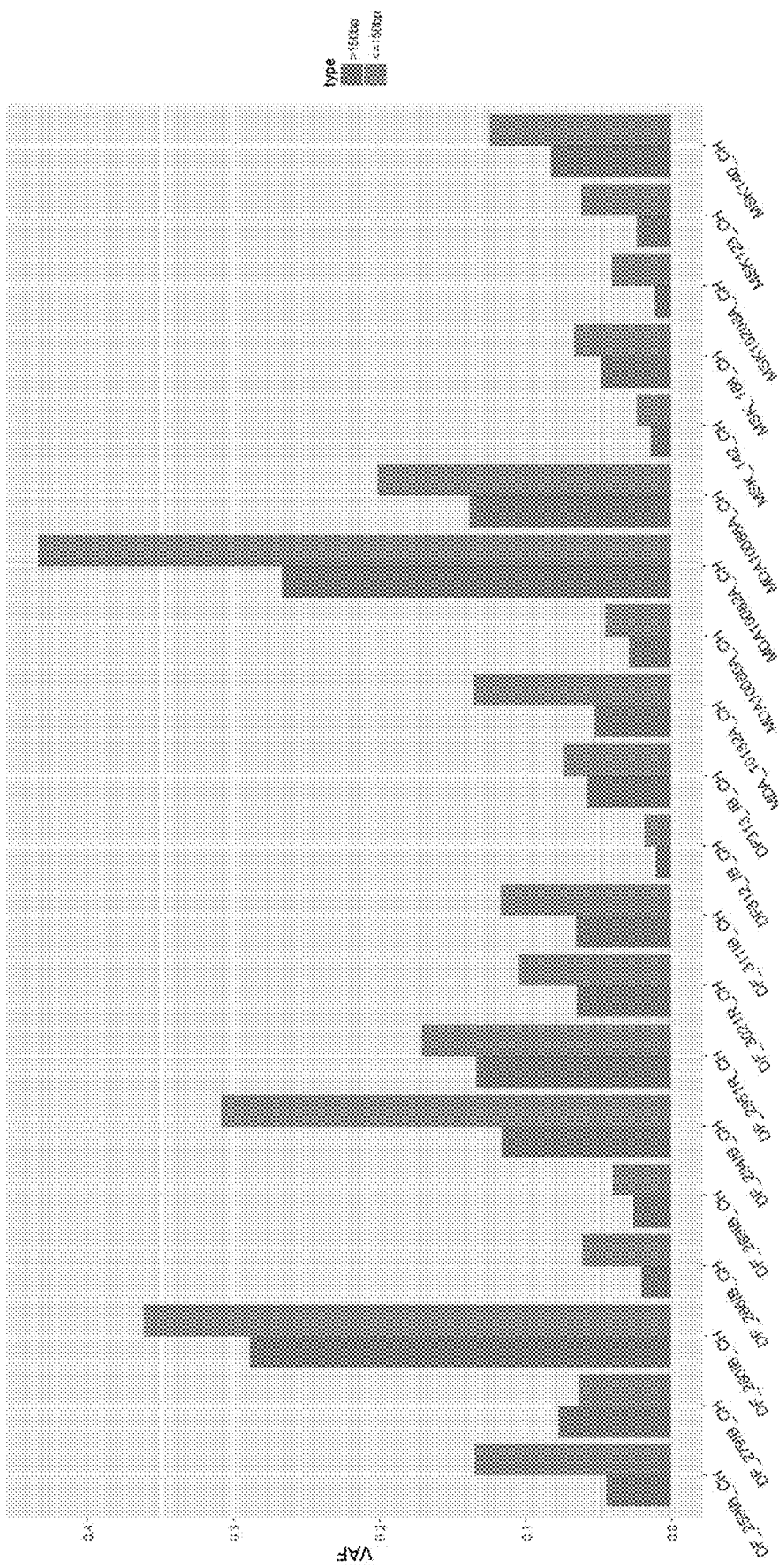
FIG. 1C shows allele frequencies for shorter cfDNA fragments (shorter than or equal to 150 bp, dark gray bars) and longer cfDNA fragments (longer than 150 bp, light gray bars).

It has been observed that cfDNA harboring cancer related variants (ctDNA) tend to have shorter fragment size (or more shorter fragments) than normal cfDNA in some studies. As illustrated in FIG. 1B, ctDNA has a fragment length distribution (FLD) with peak shifted towards the lower end. Similarly, FIG. 1C shows that shorter cfDNA fragments (shorter than or equal to 150 bp, dark gray bars) tend to have higher allele frequencies than longer cfDNA fragments (longer than 150 bp, light gray bars). Each pair of bars in the figure show data for a cancer related variant, and the vertical axis indicates variant allele frequency.

Using Size of cfDNA Fragments to Determine Variant of Interest

Various implementations provide methods for calling variants of interest, such as tumor variants or cancer-specific somatic variants, from cfDNA sequencing data. These variants fall into three major classes: Simple Nucleotide Variants (SNVs), Structural Variants (SVs) and Copy Number Variants (CNVs). SNVs include single nucleotide variants, phased sequential variants and small insertions and deletions (indels). Structural variants include chromosomal structural rearrangements including large indels, duplications, inversions, and transversions. CNVs include abnormal copy numbers of normally diploid regions of the genome. Of these three variant classes, improvements can be made to SNV and CNV calling by incorporating ctDNA fragment size information.

Figure 2:
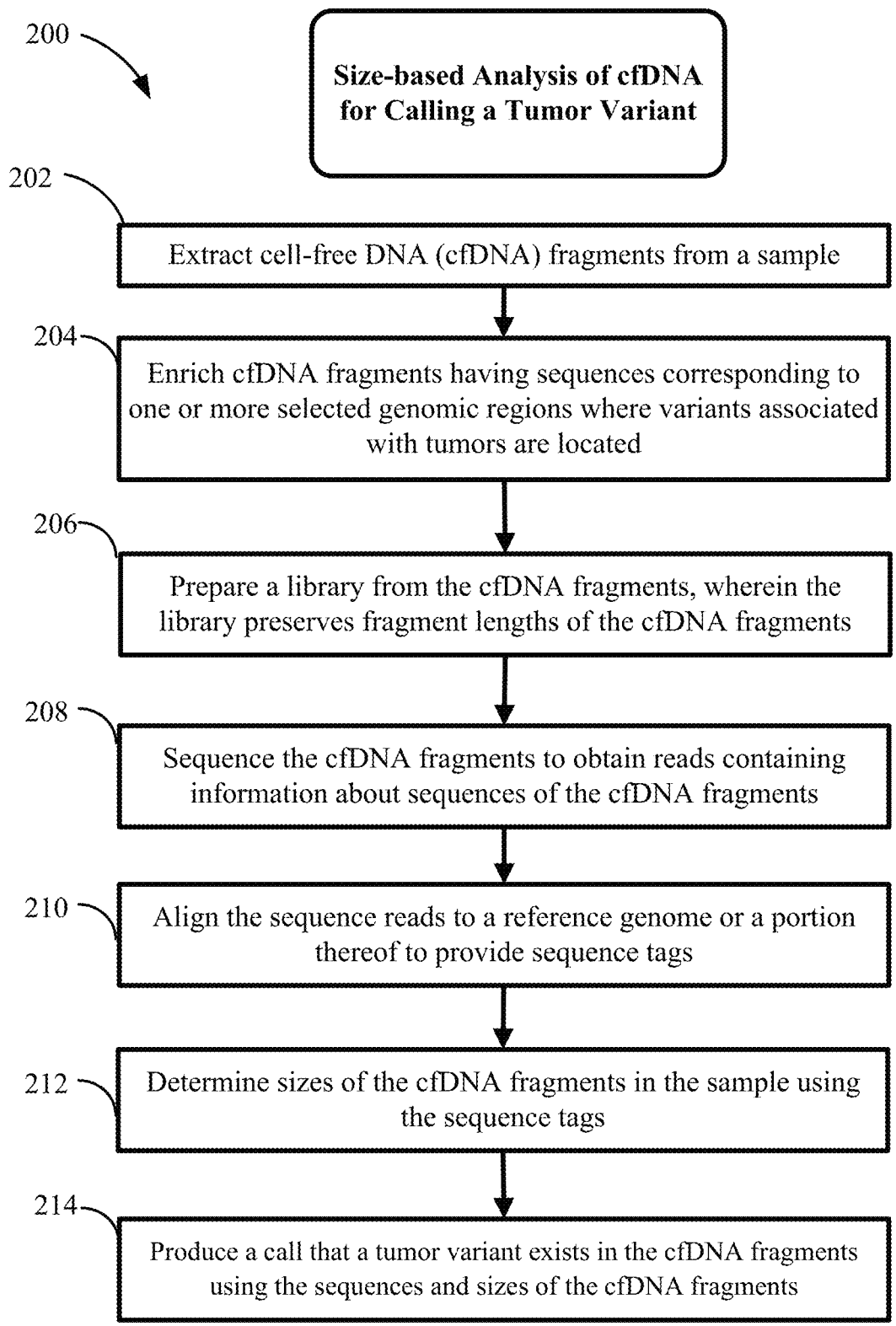
FIG. 2 shows a flowchart illustrating a process for preparing a sample and analyzing cfDNA fragments extracted from the sample, using both size and sequence information of the fragments to call a variant of interest.

FIG. 2 shows a flowchart illustrating a process 200 for preparing a sample and analyzing cfDNA fragments extracted from the sample, using both size and sequence information of the fragments to call a variant of interest (e.g., a tumor variant) in the sample. In some implementations, the tumor variant is a simple nucleotide variant (SNV). In some implementations, the SNV is a single nucleotide variant such as a SNP, a phased sequential variant, or a small indel. In some implementations, the tumor is malignant (cancerous) or potentially malignant (pre-cancerous). The process starts by obtaining a sample including cell-free DNA from an individual. The sample may be obtained from a peripheral blood, saliva, and other body fluid as further described in the sample processing section hereinafter. The process involves extracting cell free DNA fragments from the sample. See block 202. In some implementation, a relatively large amount of cfDNA may be necessary because concentrations of ctDNA for some samples can be relatively low.

To increase the probability of detecting tumor variant of interest, some implementations involve enriching sequence regions known to harbor tumor variants. In some implementations, the enrichment involves whole genome amplification of cfDNA fragments. In some implementations, the enrichment involves targeted amplification of cfDNA fragments. See operation 204. Enriching may be performed before or after sequencing library preparation. In fact, unless otherwise specified, all operations described or illustrated herein may be performed out of the order shown. Process 200 as illustrated in FIG. 2 enriches cfDNA fragments having sequences that correspond to one or more selected genomic regions where variants associated with tumors are located. Operation 204 helps to target amplification of sequences located in the regions that potentially harbor variants that are known or suspected to be associated with tumors, especially malignant or premalignant tumors. By amplifying fragments in these targeted regions, the probability of detecting cancer associated variants is increased. In some applications, targeted regions may include chromosomal, sub-chromosomal, or individual gene regions. In other applications, simple nucleotide variants may be targeted in a relatively narrow sequence range, such as 500 bp, 1000 bp, 2000 bp, 3000 bp, 4000 bp, 5000 bp, 10000 bp, or 20000 bp. In some implementations, whole genome sequencing may be performed. Such implementations are particularly useful for detecting CNVs of long sequences. In various implementations, due to a low concentration of ctDNA, a deep sequencing process is performed, e.g., to a depth of at least about 10,000×. Such deep sequencing is facilitated by targeted and whole genome amplifications.

Various implementations can be applied with or without sample amplification as long as there is no experimental procedures that disrupt the difference of tumor or healthy tissue fragment size distribution.

Process 200 involves preparing a sequencing library from cfDNA fragments extracted from the sample. See block 206. In many applications employing sequencing libraries on high throughput sequencing platforms, DNA molecules are fragmented and end-repaired. However, in the application involving cfDNA, the DNA molecules exist in fragments ranging from tens to hundreds of base pairs. In the implementations herein that use information of the fragment sizes, the library preparation should substantially preserve the size of the fragments. Therefore, harsh conditions that may break up the fragments that exist in bodily fluid should be avoided in sample preparation. Of course, separate preparations may involve certain primers and adapters that extend the length of the fragments. However, so long as the preparation affects size consistently across different fragments, the size information of the fragments can be recovered, such as in the paired end sequencing techniques described above.

In some implementations, preparing the library involves applying adapters to both ends of the extracted cfDNA fragments. In some implementations, the adapters include physical unique molecular identifiers that can be used to identify individual fragments in the sample. In some implementations, the physical unique molecular identifiers are smaller than about 12 nucleotides. Methods and systems applying unique molecular identifiers are provided in U.S. patent application Ser. No. 15/130,668, which is hereby incorporated by reference in its entirety.

Process 200 further involves sequencing the cfDNA fragments to obtain reads containing information about sequences of the cfDNA fragments. See block 208. In various implementations, paired end sequencing is used to sequence fragments from both ends. This approach can be useful when reads are shorter than the fragments, which may be the case on various high throughput sequencing platforms. In alternative implementations, single end sequencing with reads that are long enough to cover the full stretch of the DNA fragments may be used.

The sequence reads obtained from sequencing are aligned to a reference genome or portion thereof to provide sequence tags, which include sequences and alignment locations (e.g., genomic coordinates). See block 210. The alignment information of the sequence tags may determine the relative locations of two reads in a pair of paired end reads. Process 200 further involves determining sizes of the cfDNA fragments existing in the sample using information in the sequence tags. See block 212. In some implementations, the sequence tags are long enough to cover the entire size of the cfDNA fragments. In these implementations, fragment sizes can be obtained by simply counting the number of bases in the fragments during sequencing. In other implementations, the relative alignment locations of two reads in a pair can be used to determine the size of the fragment from which the reads derive. The alignment location of a read may be combined with the sequence of the read to determine whether the fragment from which the read derives potentially includes a cancer variant originating from a cancer related mutation. If a read includes the sequence of a cancer variant and optionally matches the genomic coordinates of the cancer variant, the fragment from which the read derives is also called a potentially variant-containing fragment. The fragment potentially contains a sequence originating from a cancer mutation, as the read has a small but valid chance to match the sequence and location of the cancer variant due to errors arising in the sequencing pipeline.

Process 200 then produces a call to determine whether the tumor variant exists in the cfDNA fragments using both the sequences and sizes of the cfDNA fragments. See block 214. Various implementations of processes within the scope of FIGS. 3A-3F may produce a call of the tumor variant or a condition related to the variant using the sequence and size information of the cfDNA fragments.

Figure 3A:
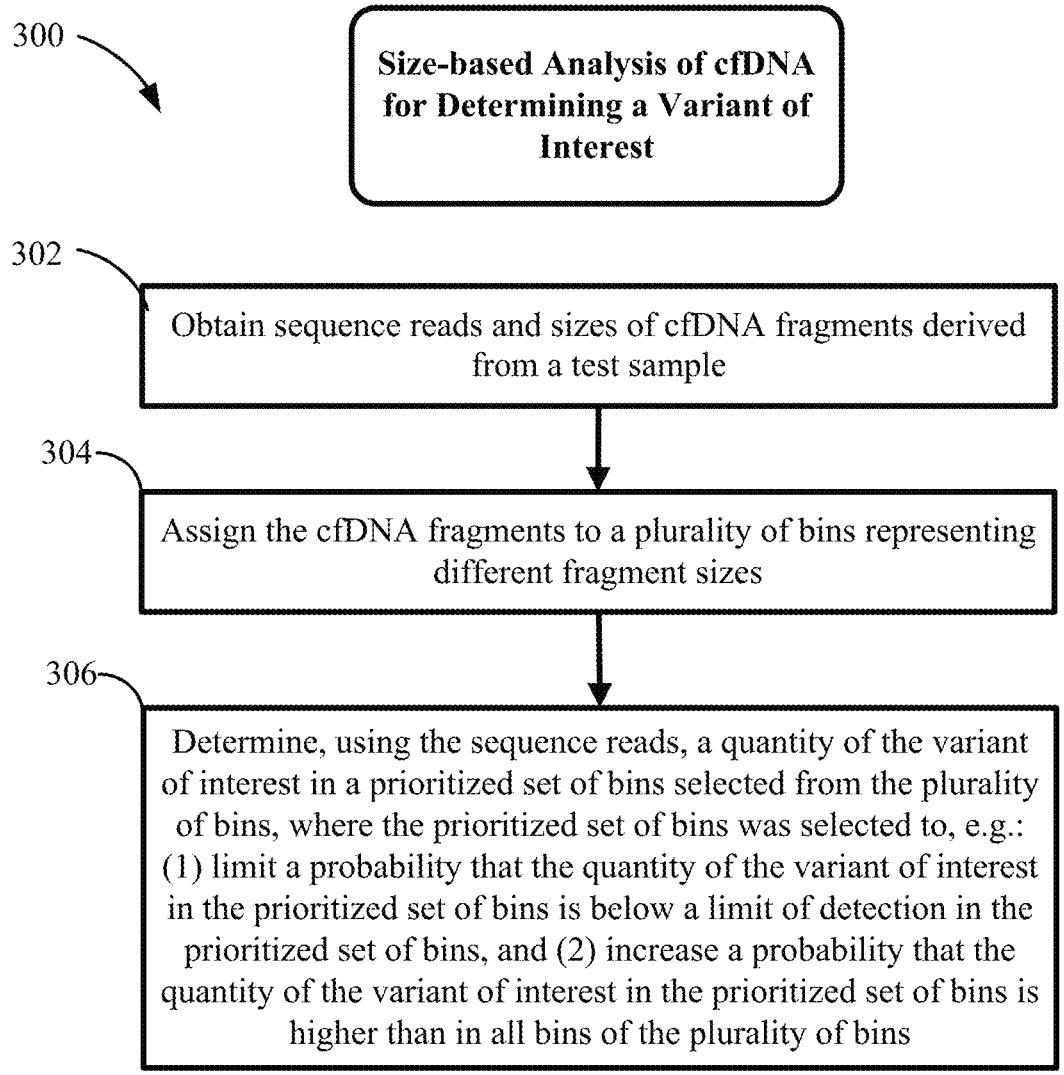
FIG. 3A shows a flowchart illustrating a process for determining a variant of interest using sequence information and size information of cfDNA fragments.

Turning to FIG. 3A, a flowchart illustrates a process 300 for determining a variant of interest using sequence information and size information of cfDNA fragments. The method may be implemented on a computer system including one or more processors and system memory further described hereinafter. The variant of interest may be an allele associated with a condition of interest. In some implementations, the variant of interest is suspected to be associated with a cancer or a tumor. For example, the variant of interest may be a BRCA mutation known to be associated with breast cancer. In some implementations, the variant of interest is known or suspected to be associated with a genetic disorder. In some implementations, the variant of interest includes a simple nucleotide variant (SNV). In some implementations, the SNV is a single nucleotide variant, a phased sequential variant, or an indel.

Process 300 starts by obtaining sequence reads of cfDNA fragments derived from a test sample. The process also obtains sizes of the cfDNA fragments derived from the test sample. See block 302. The size of a cfDNA fragment is also called fragment size, fragment length, or molecular size. In some implementations, the size information and the sequence information of the cfDNA are obtained by a process such as process 200 depicted in FIG. 2. In some implementations, the sequence reads are paired-end reads, and read pairs are used to determine the sizes of the cfDNA fragments as described above. In some implementations the cfDNA fragments include circulating tumor DNA (ctDNA) fragments when the variant of interest is associated with a tumor or a cancer. In some implementations, the test sample is a plasma sample. In some implementations, the test sample is a plasma sample of a pregnant woman, and the cfDNA includes cfDNA originating from the pregnant woman and cfDNA originating from the fetus carried by the pregnant woman.

Figure 9:
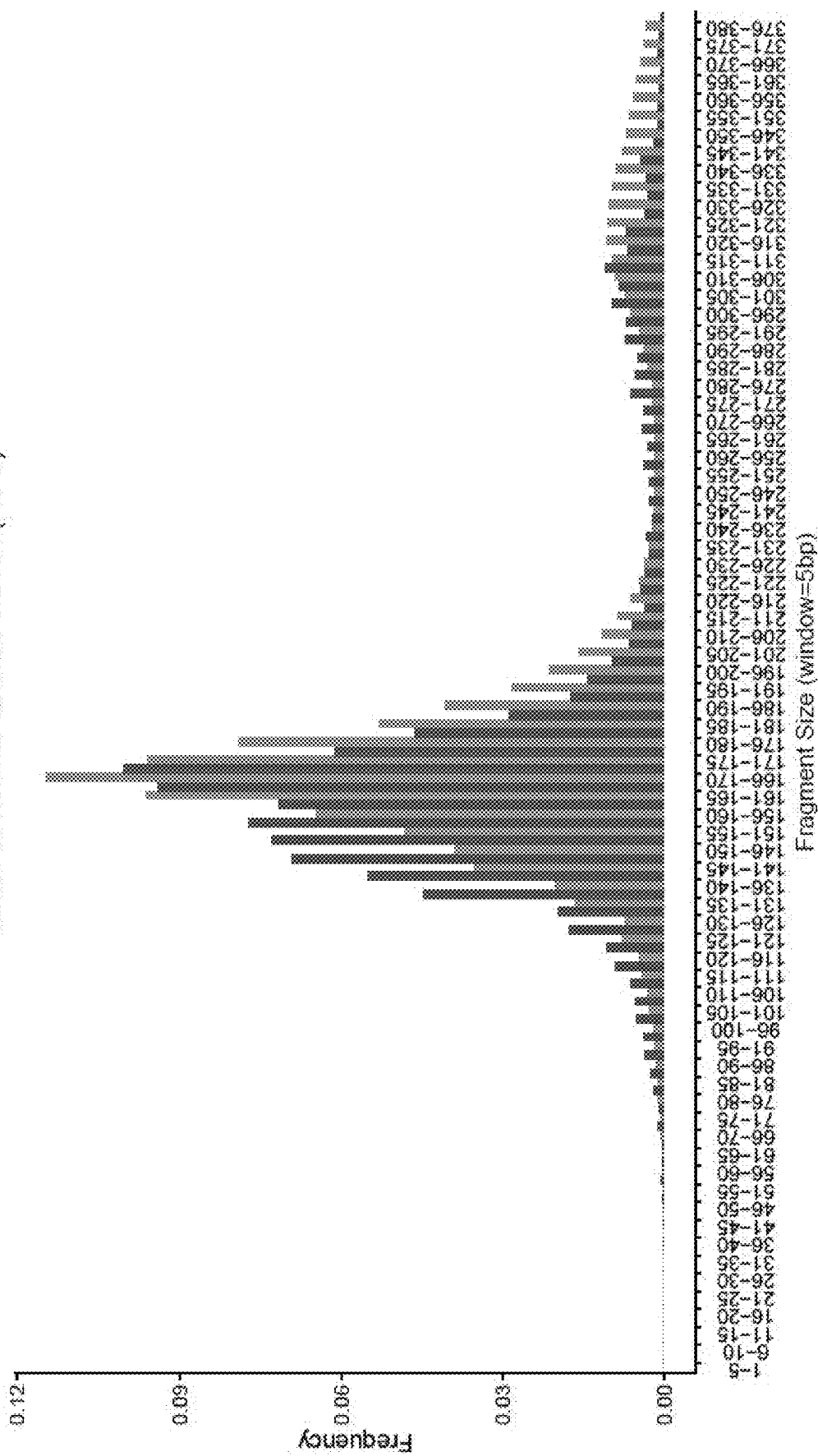
FIG. 9 shows a histogram of fragment lengths that assigns the cfDNA fragments into bins each spanning five nucleotides.

Process 300 further involves assigning the cfDNA fragments to a plurality of bins representing different fragment sizes. See block 304. In some implementations, each bin of the plurality of bins has the same bin size. In other words, each bin covers a fixed range of fragment sizes. In some implementations, the bins cover contiguous size ranges that do not overlap. For example, a first bin includes fragments of 1 to 5 nucleotides, a second bin includes fragments of 6 to 10 nucleotides, a third bin includes fragments of 11 to 16 nucleotides, a fourth bin includes fragments of 16 to 20 nucleotides, and so on. In various implementations, different bin sizes may be used, such as 2, 3, 4, 5, 6, 7, 8, 9, 10, 20, 30, 40, 50, and 100. In some implementations, the plurality of bins collectively covers a total range of 1-1000 nucleotides, 1-500 nucleotides, or 1-380 nucleotides. Different bin sizes and total ranges may be used in different implementations under different conditions. For example, FIG. 9 shows an analysis that assigns the cfDNA fragments into bins each spanning five nucleotides, the plurality of bins collectively covering a size range of 1-380 nucleotides. When cfDNA fragments are assigned to bins as shown in FIG. 9, the frequencies of cfDNA fragments in the different bins form a histogram that corresponds to a fragment length distribution, which is similar to distributions 330, 332, and 334 in FIG. 3C.

Process 300 further involves determining a quantity of the variant of interest in the prioritized set of bins selected from the plurality of bins using the sequence reads obtained in operation 302. The prioritized set of bins was selected to: (1) limit a probability that the quantity of the variant of interest in the prioritized set of bins is below a limit of detection (LOD) in the prioritized set of bins, and (2) increase the probability that the quantity of the variant of interest in the prioritized set of bins is higher than in all bins of the plurality of bins. To detect a variant related to cancer, for instance, the prioritized set of bins was selected to increase cancer related signals while ensuring that the signals in the prioritized set of bins exceed the limit of detection. In some implementations, the quantity of the variant of interest is an allele frequency of the variant of interest. In some implementations, the quantity is a count of the variant of interest in the prioritized set of bins. In some implementations, the quantity can be normalized relative to a reference or baseline.

Figure 3B:
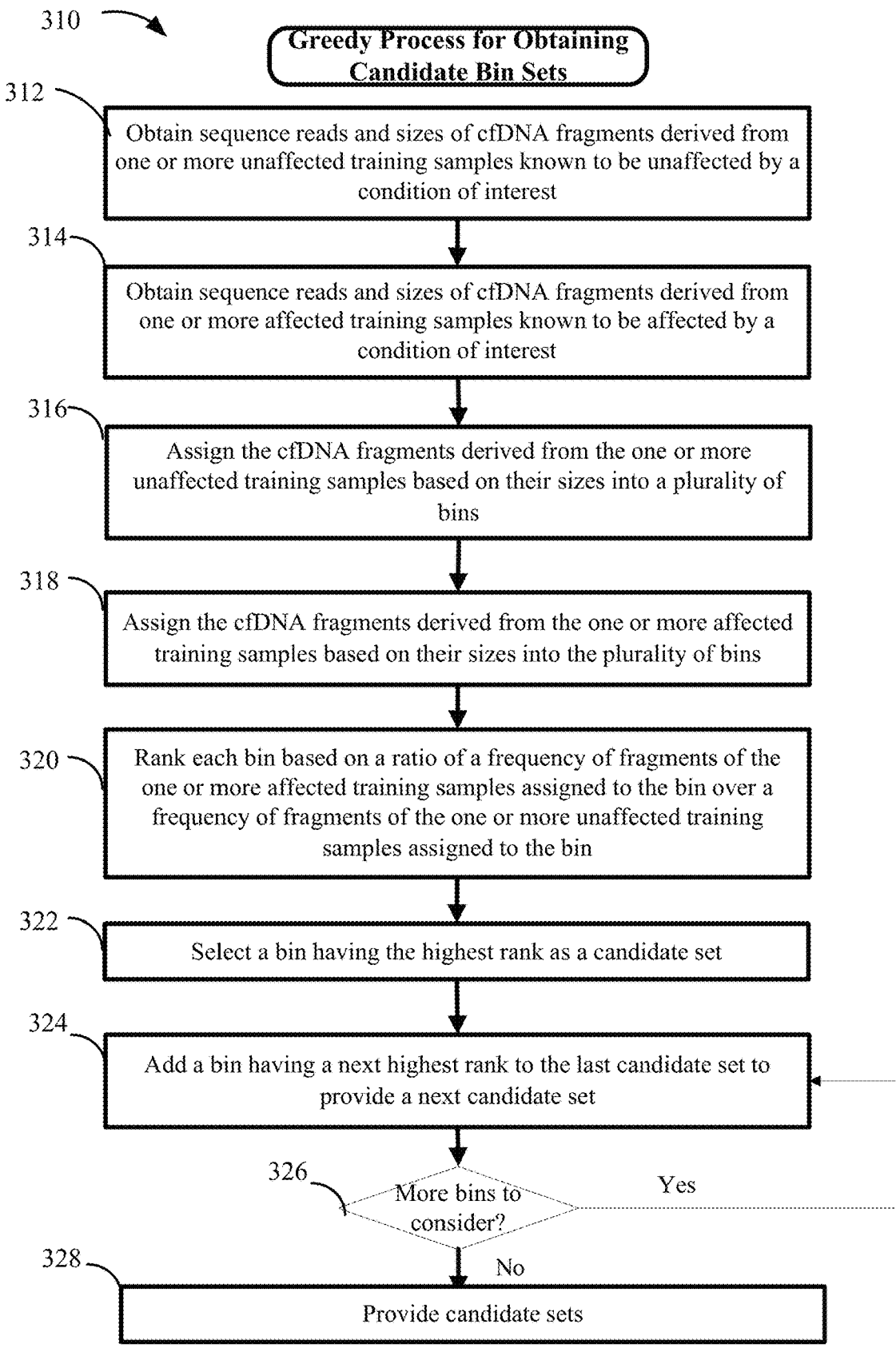
FIG. 3B shows a flowchart illustrating a greedy process for obtaining a plurality of candidate sets of bins.

In some implementations, the prioritized set of bins is obtained by providing a plurality of candidate sets and selecting a set from the plurality of candidate sets as the prioritized set. In some implementations, bins that do not include the variant of interest (e.g. a tumor related variant) are excluded from the prioritized set. In some implementations, the process of selecting or identifying the prioritized set is performed separately from using the selected bins to test a sample. In other words, the process of identifying the bins may be performed once and the selected bins are used many times to test samples. In some implementations, the plurality of candidate sets can be provided by process 310 as illustrated in FIG. 3B and explained in FIG. 3C. In some implementations, the prioritized set of bins is selected from the plurality of candidate sets using a process such as process 350 shown in FIG. 3D and explained in FIGS. 3E-3F.

In some implementations, process 300 further involves comparing the quantity of the variant of interest to a call criterion to determine a presence or abundance of the variant of interest in the test sample. In some implementations, the quantity of the variant of interest in the prioritized set of bins is an allele frequency, and the call criterion is 0.05%. Other quantity and call criteria may be used in other implementations and for various conditions. For instance, the quantity may be normalized relative to a reference quantity (e.g., allele frequency of a normalizing sequence), and suitable criteria may be empirically determined. In some implementations, a physical condition associated with the variant of interest can be determined based on the quantity of the variant of interest.

FIG. 3B is a flowchart illustrating a greedy process for obtaining a plurality of candidate sets of bins. Process 310 starts by obtaining sequence reads and sizes of cfDNA fragments derived from one or more unaffected training samples known to be unaffected by a condition of interest. See block 302. In some implementations, the condition of interest is known to be associated with a variant of interest. For example, the variance of interest and may be breast cancer, and the variant of interest may be a mutation of the BRCA1 or BRCA2 gene. In some implementations, the condition of interest is a general condition encompassing a species of condition associated with the variant of interest. For example, the variance of interest may be a BRCA mutation, while the condition of interest may be cancers in general, including breast cancer, lung cancer, stomach cancer, and/or other forms of cancers. In the former example, the prioritized bin set may be more specifically suited for detecting the cancer type associated with the variant of interest. In the letter example, candidate bin sets obtained by the greedy process 310 and the prioritized bin set selected from the candidate bin sets may be more generalizable to various types of cancers.

In some implementations, the condition of interest includes one or more cancers. In some implementations, the condition of interest includes a cancer associated with the variant of interest. In some implementations, the affected training samples include cancer cells and the unaffected training samples include healthy cells.

Process processes 310 also involves obtaining sequence reads and sizes of cfDNA fragments derived from one or more affected training samples known to be affected by the condition of interest. See block 314.

Process 310 further involves assigning the cfDNA fragments derived from the one or more unaffected training samples based on their sizes into a plurality of bins. See block 316. Assigning cfDNA fragments derived from the one or more unaffected training samples based on their sizes into the plurality of bins results in a histogram that corresponds to the fragment length distribution 330 of FIG. 3C.

Figure 3C:
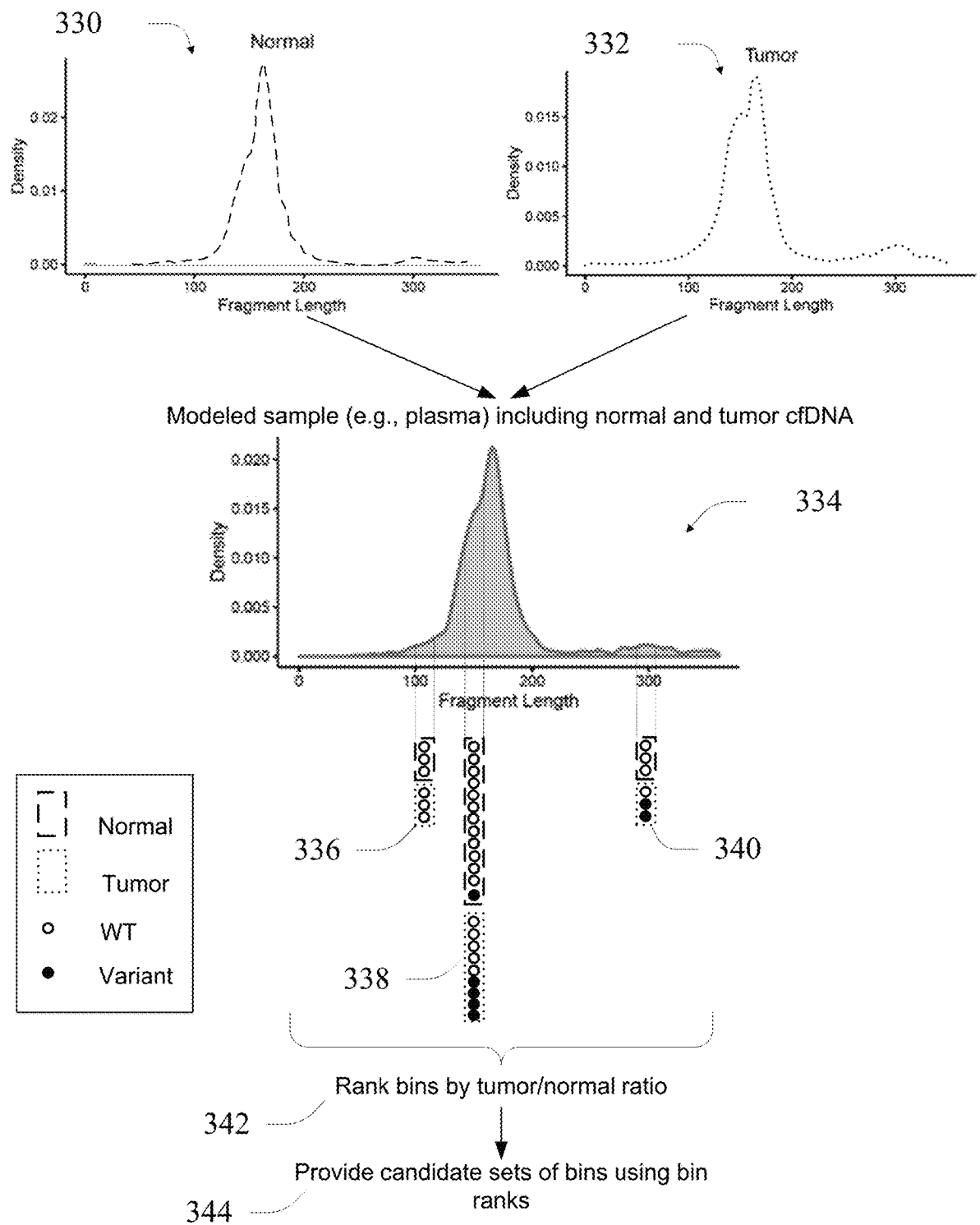
FIG. 3C illustrates how data of normal cfDNA and tumor derived DNA can be combined to model a sample such as a plasma sample including both normal and tumor related cfDNA.

FIG. 3C illustrates how data of normal cfDNA and tumor derived DNA can be combined to model a sample such as a plasma sample including both normal and tumor related cfDNA. FIG. 3C shows a fragment length distribution 330 of unaffected samples, a fragment length distribution 332 of tumor derived fragments, and a fragment length distribution 334 of a modeled sample including normal and tumor cfDNA fragments, which is obtained by combining fragments from distribution 330 and distribution 332. For example, a plasma sample of a patient affected by a tumor (therefore including normal cfDNA and tumor derived ctDNA) can have a fragment length distribution like distribution 334.

Process 310 also involves assigning the cfDNA fragments derived from the one or more affected training samples based on the sizes into the plurality of bins. See block 318. When the condition of interest is a tumor, assigning the cfDNA fragments from the unaffected training samples to the plurality of bins results in a histogram that corresponds to the fragment length distribution 332 in FIG. 3C.

Process 310 further involves ranking each bin based on a ratio of a quantity of fragments of the one or more affected training samples assigned to the bin over a quantity of fragments of the one or more unaffected training samples assigned to the bin. See block 320. See also 342 of FIG. 3C. In some implementations, the quantity of fragments is a frequency of the fragments. In some implementations, the quantity may be normalized relative to a baseline or reference level.

Each bin of the plurality of bins can contain fragments from the unaffected training samples and the affected training samples. For example, bin 336 in FIG. 3C covers fragments having sizes in a range around 100 nucleotides, and contains fragments from the normal (unaffected) samples and fragments from the cancer (or affected) samples. In the illustration of FIG. 3C, bin 336 includes three fragments from the normal samples and three segments from the tumor sample. Therefore, bin 336 provides a tumor fragment over normal fragment ratio of 1. Bin 340 also includes three fragments from the normal samples and three fragments from the tumor sample. Therefore, bin 340 also provides a tumor-derived fragment over normal fragment ratio of 1. Bin 338 includes 13 fragments from the normal samples and nine fragments from the tumor samples. Bin 338 provides a cancer over normal ratio of 9/13. As such, bins 336 and 340 are ranked higher than bin 338 in operation 320.

In FIG. 3C, fragments including a wild-type variant are illustrated as open circles, and fragments including a tumor variant are illustrated as filled circles. In some implementations, bins that include no tumor variant, such as bin 336, are excluded in the downstream process when selecting bins for a prioritized bin set.

Process 310 further involves selecting a bin having a highest rank as a candidate set. See block 322. In the example illustrated in FIG. 3C, either bin 336 or bin 340 may be selected as the candidate set in some implementations. In other implementations, other factors may be considered when two or more candidate sets have a tied rank such as bins 336 and 340. For example, the number of fragments including tumor variants may be considered to resolve a tied situation. Therefore, in the example in FIG. 3C, bin 340 is selected before bin 336 because bin 340 includes contains two fragments having a tumor variant. Other factors that may be considered to resolve a tied situation include but are not limited to: the total number of fragments in the bin, the number of fragments derived from the cancer samples, experimental considerations, and biological considerations.

Process 310 adds a bin having a next highest rank to the last candidate set to provide a next candidate set. See block 324. Operation 324 in FIG. 3B corresponds to adding bin 336 to the last candidate set including bin 340 to provide a next candidate set. The next candidate set includes bin 340 and bin 336.

Process 310 determines whether there are more bins to consider. See block 326. If there are more bins to consider, the process repeats the last step by adding another bin having a next highest rank to the last candidate set to provide the next candidate set. See the "Yes" branch of decision 326 looping back to block 324. If no more bins are to be considered, process 310 provides the obtained candidate sets. See block 328. See also operation 344 in FIG. 3C. From the candidate sets, one set is to be selected to provide bins of a prioritized set. In some implementations, the prioritized set is selected using process 350 illustrated in FIG. 3D, which process is also explained with reference to FIG. 3E.

Figure 3D:
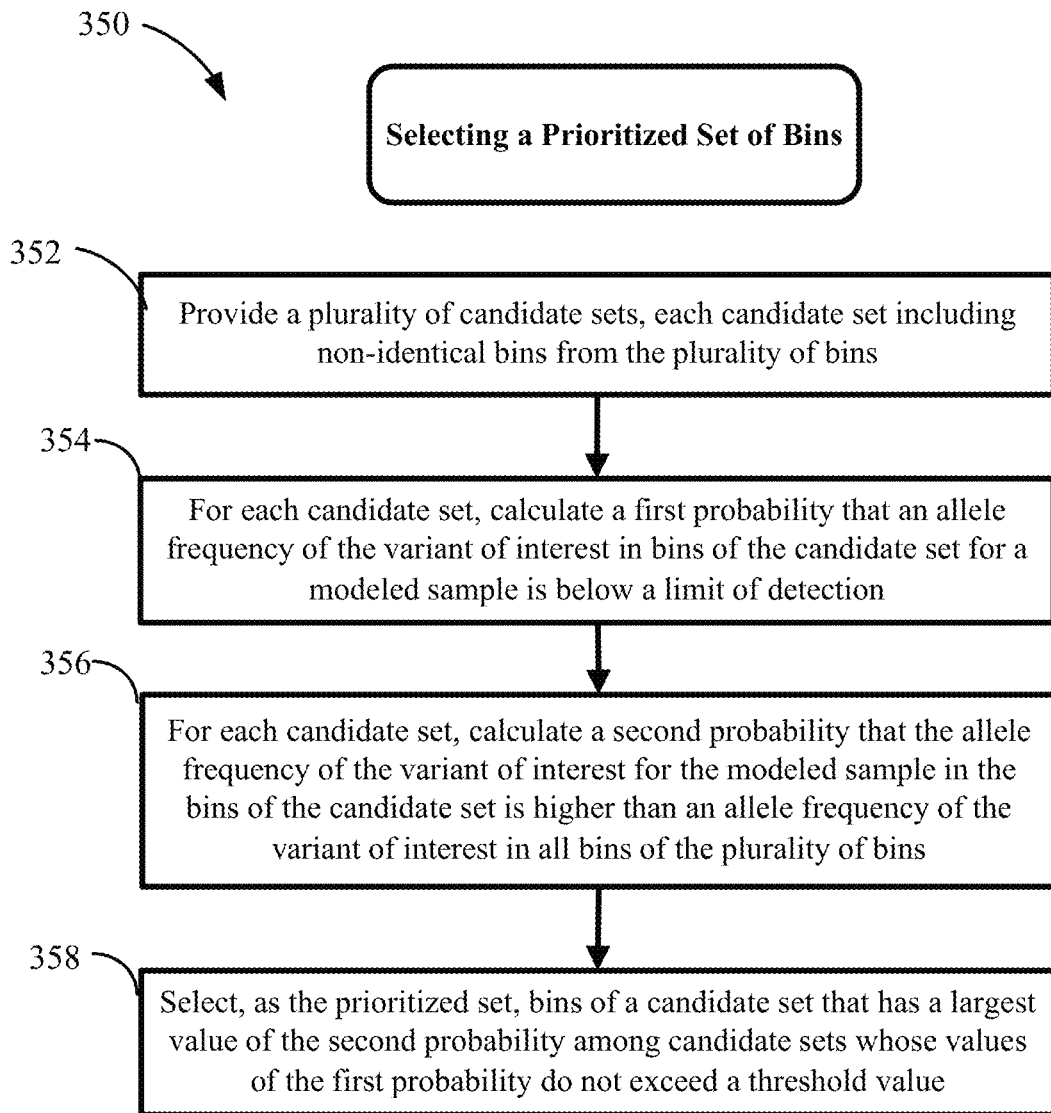
FIG. 3D shows a flow chart illustrating a process for selecting a prioritized set of bins from a plurality of candidate sets.

FIG. 3D shows a flow chart illustrating process 350 for selecting a prioritized set of bins from a plurality of candidate sets. Process 350 starts by providing a plurality of candidate sets. In some implementations, the plurality of candidate sets may be obtained by a process such as process 310 of FIG. 3B. Each candidate set includes nonidentical bins from the plurality of bins. See block 352.

Process 350 further involves calculating, for each candidate set, a first probability (P1) that an allele frequency of the variant of interest in bins of the candidates set for a modeled sample is below a limit of detection. See block 354. In some implementations, the limit of detection is about 0.05%-0.2%. In some implementations, the limit of detection is about 0.2% or 0.05%. The modeled sample can be obtained by combining normal samples associated with fragment distribution 330 and tumor samples associated with fragment lengths distribution 332. The modeled sample includes cfDNA fragments from cells not affected by the condition of interest and cfDNA from cells affected by the condition of interest.

Process 350 also involves calculating, for each candidate set, a second probability (P2) that the allele frequency of the variant of interest for the modeled sample in the bins of the candidate set is higher than an allele frequency of the variant of interest in all bins of the plurality of bins. See block 356. The allele frequency of the variance of interest for the modeled sample in all bins of the plurality of bins is also called a plasma allele frequency ($AF_{plasma}$).

Process 350 further involves selecting, as the prioritized set, bins of a candidate set with a largest value of the second probability among candidate sets whose values of the first probability do not exceed the threshold value. See block 358. In some implementations, bins that contain no fragments from the affected (or tumor) samples are excluded from the prioritized set.

FIG. 3E shows a frequency length distribution of normal samples (360) and frequency length distribution 362 of tumor samples, and how the first probability (P1) and the second probability (P2) are obtained for the modeled sample. For a given bin (bin L), one can obtain an allele frequency $\alpha(L)$ for the tumor samples and an allele frequency $\beta(L)$ for the normal samples. Allele frequencies $\alpha(L)$ and $\beta(L)$ can be used to calculate an allele frequency of bins for the modeled sample as follows:

$$AF(L_{b1,b2\ldots bk}) = \frac{N_{mut}(L_{b1,b2\ldots bk})}{DP * [f_{tumor} * \Sigma_{b1}^{bk}\alpha(L_{bi}) + (1 - f_{tumor}) * \Sigma_{b1}^{bk}\beta(L_{bi})]}$$

where:

$AF(L_{b1, b2 \ldots bk})$ is an allele frequency for bins $L_{b1}$, $L_{b2} \ldots L_{bk}$;

$N_{mut}(L_{b1, b2 \ldots bk})$ is a count of the variant of interest in bins $L_{b1}, L_{b2} \ldots L_{bk}$;

DP is a sequencing depth;

$f_{tumor}$ is a fraction of cfDNA from cells harboring the variant of interest;

$\alpha(L_{b1})$ is a density of fragments in bin $L_{b1}$ in a fragment length distribution of one or more affected samples known to be affected by a condition of interest; and $\beta(L_{bi})$ is a density of fragments in bin $L_{bi}$ in a fragment length distribution of one or more unaffected samples known not to be affected by a condition of interest.

In some implementations, the count of the variant of interest in bins $L_{b1}, L_{b2} \ldots L_{bk}$ can be modeled as a binomial distribution:

$$N_{mut}(L_{b1,b2\ldots bk}) \sim \text{Binomial}(\Sigma_{b1}^{bk} DP * f_{tumor} * \alpha(L_{bi}), AF_{tumor})$$

where $AF_{tumor}$ is the allele frequency of the variant of interest in the tissues harboring the variant of interest.

In some implementations, $AF_{tumor}$ is calculated as:

$$AF_{tumor} = AF_{plasma}/f_{tumor}$$

where $AF_{plasma}$ is the allele frequency of the variant of interest in the modeled sample in all bins of the plurality of bins.

Using the allele frequency (and its probabilistic distribution) of the variant of interest for the modeled sample in the bins of the candidate set, and the allele frequency (and its probabilistic distribution) of the variant of interest in all bins of the plurality of bins, one can obtain P1 and P2. After the P1 and P2 are obtained, data of the two probabilities for the plurality of candidate sets can be used to select a candidate set, so the selected candidate set has a largest value of the second probability (P2) among candidate sets whose values of the first probably (P1) do not exceed a threshold value. See block 358. In some implementations, the threshold value is about 0.002.

Figure 3F:
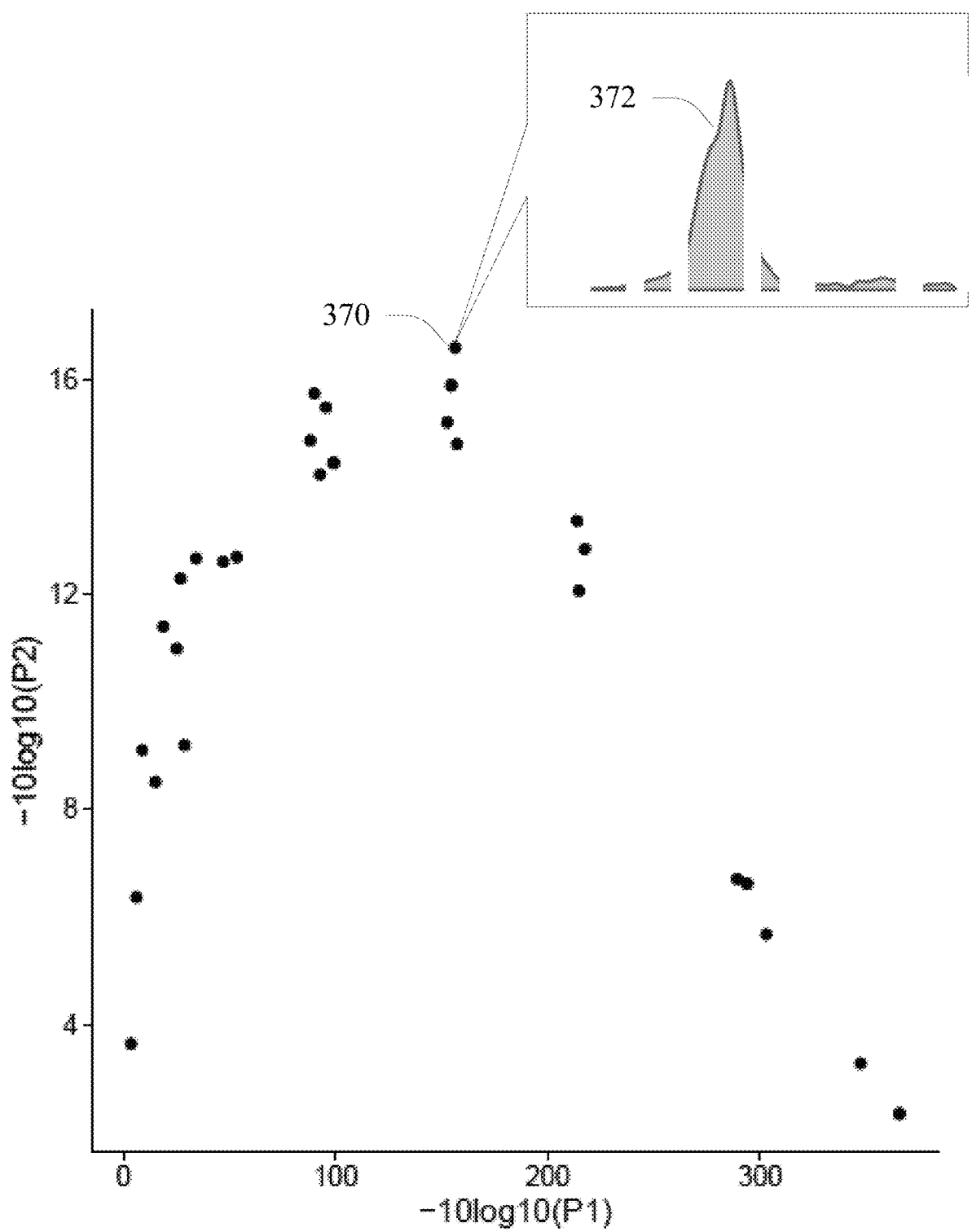
FIG. 3F shows probability data for a plurality of candidate sets.

FIG. 3F plots the two probabilities for a plurality of candidate sets. The data point 370 has the largest probably P2 among all data points (which is also the largest among all data points with P1 values below a threshold value). The probably P1 of data point 370 is below a threshold value (e.g. 200 on a log scale). Therefore, the candidates set corresponding to data point 370 is selected as the prioritized set. The prioritized set of bins are illustrated as bin set 372 in the insert of FIG. 3F. In some implementations, bins that contain no fragments of variant of interest (e.g. tumor variant) are excluded from the prioritized bin set.

In some implementations, when selecting a prioritized bin set, the second probably (P2) is considered, while the first probably (P1) is optionally considered. In some implementations, a method for analyzing cell free DNA includes: (a) obtaining, by the computer system, sequence reads and sizes of cfDNA fragments derived from a test sample; (b) assigning, by the one or more processors, the cfDNA fragments into a plurality of bins representing different fragment sizes; and (c) determining, using the sequence reads and by the one or more processors, a quantity of the variant of interest in a prioritized set of bins selected from the plurality of bins, wherein the prioritized set of bins were selected by a process including: (i) providing a plurality of candidate sets, each candidate set including non-identical bins from the plurality of bins; (ii) for each candidate set, calculating a second probability that an allele frequency of the variant of interest in bins of the candidate set in a modeled sample is above an allele frequency of the variant of interest in all bins of the plurality of bins in the modeled sample; and (iii) selecting, as the prioritized set, bins of a candidate set with a largest value of the second probability among the plurality of candidate sets. Each candidate set including non-identical bins means that each candidate set has bins that are not identical to bins of other candidate sets.

In some implementations, the method further comprising, before (iii) and for each candidate set, calculating a first probability that the allele frequency of the variant of interest in the bins of the candidate set in the modeled sample is below a limit of detection, wherein (iii) includes selecting, as the prioritized set, bins of a candidate set with a largest value of the second probability among candidate sets whose values of the first probability do not exceed a threshold value.

Fragment lengths can also improve the performance of CNV calling. Methods and systems using fragment size, fragment sequence, and sequence coverage for determining CNV are provided in U.S. patent application Ser. No. 15/382,508, which is hereby incorporated by reference in its entirety. Briefly, CNV calling is typically performed by comparing the coverage within a bin of genomic regions against a baseline. The baseline can be a set of controls or from control regions within a sample expected to not have copy number changes. Where bin-coverage is compared against a set of controls, fragment size can be utilized as an independent feature supporting CNVs.

Samples and Sample Processing

Samples

Samples that are used for calling a variant or determining a CNV contain nucleic acids that are "cell-free" (e.g., cfDNA). Cell-free nucleic acids, including cell-free DNA, can be obtained by various methods known in the art from biological samples including but not limited to plasma, serum, and urine (see, e.g., Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997]; Botezatu et al., Clin Chem. 46: 1078-1084, 2000; and Su et al., J Mol. Diagn. 6: 101-107 [2004]). To separate cell-free DNA from cells in a sample, various methods including, but not limited to fractionation, centrifugation (e.g., density gradient centrifugation), DNA-specific precipitation, or high-throughput cell sorting and/or other separation methods can be used. Commercially available kits for manual and automated separation of cfDNA are available (Roche Diagnostics, Indianapolis, Ind., Qiagen, Valencia, Calif., Macherey-Nagel, Duren, Del.). Biological samples comprising cfDNA have been used in assays to determine the presence or absence of chromosomal abnormalities, e.g., trisomy 21, by sequencing assays that can detect chromosomal aneuploidies and/or various polymorphisms.

In various embodiments the cfDNA present in the sample can be enriched specifically or non-specifically prior to use (e.g., prior to preparing a sequencing library). Non-specific enrichment of sample DNA refers to the whole genome amplification of the genomic DNA fragments of the sample that can be used to increase the level of the sample DNA prior to preparing a cfDNA sequencing library. Non-specific enrichment can be the selective enrichment of one of the two genomes present in a sample that comprises more than one genome. For example, non-specific enrichment can be selective of the cancer genome in a plasma sample, which can be obtained by known methods to increase the relative proportion of cancer to normal DNA in a sample. Alternatively, non-specific enrichment can be the non-selective amplification of both genomes present in the sample. For example, non-specific amplification can be of cancer and normal DNA in a sample comprising a mixture of DNA from the cancer and normal genomes. Methods for whole genome amplification are known in the art. Degenerate oligonucleotide-primed PCR (DOP), primer extension PCR technique (PEP) and multiple displacement amplification (MDA) are examples of whole genome amplification methods. In some embodiments, the sample comprising the mixture of cfDNA from different genomes is un-enriched for cfDNA of the genomes present in the mixture. In other embodiments, the sample comprising the mixture of cfDNA from different genomes is non-specifically enriched for any one of the genomes present in the sample.

The sample comprising the nucleic acid(s) to which the methods described herein are applied typically comprises a biological sample ("test sample"), e.g., as described above. In some embodiments, the nucleic acid(s) to be screened for one or more SNVs or CNVs is purified or isolated by any of a number of well-known methods.

Accordingly, in certain embodiments the sample comprises or consists of a purified or isolated polynucleotide, or it can comprise samples such as a tissue sample, a biological fluid sample, a cell sample, and the like. Suitable biological fluid samples include, but are not limited to blood, plasma, serum, sweat, tears, sputum, urine, sputum, ear flow, lymph, saliva, cerebrospinal fluid, ravages, bone marrow suspension, vaginal flow, trans-cervical lavage, brain fluid, ascites, milk, secretions of the respiratory, intestinal and genitourinary tracts, amniotic fluid, milk, and leukophoresis samples. In some embodiments, the sample is a sample that is easily obtainable by non-invasive procedures, e.g., blood, plasma, serum, sweat, tears, sputum, urine, sputum, ear flow, saliva or feces. In certain embodiments the sample is a peripheral blood sample, or the plasma and/or serum fractions of a peripheral blood sample. In other embodiments, the biological sample is a swab or smear, a biopsy specimen, or a cell culture. In another embodiment, the sample is a mixture of two or more biological samples, e.g., a biological sample can comprise two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In certain embodiments, samples can be obtained from sources, including, but not limited to, samples from different individuals, samples from different developmental stages of the same or different individuals, samples from different diseased individuals (e.g., individuals with cancer or suspected of having a genetic disorder), normal individuals, samples obtained at different stages of a disease in an individual, samples obtained from an individual subjected to different treatments for a disease, samples from individuals subjected to different environmental factors, samples from individuals with predisposition to a pathology, samples individuals with exposure to an infectious disease agent (e.g., HIV), and the like.

In one illustrative, but non-limiting embodiment, the sample is a maternal sample that is obtained from a pregnant female, for example a pregnant woman. In this instance, the sample can be analyzed using the methods described herein to provide a prenatal diagnosis of potential chromosomal abnormalities in the fetus. The maternal sample can be a tissue sample, a biological fluid sample, or a cell sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples.

In another illustrative, but non-limiting embodiment, the maternal sample is a mixture of two or more biological samples, e.g., the biological sample can comprise two or more of a biological fluid sample, a tissue sample, and a cell culture sample. In some embodiments, the sample is a sample that is easily obtainable by non-invasive procedures, e.g., blood, plasma, serum, sweat, tears, sputum, urine, milk, sputum, ear flow, saliva and feces. In some embodiments, the biological sample is a peripheral blood sample, and/or the plasma and serum fractions thereof. In other embodiments, the biological sample is a swab or smear, a biopsy specimen, or a sample of a cell culture. As disclosed above, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In certain embodiments samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue and/or cells.

Methods of isolating nucleic acids from biological sources are well known and will differ depending upon the nature of the source. One of skill in the art can readily isolate nucleic acid(s) from a source as needed for the method described herein. In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing. In one embodiment, sample nucleic acids are obtained from as cfDNA, which is not subjected to fragmentation.

Sequencing Library Preparation

In one embodiment, the methods described herein can utilize next generation sequencing technologies (NGS), that allow multiple samples to be sequenced individually as genomic molecules (i.e., singleplex sequencing) or as pooled samples comprising indexed genomic molecules (e.g., multiplex sequencing) on a single sequencing run. These methods can generate up to several hundred million reads of DNA sequences. In various embodiments the sequences of genomic nucleic acids, and/or of indexed genomic nucleic acids can be determined using, for example, the Next Generation Sequencing Technologies (NGS) described herein. In various embodiments analysis of the massive amount of sequence data obtained using NGS can be performed using one or more processors as described herein.

In various embodiments the use of such sequencing technologies does not involve the preparation of sequencing libraries.

However, in certain embodiments the sequencing methods contemplated herein involve the preparation of sequencing libraries. In one illustrative approach, sequencing library preparation involves the production of a random collection of adapter-modified DNA fragments (e.g., polynucleotides) that are ready to be sequenced. Sequencing libraries of polynucleotides can be prepared from DNA or RNA, including equivalents, analogs of either DNA or cDNA, for example, DNA or cDNA that is complementary or copy DNA produced from an RNA template, by the action of reverse transcriptase. The polynucleotides may originate in double-stranded form (e.g., dsDNA such as genomic DNA fragments, cDNA, PCR amplification products, and the like) or, in certain embodiments, the polynucleotides may originated in single-stranded form (e.g., ssDNA, RNA, etc.) and have been converted to dsDNA form. By way of illustration, in certain embodiments, single stranded mRNA molecules may be copied into double-stranded cDNAs suitable for use in preparing a sequencing library. The precise sequence of the primary polynucleotide molecules is generally not material to the method of library preparation, and may be known or unknown. In one embodiment, the polynucleotide molecules are DNA molecules. More particularly, in certain embodiments, the polynucleotide molecules represent the entire genetic complement of an organism or substantially the entire genetic complement of an organism, and are genomic DNA molecules (e.g., cellular DNA, cell free DNA (cfDNA), etc.), that typically include both intron sequence and exon sequence (coding sequence), as well as non-coding regulatory sequences such as promoter and enhancer sequences. In certain embodiments, the primary polynucleotide molecules comprise human genomic DNA molecules, e.g., cfDNA molecules present in peripheral blood of a pregnant subject.

Preparation of sequencing libraries for some NGS sequencing platforms is facilitated by the use of polynucleotides comprising a specific range of fragment sizes. Preparation of such libraries typically involves the fragmentation of large polynucleotides (e.g. cellular genomic DNA) to obtain polynucleotides in the desired size range.

Fragmentation can be achieved by any of a number of methods known to those of skill in the art. For example, fragmentation can be achieved by mechanical means including, but not limited to nebulization, sonication and hydroshear. However mechanical fragmentation typically cleaves the DNA backbone at C—O, P—O and C—C bonds resulting in a heterogeneous mix of blunt and 3'- and 5'-overhanging ends with broken C—O, P—O and/C—C bonds (see, e.g., Alnemri and Liwack, J Biol. Chem 265:17323-17333 [1990]; Richards and Boyer, J Mol Biol 11:327-240 [1965]) which may need to be repaired as they may lack the requisite 5'-phosphate for the subsequent enzymatic reactions, e.g., ligation of sequencing adaptors, that are required for preparing DNA for sequencing.

In contrast, cfDNA, typically exists as fragments of less than about 300 base pairs and consequently, fragmentation is not typically necessary for generating a sequencing library using cfDNA samples.

Typically, whether polynucleotides are forcibly fragmented (e.g., fragmented in vitro), or naturally exist as fragments, they are converted to blunt-ended DNA having 5'-phosphates and 3'-hydroxyl. Standard protocols, e.g., protocols for sequencing using, for example, the Illumina platform as described elsewhere herein, instruct users to end-repair sample DNA, to purify the end-repaired products prior to dA-tailing, and to purify the dA-tailing products prior to the adaptor-ligating steps of the library preparation.

Various embodiments of methods of sequence library preparation described herein obviate the need to perform one or more of the steps typically mandated by standard protocols to obtain a modified DNA product that can be sequenced by NGS. An abbreviated method (ABB method), a 1-step method, and a 2-step method are examples of methods for preparation of a sequencing library, which can be found in patent application Ser. No. 13/555,037 filed on Jul. 20, 2012, which is incorporated by reference by its entirety.

Sequencing Methods

As indicated above, the prepared samples (e.g., Sequencing Libraries) are sequenced as part of the procedure for identifying SNVs or CNVs. Any of a number of sequencing technologies can be utilized.

Some sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies include, but are not limited to, the SMRT™ technology of Pacific Biosciences, the ION TORREN™ technology, and nanopore sequencing developed for example, by Oxford Nanopore Technologies.

While the automated Sanger method is considered as a 'first generation' technology, Sanger sequencing including the automated Sanger sequencing, can also be employed in the methods described herein. Additional suitable sequencing methods include, but are not limited to nucleic acid imaging technologies, e.g., atomic force microscopy (AFM) or transmission electron microscopy (TEM). Illustrative sequencing technologies are described in greater detail below.

In one illustrative, but non-limiting, embodiment, the methods described herein comprise obtaining sequence information for the nucleic acids in a test sample, e.g., cfDNA in a maternal sample, cfDNA or cellular DNA in a subject being screened for a cancer, and the like, using Illumina's sequencing-by-synthesis and reversible terminator-based sequencing chemistry (e.g. as described in Bentley et al., Nature 6:53-59 [2009]). Template DNA can be genomic DNA, e.g., cellular DNA or cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments approximately 170 base pairs (bp) in length (Fan et al., Clin Chem 56:1279-1286 [2010]), and no fragmentation of the DNA is required prior to sequencing. Circulating tumor DNA also exist in short fragments, with a size distribution peaking at about 150-170 bp. Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchor oligos (not to be confused with the anchor/anchored reads in the analysis of repeat expansion). Under limiting-dilution conditions, adapter-modified, single-stranded template DNA is added to the flow cell and immobilized by hybridization to the anchor oligos. Attached DNA fragments are extended and bridge amplified to create an ultra-high density sequencing flow cell with hundreds of millions of clusters, each containing about 1,000 copies of the same template. In one embodiment, the randomly fragmented genomic DNA is amplified using PCR before it is subjected to cluster amplification. Alternatively, an amplification-free (e.g., PCR free) genomic library preparation is used, and the randomly fragmented genomic DNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about tens to a few hundred base pairs are aligned against a reference genome and unique mapping of the short sequence reads to the reference genome are identified using specially developed data analysis pipeline software. After completion of the first read, the templates can be regenerated in situ to enable a second read from the opposite end of the fragments. Thus, either single-end or paired end sequencing of the DNA fragments can be used.

Various embodiments of the disclosure may use sequencing by synthesis that allows paired end sequencing. In some embodiments, the sequencing by synthesis platform by Illumina involves clustering fragments. Clustering is a process in which each fragment molecule is isothermally amplified. In some embodiments, as the example described here, the fragment has two different adaptors attached to the two ends of the fragment, the adaptors allowing the fragment to hybridize with the two different oligos on the surface of a flow cell lane. The fragment further includes or is connected to two index sequences at two ends of the fragment, which index sequences provide labels to identify different samples in multiplex sequencing. In some sequencing platforms, a fragment to be sequenced is also referred to as an insert.

In some implementation, a flow cell for clustering in the Illumina platform is a glass slide with lanes. Each lane is a glass channel coated with a lawn of two types of oligos. Hybridization is enabled by the first of the two types of oligos on the surface. This oligo is complementary to a first adapter on one end of the fragment. A polymerase creates a compliment strand of the hybridized fragment. The double-stranded molecule is denatured, and the original template strand is washed away. The remaining strand, in parallel with many other remaining strands, is clonally amplified through bridge application.

In bridge amplification, a strand folds over, and a second adapter region on a second end of the strand hybridizes with the second type of oligos on the flow cell surface. A polymerase generates a complimentary strand, forming a double-stranded bridge molecule. This double-stranded molecule is denatured resulting in two single-stranded molecules tethered to the flow cell through two different oligos. The process is then repeated over and over, and occurs simultaneously for millions of clusters resulting in clonal amplification of all the fragments. After bridge amplification, the reverse strands are cleaved and washed off, leaving only the forward strands. The 3' ends are blocked to prevent unwanted priming.

After clustering, sequencing starts with extending a first sequencing primer to generate the first read. With each cycle, fluorescently tagged nucleotides compete for addition to the growing chain. Only one is incorporated based on the sequence of the template. After the addition of each nucleotide, the cluster is excited by a light source, and a characteristic fluorescent signal is emitted. The number of cycles determines the length of the read. The emission wavelength and the signal intensity determine the base call. For a given cluster all identical strands are read simultaneously. Hundreds of millions of clusters are sequenced in a massively parallel manner. At the completion of the first read, the read product is washed away.

In the next step of protocols involving two index primers, an index 1 primer is introduced and hybridized to an index 1 region on the template. Index regions provide identification of fragments, which is useful for de-multiplexing samples in a multiplex sequencing process. The index 1 read is generated similar to the first read. After completion of the index 1 read, the read product is washed away and the 3' end of the strand is de-protected. The template strand then folds over and binds to a second oligo on the flow cell. An index 2 sequence is read in the same manner as index 1. Then an index 2 read product is washed off at the completion of the step.

After reading two indices, read 2 initiates by using polymerases to extend the second flow cell oligos, forming a double-stranded bridge. This double-stranded DNA is denatured, and the 3' end is blocked. The original forward strand is cleaved off and washed away, leaving the reverse strand. Read 2 begins with the introduction of a read 2 sequencing primer. As with read 1, the sequencing steps are repeated until the desired length is achieved. The read 2 product is washed away. This entire process generates millions of reads, representing all the fragments. Sequences from pooled sample libraries are separated based on the unique indices introduced during sample preparation. For each sample, reads of similar stretches of base calls are locally clustered. Forward and reversed reads are paired creating contiguous sequences. These contiguous sequences are aligned to the reference genome for variant identification.

The sequencing by synthesis example described above involves paired end reads, which is used in many of the embodiments of the disclosed methods. Paired end sequencing involves two reads from the two ends of a fragment. When a pair of reads are mapped to a reference sequence, the base-pair distance between the two reads can be determined, which distance can then be used to determine the length of the fragments from which the reads were obtained. In some instances, a fragment straddling two bins would have one of its pair-end read aligned to one bin, and another to an adjacent bin. This gets rarer as the bins get longer or the reads get shorter. Various methods may be used to account for the bin-membership of these fragments. For instance, they can be omitted in determining fragment size frequency of a bin; they can be counted for both of the adjacent bins; they can be assigned to the bin that encompasses the larger number of base pairs of the two bins; or they can be assigned to both bins with a weight related to portion of base pairs in each bin.

Paired end reads may use insert of different length (i.e., different fragment size to be sequenced). As the default meaning in this disclosure, paired end reads are used to refer to reads obtained from various insert lengths. In some instances, to distinguish short-insert paired end reads from long-inserts paired end reads, the latter is also referred to as mate pair reads. In some embodiments involving mate pair reads, two biotin junction adaptors first are attached to two ends of a relatively long insert (e.g., several kb). The biotin junction adaptors then link the two ends of the insert to form a circularized molecule. A sub-fragment encompassing the biotin junction adaptors can then be obtained by further fragmenting the circularized molecule. The sub-fragment including the two ends of the original fragment in opposite sequence order can then be sequenced by the same procedure as for short-insert paired end sequencing described above. Further details of mate pair sequencing using an Illumina platform is shown in an online publication at the following URL, which is incorporated by reference by its entirety: res dot illumina dot com/documents/products/technotes/technote_nextera_matepair_data_processing. Additional information about paired end sequencing can be found in U.S. Pat. No. 7,601,499 and US Patent Publication No. 2012/0,053,063, which are incorporated by reference with regard to materials on paired end sequencing methods and apparatuses.

After sequencing of DNA fragments, sequence reads of predetermined length, e.g., 100 bp, are mapped or aligned to a known reference genome. The mapped or aligned reads and their corresponding locations on the reference sequence are also referred to as tags. In one embodiment, the reference genome sequence is the NCBI36/hg18 sequence, which is available on the world wide web at genome dot ucsc dot edu/cgi-bin/hgGateway?org=Human&db=hg1 8&hgsid=166260105). Alternatively, the reference genome sequence is the GRCh37/hg19, which is available on the world wide web at genome dot ucsc dot edu/cgi-bin/hgGateway. Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, Calif., USA). In one embodiment, one end of the clonally expanded copies of the plasma cfDNA molecules is sequenced and processed by bioinformatics alignment analysis for the Illumina Genome Analyzer, which uses the Efficient Large-Scale Alignment of Nucleotide Databases (ELAND) software.

In one illustrative, but non-limiting, embodiment, the methods described herein comprise obtaining sequence information for the nucleic acids in a test sample, e.g., cfDNA in a maternal sample, cfDNA or cellular DNA in a subject being screened for a cancer, and the like, using single molecule sequencing technology of the Helicos True Single Molecule Sequencing (tSMS) technology (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. In certain embodiments the templates can be at a density of about 100 million templates/cm2. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes or typically obviates PCR-based amplification in the preparation of the sequencing libraries, and the methods allow for direct measurement of the sample, rather than measurement of copies of that sample.

In another illustrative, but non-limiting embodiment, the methods described herein comprise obtaining sequence information for the nucleic acids in the test sample, e.g., cfDNA in a maternal test sample, cfDNA or cellular DNA in a subject being screened for a cancer, and the like, using the 454 sequencing (Roche) (e.g. as described in Margulies, M. et al. Nature 437:376-380 [2005]). 454 sequencing typically involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (e.g., picoliter-sized wells). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is measured and analyzed.

In another illustrative, but non-limiting, embodiment, the methods described herein comprises obtaining sequence information for the nucleic acids in the test sample, e.g., cfDNA in a maternal test sample, cfDNA or cellular DNA in a subject being screened for a cancer, and the like, using the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In another illustrative, but non-limiting embodiment, the methods described herein comprise obtaining sequence information for the nucleic acids in the test sample, e.g., cfDNA in a maternal test sample, cfDNA or cellular DNA in a subject being screened for a cancer, and the like, using the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode waveguide detectors (ZMW detectors) that obtain sequence information while phospholinked nucleotides are being incorporated into the growing primer strand. A ZMW detector comprises a confinement structure that enables observation of incorporation of a single nucleotide by DNA polymerase against a background of fluorescent nucleotides that rapidly diffuse in an out of the ZMW (e.g., in microseconds). It typically takes several milliseconds to incorporate a nucleotide into a growing strand. During this time, the fluorescent label is excited and produces a fluorescent signal, and the fluorescent tag is cleaved off. Measurement of the corresponding fluorescence of the dye indicates which base was incorporated. The process is repeated to provide a sequence.

In another illustrative, but non-limiting embodiment, the methods described herein comprise obtaining sequence information for the nucleic acids in the test sample, e.g., cfDNA in a maternal test sample, cfDNA or cellular DNA in a subject being screened for a cancer, and the like, using nanopore sequencing (e.g. as described in Soni G V and Meller A. Clin Chem 53: 1996-2001 [2007]). Nanopore sequencing DNA analysis techniques are developed by a number of companies, including, for example, Oxford Nanopore Technologies (Oxford, United Kingdom), Sequenom, NABsys, and the like. Nanopore sequencing is a single-molecule sequencing technology whereby a single molecule of DNA is sequenced directly as it passes through a nanopore. A nanopore is a small hole, typically of the order of 1 nanometer in diameter. Immersion of a nanopore in a conducting fluid and application of a potential (voltage) across it results in a slight electrical current due to conduction of ions through the nanopore. The amount of current that flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore provides a read of the DNA sequence.

In another illustrative, but non-limiting embodiment, the methods described herein comprises obtaining sequence information for the nucleic acids in the test sample, e.g., cfDNA in a maternal test sample, cfDNA or cellular DNA in a subject being screened for a cancer, and the like, using the chemical-sensitive field effect transistor (chemFET) array (e.g., as described in U.S. Patent Application Publication No. 2009/0026082). In one example of this technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned as a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In another embodiment, the present method comprises obtaining sequence information for the nucleic acids in the test sample, e.g., cfDNA in a maternal test sample, using transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In another embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be detected by Ion Torrent's ion sensor. The sequencer-essentially the world's smallest solid-state pH meter-calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct detection allows recordation of nucleotide incorporation in seconds.

In another embodiment, the present method comprises obtaining sequence information for the nucleic acids in the test sample, e.g., cfDNA in a maternal test sample, using sequencing by hybridization. Sequencing-by-hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be determined and used to identify the plurality of polynucleotide sequences within the sample.

In some embodiments of the methods described herein, the mapped sequence tags comprise sequence reads of about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the mapped sequence tags comprise sequence reads that are 36 bp. Mapping of the sequence tags is achieved by comparing the sequence of the tag with the sequence of the reference to determine the chromosomal origin of the sequenced nucleic acid (e.g. cfDNA) molecule, and specific genetic sequence information is not needed. A small degree of mismatch (0-2 mismatches per sequence tag) may be allowed to account for minor polymorphisms that may exist between the reference genome and the genomes in the mixed sample.

A plurality of sequence tags are typically obtained per sample. In some embodiments, at least about $3 \times 10^6$ sequence tags, at least about $5 \times 10^6$ sequence tags, at least about $8 \times 10^6$ sequence tags, at least about $10 \times 10^6$ sequence tags, at least about $15 \times 10^6$ sequence tags, at least about $20 \times 10^6$ sequence tags, at least about $30 \times 10^6$ sequence tags, at least about $40 \times 10^6$ sequence tags, or at least about $50 \times 10^6$ sequence tags comprising between 20 and 40 bp reads, e.g., 36 bp, are obtained from mapping the reads to the reference genome per sample. In one embodiment, all the sequence reads are mapped to all regions of the reference genome. In one embodiment, the tags that have been mapped to all regions, e.g., all chromosomes, of the reference genome are analyzed, and the SNV or CNV, in the cfDNA sample is determined.

The accuracy required for correctly determining whether a SNV or CNV is present or absent in a sample, is predicated on the variation of the number of sequence tags that map to the reference genome among samples within a sequencing run (inter-chromosomal variability), and the variation of the number of sequence tags that map to the reference genome in different sequencing runs (inter-sequencing variability). For example, the variations can be particularly pronounced for tags that map to GC-rich or GC-poor reference sequences. Other variations can result from using different protocols for the extraction and purification of the nucleic acids, the preparation of the sequencing libraries, and the use of different sequencing platforms. The present method uses sequence doses (chromosome doses, or segment doses) based on the knowledge of normalizing sequences (normalizing chromosome sequences or normalizing segment sequences), to intrinsically account for the accrued variability stemming from interchromosomal (intra-run), and inter-sequencing (inter-run) and platform-dependent variability. Chromosome doses are based on the knowledge of a normalizing chromosome sequence, which can be composed of a single chromosome, or of two or more chromosomes selected from chromosomes 1-22, X, and Y. Alternatively, normalizing chromosome sequences can be composed of a single chromosome segment, or of two or more segments of one chromosome or of two or more chromosomes. Segment doses are based on the knowledge of a normalizing segment sequence, which can be composed of a single segment of any one chromosome, or of two or more segments of any two or more of chromosomes 1-22, X, and Y.

Apparatus and System for Determining Variant of Interest

Analysis of the sequencing data and the diagnosis derived therefrom are typically performed using various computer executed algorithms and programs. Therefore, certain embodiments employ processes involving data stored in or transferred through one or more computer systems or other processing systems. Embodiments disclosed herein also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing)

and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In various embodiments, the data or information employed in the disclosed methods and apparatus is provided in an electronic format. Such data or information may include reads and tags derived from a nucleic acid sample, counts or densities of such tags that align with particular regions of a reference sequence (e.g., that align to a chromosome or chromosome segment), reference sequences (including reference sequences providing solely or primarily polymorphisms), chromosome and segment doses, calls such as SNV or aneuploidy calls, normalized chromosome and segment values, pairs of chromosomes or segments and corresponding normalizing chromosomes or segments, counseling recommendations, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

One embodiment provides a computer program product for generating an output indicating the presence or absence of an SNV or aneuploidy associated with a cancer, in a test sample. The computer product may contain instructions for performing any one or more of the above-described methods for determining a chromosomal anomaly. As explained, the computer product may include a non-transitory and/or tangible computer readable medium having a computer executable or compilable logic (e.g., instructions) recorded thereon for enabling a processor to determine if a SNV or CNV call should be made. In one example, the computer product comprises a computer readable medium having a computer executable or compilable logic (e.g., instructions) recorded thereon for enabling a processor to diagnose an SNV or a CNV.

The sequence information from the sample under consideration may be mapped to chromosome reference sequences to identify a number of sequence tags for each of any one or more chromosomes of interest and to identify a number of sequence tags for a normalizing segment sequence for each of said any one or more chromosomes of interest. In various embodiments, the reference sequences are stored in a database such as a relational or object database, for example.

It should be understood that it is not practical, or even possible in most cases, for an unaided human being to perform the computational operations of the methods disclosed herein. For example, mapping a single 30 bp read from a sample to any one of the human chromosomes might require years of effort without the assistance of a computational apparatus. Of course, the problem is compounded because reliable SNV and CNV calls generally require mapping thousands (e.g., at least about 10,000) or even millions of reads to one or more chromosomes.

The methods disclosed herein can be performed using a system for evaluation of copy number of a genetic sequence of interest in a test sample. The system comprising: (a) a sequencer for receiving nucleic acids from the test sample providing nucleic acid sequence information from the sample; (b) a processor; and (c) one or more computer-readable storage media having stored thereon instructions for execution on said processor to carry out a method for identifying any SNV or CNV.

In some embodiments, the methods are instructed by a computer-readable medium having stored thereon computer-readable instructions for carrying out a method for identifying any SNV or CNV. Thus one embodiment provides a computer program product comprising one or more computer-readable non-transitory storage media having stored thereon computer-executable instructions that, when executed by one or more processors of a computer system, cause the computer system to implement a method for evaluation of copy number of a sequence of interest in a test sample comprising normal and tumor cell-free nucleic acids. The method includes: (a) retrieving, by the one or more processors, sequence reads and fragment sizes of cfDNA fragments obtained from a test sample; (b) assigning, by the one or more processors, the cfDNA fragments into a plurality of bins representing different fragment sizes; and (c) determining, using the sequence reads and by the one or more processors, an allele frequency of the variant of interest in a prioritized set of bins selected from the plurality of bins, wherein the prioritized set of bins was selected to (i) limit a probability that a quantity of the variant of interest in the prioritized set of bins is below a limit of detection and (ii) increase a probability that a quantity of the variant of interest in the prioritized set of bins is higher than in all bins of the plurality of bins.

In some embodiments, the instructions may further include automatically recording information pertinent to the method such as chromosome doses and the presence or absence of a SNV or a CNV in a patient medical record for a human subject providing the maternal test sample. The patient medical record may be maintained by, for example, a laboratory, physician's office, a hospital, a health maintenance organization, an insurance company, or a personal medical record website. Further, based on the results of the processor-implemented analysis, the method may further involve prescribing, initiating, and/or altering treatment of a human subject from whom the maternal test sample was taken. This may involve performing one or more additional tests or analyses on additional samples taken from the subject.

Disclosed methods can also be performed using a computer processing system which is adapted or configured to perform a method for identifying any SNV or CNV. One embodiment provides a computer processing system which is adapted or configured to perform a method as described herein. In one embodiment, the apparatus comprises a sequencing device adapted or configured for sequencing at least a portion of the nucleic acid molecules in a sample to obtain the type of sequence information described elsewhere herein. The apparatus may also include components for processing the sample. Such components are described elsewhere herein.

Sequence or other data, can be input into a computer or stored on a computer readable medium either directly or indirectly. In one embodiment, a computer system is directly coupled to a sequencing device that reads and/or analyzes sequences of nucleic acids from samples. Sequences or other information from such tools are provided via interface in the computer system. Alternatively, the sequences processed by system are provided from a sequence storage source such as a database or other repository. Once available to the processing apparatus, a memory device or mass storage device buffers or stores, at least temporarily, sequences of the nucleic acids. In addition, the memory device may store tag counts for various chromosomes or genomes, etc. The memory may also store various routines and/or programs for analyzing the presenting the sequence or mapped data. Such programs/routines may include programs for performing statistical analyses, etc.

In one example, a user provides a sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. The computer may be connected to the internet which is used to transmit data to a handheld device utilized by a remote user (e.g., a physician, scientist or analyst). It is understood that the data can be stored and/or analyzed prior to transmittal. In some embodiments, raw data is collected and sent to a remote user or apparatus that will analyze and/or store the data. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to a building, city, state, country or continent.

In some embodiments, the methods also include collecting data regarding a plurality of polynucleotide sequences (e.g., reads, tags and/or reference chromosome sequences) and sending the data to a computer or other computational system. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet. At the remote location various operations can be performed on the transmitted data as described below.

Among the types of electronically formatted data that may be stored, transmitted, analyzed, and/or manipulated in systems, apparatus, and methods disclosed herein are the following:

Reads obtained by sequencing nucleic acids in a test sample

Tags obtained by aligning reads to a reference genome or other reference sequence or sequences The reference genome or sequence Sequence tag density—Counts or numbers of tags for each of two or more regions (typically chromosomes or chromosome segments) of a reference genome or other reference sequences Identities of normalizing chromosomes or chromosome segments for particular chromosomes or chromosome segments of interest Doses for chromosomes or chromosome segments (or other regions) obtained from chromosomes or segments of interest and corresponding normalizing chromosomes or segments Thresholds for calling chromosome doses as either affected, non-affected, or no call The actual calls of chromosome doses Diagnoses (clinical condition associated with the calls)

Recommendations for further tests derived from the calls and/or diagnoses

Treatment and/or monitoring plans derived from the calls and/or diagnoses

These various types of data may be obtained, stored transmitted, analyzed, and/or manipulated at one or more locations using distinct apparatus. The processing options span a wide spectrum. At one end of the spectrum, all or much of this information is stored and used at the location where the test sample is processed, e.g., a doctor's office or other clinical setting. In other extreme, the sample is obtained at one location, it is processed and optionally sequenced at a different location, reads are aligned and calls are made at one or more different locations, and diagnoses, recommendations, and/or plans are prepared at still another location (which may be a location where the sample was obtained).

In various embodiments, the reads are generated with the sequencing apparatus and then transmitted to a remote site where they are processed to produce calls. At this remote location, as an example, the reads are aligned to a reference sequence to produce tags, which are counted and assigned to chromosomes or segments of interest. Also at the remote location, the counts are converted to doses using associated normalizing chromosomes or segments. Still further, at the remote location, the doses are used to generate calls.

Among the processing operations that may be employed at distinct locations are the following:

Sample collection

Sample processing preliminary to sequencing

Sequencing

Analyzing sequence data and deriving SNV or CNV calls

Diagnosis

Reporting a diagnosis and/or a call to patient or health care provider

Developing a plan for further treatment, testing, and/or monitoring

Executing the plan

Counseling

Any one or more of these operations may be automated as described elsewhere herein. Typically, the sequencing and the analyzing of sequence data and deriving SNV or CNV calls will be performed computationally. The other operations may be performed manually or automatically.

Examples of locations where sample collection may be performed include health practitioners' offices, clinics, patients' homes (where a sample collection tool or kit is provided), and mobile health care vehicles. Examples of locations where sample processing prior to sequencing may be performed include health practitioners' offices, clinics, patients' homes (where a sample processing apparatus or kit is provided), mobile health care vehicles, and facilities of SNV or CNV analysis providers. Examples of locations where sequencing may be performed include health practitioners' offices, clinics, health practitioners' offices, clinics, patients' homes (where a sample sequencing apparatus and/or kit is provided), mobile health care vehicles, and facilities of SNV or CNV analysis providers. The location where the sequencing takes place may be provided with a dedicated network connection for transmitting sequence data (typically reads) in an electronic format. Such connection may be wired or wireless and have and may be configured to send the data to a site where the data can be processed and/or aggregated prior to transmission to a processing site. Data aggregators can be maintained by health organizations such as Health Maintenance Organizations (HMOs).

The analyzing and/or deriving operations may be performed at any of the foregoing locations or alternatively at a further remote site dedicated to computation and/or the service of analyzing nucleic acid sequence data. Such locations include for example, clusters such as general purpose server farms, the facilities of an SNV or CNV analysis service business, and the like. In some embodiments, the computational apparatus employed to perform the analysis is leased or rented. The computational resources may be part of an internet accessible collection of processors such as processing resources colloquially known as the cloud. In some cases, the computations are performed by a parallel or massively parallel group of processors that are affiliated or unaffiliated with one another. The processing may be accomplished using distributed processing such as cluster computing, grid computing, and the like. In such embodiments, a cluster or grid of computational resources collective form a super virtual computer composed of multiple processors or computers acting together to perform the analysis and/or derivation described herein. These technologies as well as more conventional supercomputers may be employed to process sequence data as described herein. Each is a form of parallel computing that relies on processors or computers. In the case of grid computing these processors (often whole computers) are connected by a network (private, public, or the Internet) by a conventional network protocol such as Ethernet. By contrast, a supercomputer has many processors connected by a local high-speed computer bus.

In certain embodiments, the diagnosis is generated at the same location as the analyzing operation. In other embodiments, it is performed at a different location. In some examples, reporting the diagnosis is performed at the location where the sample was taken, although this need not be the case. Examples of locations where the diagnosis can be generated or reported and/or where developing a plan is performed include health practitioners' offices, clinics, internet sites accessible by computers, and handheld devices such as cell phones, tablets, smart phones, etc. having a wired or wireless connection to a network. Examples of locations where counseling is performed include health practitioners' offices, clinics, internet sites accessible by computers, handheld devices, etc.

In some embodiments, the sample collection, sample processing, and sequencing operations are performed at a first location and the analyzing and deriving operation is performed at a second location. However, in some cases, the sample collection is collected at one location (e.g., a health practitioner's office or clinic) and the sample processing and sequencing is performed at a different location that is optionally the same location where the analyzing and deriving take place.

In various embodiments, a sequence of the above-listed operations may be triggered by a user or entity initiating sample collection, sample processing and/or sequencing. After one or more these operations have begun execution the other operations may naturally follow. For example, the sequencing operation may cause reads to be automatically collected and sent to a processing apparatus which then conducts, often automatically and possibly without further user intervention, the sequence analysis and derivation of SNV or CNV operation. In some implementations, the result of this processing operation is then automatically delivered, possibly with reformatting as a diagnosis, to a system component or entity that processes reports the information to a health professional and/or patient. As explained such information can also be automatically processed to produce a treatment, testing, and/or monitoring plan, possibly along with counseling information. Thus, initiating an early stage operation can trigger an end to end sequence in which the health professional, patient or other concerned party is provided with a diagnosis, a plan, counseling and/or other information useful for acting on a physical condition. This is accomplished even though parts of the overall system are physically separated and possibly remote from the location of, e.g., the sample and sequence apparatus.

Figure 4:
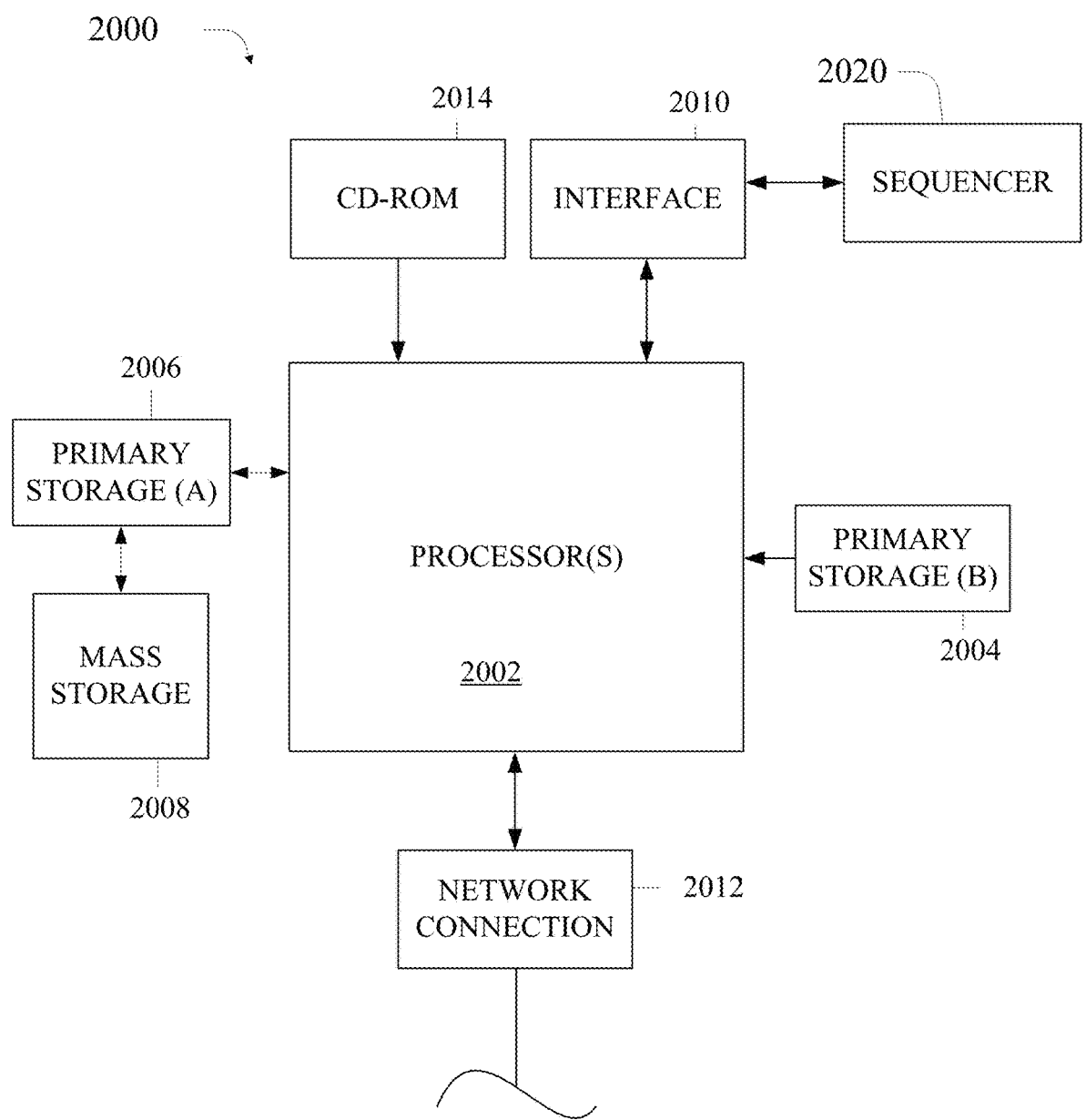
FIG. 4 illustrates a typical computer system according to certain embodiments.

FIG. 4 illustrates, in simple block format, a typical computer system that, when appropriately configured or designed, can serve as a computational apparatus according to certain embodiments. The computer system 2000 includes any number of processors 2002 (also referred to as central processing units, or CPUs) that are coupled to storage devices including primary storage 2006 (typically a random access memory, or RAM), primary storage 2004 (typically a read only memory, or ROM). CPU 2002 may be of various types including microcontrollers and microprocessors such as programmable devices (e.g., CPLDs and FPGAs) and non-programmable devices such as gate array ASICs or general-purpose microprocessors. In the depicted embodiment, primary storage 2004 acts to transfer data and instructions uni-directionally to the CPU and primary storage 2006 is used typically to transfer data and instructions in a bi-directional manner. Both of these primary storage devices may include any suitable computer-readable media such as those described above. A mass storage device 2008 is also coupled bi-directionally to primary storage 2006 and provides additional data storage capacity and may include any of the computer-readable media described above. Mass storage device 2008 may be used to store programs, data and the like and is typically a secondary storage medium such as a hard disk. Frequently, such programs, data and the like are temporarily copied to primary memory 2006 for execution on CPU 2002. It will be appreciated that the information retained within the mass storage device 2008, may, in appropriate cases, be incorporated in standard fashion as part of primary storage 2004. A specific mass storage device such as a CD-ROM 2014 may also pass data uni-directionally to the CPU or primary storage.

CPU 2002 is also coupled to an interface 2010 that connects to one or more input/output devices such as such as a nucleic acid sequencer (2020), video monitors, track balls, mice, keyboards, microphones, touch-sensitive displays, transducer card readers, magnetic or paper tape readers, tablets, styluses, voice or handwriting recognition peripherals, USB ports, or other well-known input devices such as, of course, other computers. Finally, CPU 2002 optionally may be coupled to an external device such as a database or a computer or telecommunications network using an external connection as shown generally at 2012. With such a connection, it is contemplated that the CPU might receive information from the network, or might output information to the network in the course of performing the method steps described herein. In some implementations, a nucleic acid sequencer (2020) may be communicatively linked to the CPU 2002 via the network connection 2012 instead of or in addition to via the interface 2010.

In one embodiment, a system such as computer system 2000 is used as a data import, data correlation, and querying system capable of performing some or all of the tasks described herein. Information and programs, including data files can be provided via a network connection 2012 for access or downloading by a researcher. Alternatively, such information, programs and files can be provided to the researcher on a storage device.

In a specific embodiment, the computer system 2000 is directly coupled to a data acquisition system such as a microarray, high-throughput screening system, or a nucleic acid sequencer (2020) that captures data from samples. Data from such systems are provided via interface 2010 for analysis by system 2000. Alternatively, the data processed by system 2000 are provided from a data storage source such as a database or other repository of relevant data. Once in apparatus 2000, a memory device such as primary storage 2006 or mass storage 2008 buffers or stores, at least temporarily, relevant data. The memory may also store various routines and/or programs for importing, analyzing and presenting the data, including sequence reads, UMIs, codes for determining sequence reads, collapsing sequence reads and correcting errors in reads, etc.

In certain embodiments, the computers used herein may include a user terminal, which may be any type of computer (e.g., desktop, laptop, tablet, etc.), media computing platforms (e.g., cable, satellite set top boxes, digital video recorders, etc.), handheld computing devices (e.g., PDAs, e-mail clients, etc.), cell phones or any other type of computing or communication platforms.

In certain embodiments, the computers used herein may also include a server system in communication with a user terminal, which server system may include a server device or decentralized server devices, and may include mainframe computers, mini computers, super computers, personal computers, or combinations thereof. A plurality of server systems may also be used without departing from the scope of the present invention. User terminals and a server system may communicate with each other through a network. The network may comprise, e.g., wired networks such as LANs (local area networks), WANs (wide area networks), MANs (metropolitan area networks), ISDNs (Intergrated Service Digital Networks), etc. as well as wireless networks such as wireless LANs, CDMA, Bluetooth, and satellite communication networks, etc. without limiting the scope of the present invention.

Figure 5:
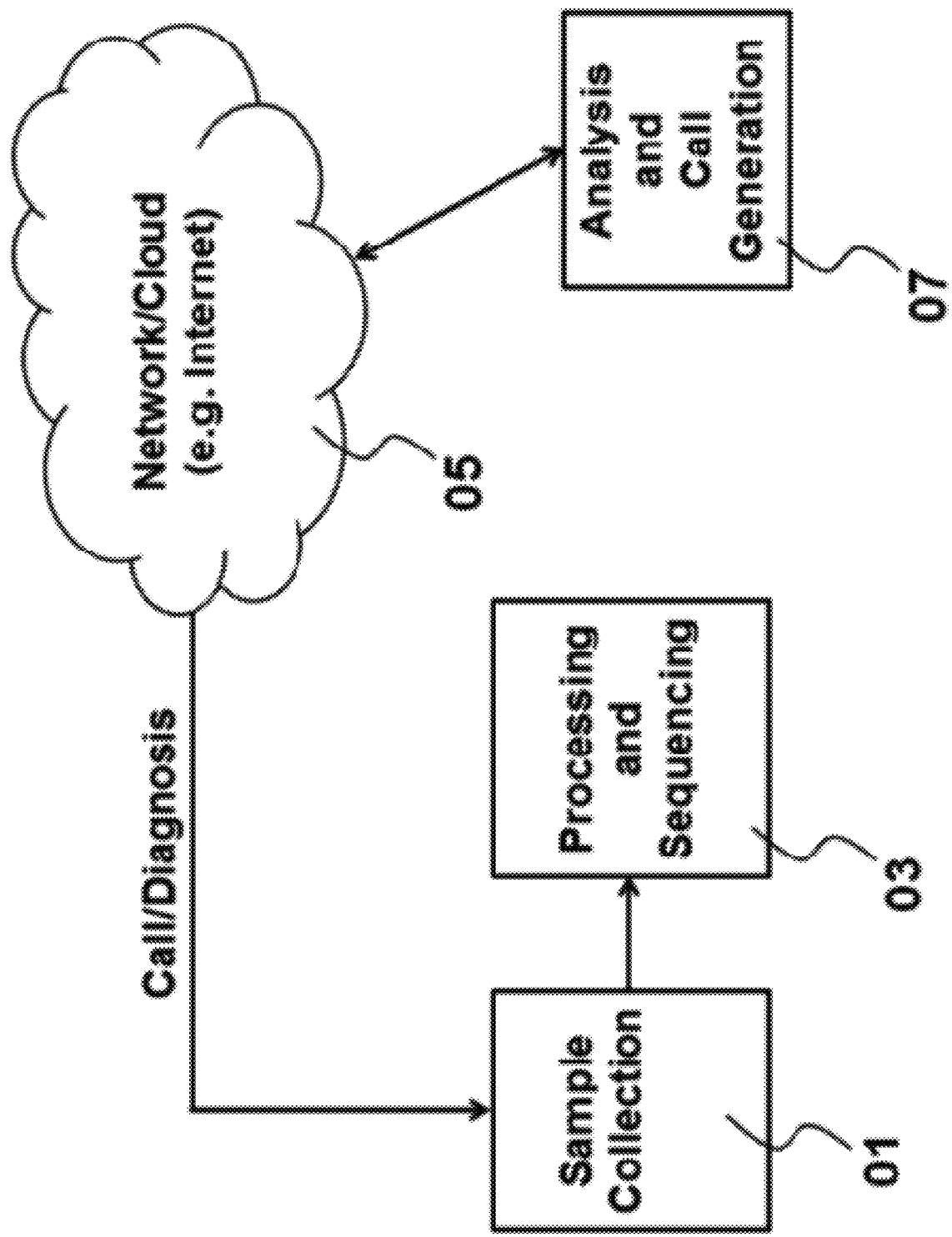
FIG. 5 is a block diagram of a dispersed system for processing a test sample and making a diagnosis.

FIG. 5 shows one implementation of a dispersed system for producing a call or diagnosis from a test sample. A sample collection location 01 is used for obtaining a test sample from a patient such as a pregnant female or a putative cancer patient. The samples then provided to a processing and sequencing location 03 where the test sample may be processed and sequenced as described above. Location 03 includes apparatus for processing the sample as well as apparatus for sequencing the processed sample. The result of the sequencing, as described elsewhere herein, is a collection of reads which are typically provided in an electronic format and provided to a network such as the Internet, which is indicated by reference number 05 in FIG. 5.

The sequence data is provided to a remote location 07 where analysis and call generation are performed. This location may include one or more powerful computational devices such as computers or processors. After the computational resources at location 07 have completed their analysis and generated a call from the sequence information received, the call is relayed back to the network 05. In some implementations, not only is a call generated at location 07 but an associated diagnosis is also generated. The call and or diagnosis are then transmitted across the network and back to the sample collection location 01 as illustrated in FIG. 5. As explained, this is simply one of many variations on how the various operations associated with generating a call or diagnosis may be divided among various locations. One common variant involves providing sample collection and processing and sequencing in a single location. Another variation involves providing processing and sequencing at the same location as analysis and call generation.

Figure 6:
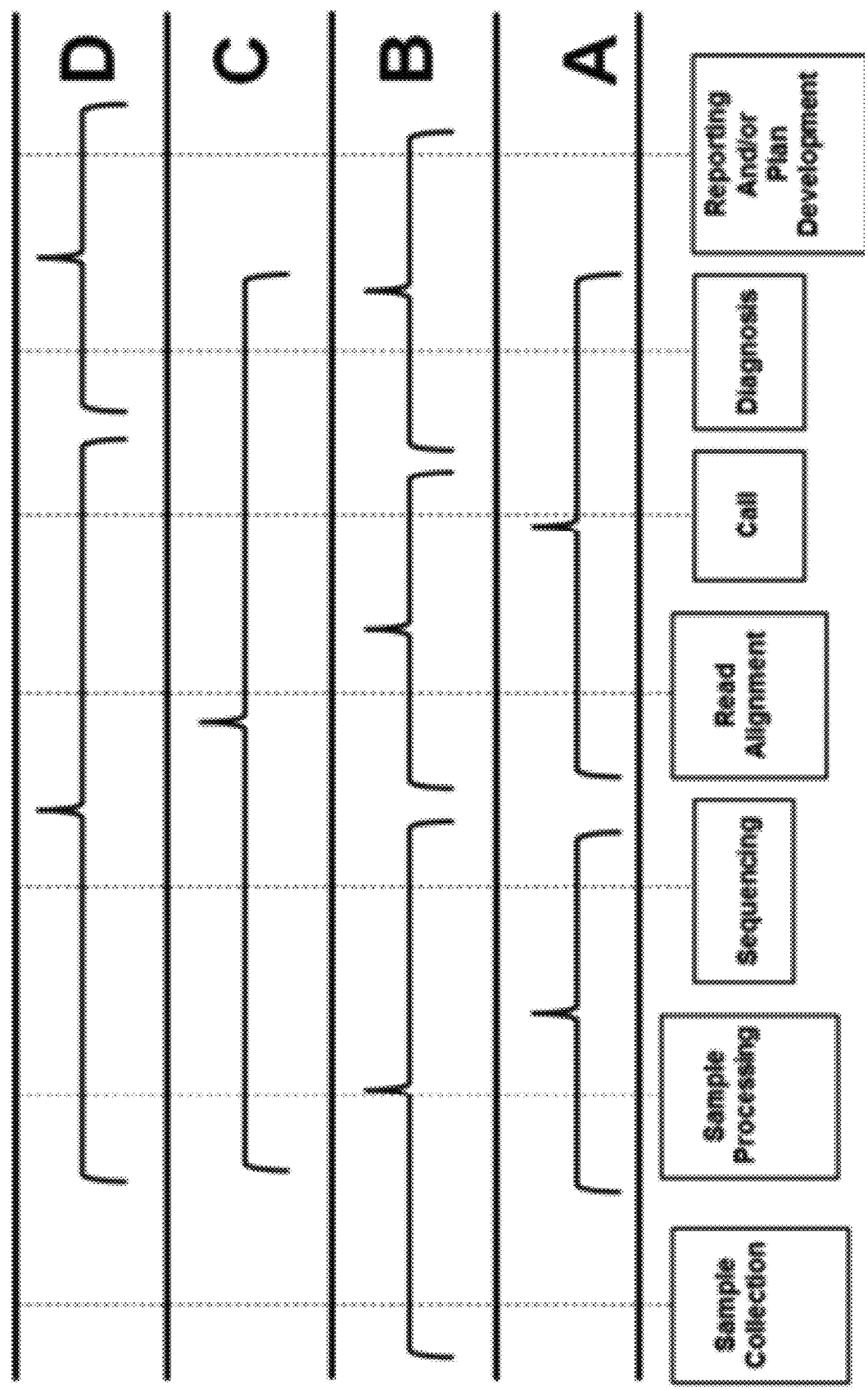
FIG. 6 schematically illustrates how different operations in processing test samples may be grouped to be handled by different elements of a system.

FIG. 6 elaborates on the options for performing various operations at distinct locations. In the most granular sense depicted in FIG. 6, each of the following operations is performed at a separate location: sample collection, sample processing, sequencing, read alignment, calling, diagnosis, and reporting and/or plan development.

In one embodiment that aggregates some of these operations, sample processing and sequencing are performed in one location and read alignment, calling, and diagnosis are performed at a separate location. See the portion of FIG. 6 identified by reference character A. In another implementation, which is identified by character B in FIG. 6, sample collection, sample processing, and sequencing are all performed at the same location. In this implementation, read alignment and calling are performed in a second location. Finally, diagnosis and reporting and/or plan development are performed in a third location. In the implementation depicted by character C in FIG. 6, sample collection is performed at a first location, sample processing, sequencing, read alignment, calling, and diagnosis are all performed together at a second location, and reporting and/or plan development are performed at a third location. Finally, in the implementation labeled D in FIG. 6, sample collection is performed at a first location, sample processing, sequencing, read alignment, and calling are all performed at a second location, and diagnosis and reporting and/or plan management are performed at a third location.

One embodiment provides a system for analyzing cell-free DNA (cfDNA) for simple nucleotide variants associated with tumors, the system including a sequencer for receiving a nucleic acid sample and providing nucleic acid sequence information from the nucleic acid sample; a processor; and a machine readable storage medium comprising codes for execution on said processor, the codes including: (a) code for retrieving sequence reads and fragment sizes of cfDNA fragments obtained from a test sample; (b) code for assigning the cfDNA fragments into a plurality of bins representing different fragment sizes; and (c) code for determining, using the sequence reads, an allele frequency of the variant of interest in a prioritized set of bins selected from the plurality of bins, wherein the prioritized set of bins was selected to (i) limit a probability that a quantity of the variant of interest in the prioritized set of bins is below a limit of detection and (ii) increase a probability that a quantity of the variant of interest in the prioritized set of bins is higher than in all bins of the plurality of bins.

In some embodiments of any of the systems provided herein, the sequencer is configured to perform next generation sequencing (NGS). In some embodiments, the sequencer is configured to perform massively parallel sequencing using sequencing-by-synthesis with reversible dye terminators. In other embodiments, the sequencer is configured to perform sequencing-by-ligation. In yet other embodiments, the sequencer is configured to perform single molecule sequencing.

EXPERIMENTAL

Example 1

This example uses simulated data to illustrate advantages provided by methods for analyzing cell-free DNA fragments to determine a variant of interest using a prioritized bin set. This example shows that some implementations can provide improved signal level for detecting the variant of interest (e.g., a variant associated with a tumor).

Simulation data were generated for four different scenarios, each having different tumor fractions, allele frequencies in tumor cells, and allele frequency in a plasma sample. The plasma sample includes cfDNA fragments derived from tumor cells and from healthy cells. The scenarios also have different sequencing depths.

Table 1 shows the parameter values for the four different scenarios. Scenario A was provided to simulate a sample that had a tumor fraction ($f_{tumor}$) of 0.01, an allele frequency in tumor cells ($AF_{tumor}$) of 0.5, an allele frequency in plasma ($AF_{plasma}$) of 0.005, and processed by a sequencing depth (DP) of 5000×. Scenario A was provided to simulate a clinical condition where a cancer is in an early stage and the tumor fraction is very low.

Scenario B had a tumor fraction of 0.2, an allele frequency of tumor cells of 0.5, and a plasma allele frequency of 0.1. The sequencing depth for scenario B is 1000. Scenario B was provided to simulate a clinical condition at a later stage of tumor when the tumor burden is high and the changes of tumor may be of interest for monitoring tumor development.

Scenario C had a tumor fraction of 0.2, an allele frequency of tumor cells of 0.02, and a plasma allele frequency of 0.004. The sequencing depth is 5000. Scenario C was provided to simulate a treatment resistant mutation in metastasis, where the tumor fraction was high but the allele frequency in the tumor cells was low.

Scenario D had a tumor fraction of 0.1, an allele frequency of tumor cells of 0.05, and a plasma allele frequency of 0.005. The sequencing depth for the scenario is 5000. Scenario D is designed to simulate sub-clonal mutations in a primary cancer, in which the tumor fraction was at an intermediate level, and the tumor cell allele frequency is relatively low.

Figure 7A:
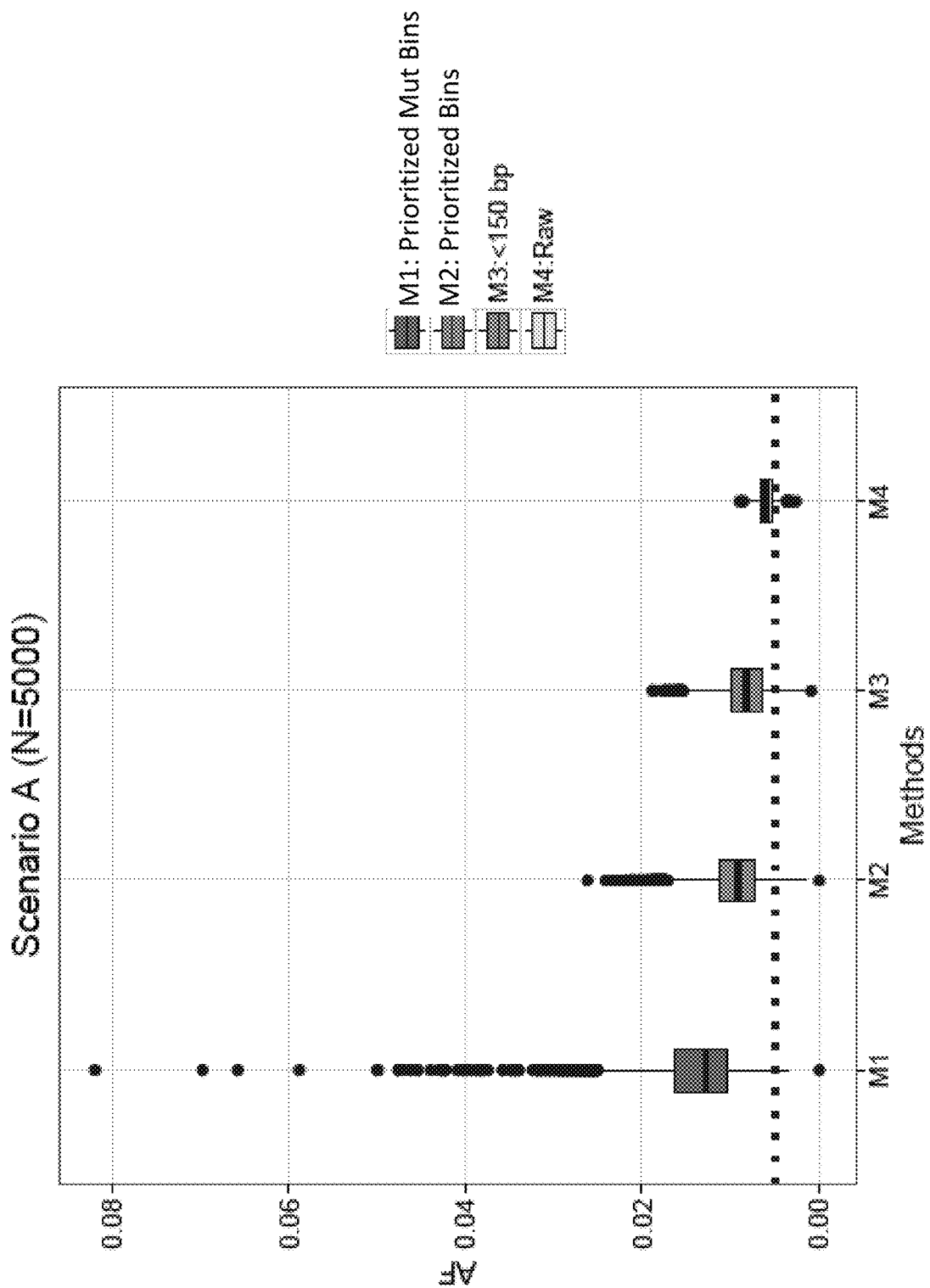
FIGS. 7A-7D show the allele frequencies of the variant of interest using different sets of fragment size bins, one figure for each of four scenarios.

FIGS. 7A-7D show the allele frequencies of the variant of interest using different sets of fragment size bins, one figure for each of scenarios A-D. FIG. 7A shows the data for scenario A. The allele frequencies for four sets of bins are shown as M1-M4 whisker-boxes. Box M1 shows allele frequency data obtained using a prioritized set of bins. The prioritized set is selected to increase the probability that the variant of interest has a higher allele frequency in the prioritized set than in all bins of the plurality of bins (or the $AF_{plasma}$ mentioned above) and to limit the probability that the variant of interest has an allele frequency below a limit of detection in the prioritized set of bins. Bins that do not include any fragments harboring the variant of interest are excluded. Namely, the bins used to obtain the allele frequency are prioritized and mutant containing.

The data in box M2 are obtain in a manner similar to M1, except that the prioritized bin set includes all bins in a candidate set, namely, including both bins containing fragments harboring the variant of interest and bins that do not contain any fragments harboring the variant of interest. Namely, the bins used to obtain the allele frequency are prioritized.

Box M3 shows allele frequency data for bins containing fragments shorter than 150 base pairs.

Box M4 shows allele frequency data for all bins without prioritization. This allele frequency is also referred to as the plasma allele frequency or raw allele frequency.

As shown in FIG. 7A, the allele frequency of M1 (prioritized and mutant containing) is higher than that of M3 and M4. Similarly, the allele frequency of M2 (prioritized) is also higher than M3 and M4. The differences are statistically significant. FIG. 7A illustrates that using prioritized bins that contain the variant of interest can help to increase the signal level for detecting the variant of interest in scenario A, where a cancer is at an early stage, and the tumor fraction is very low.

Figure 7B:
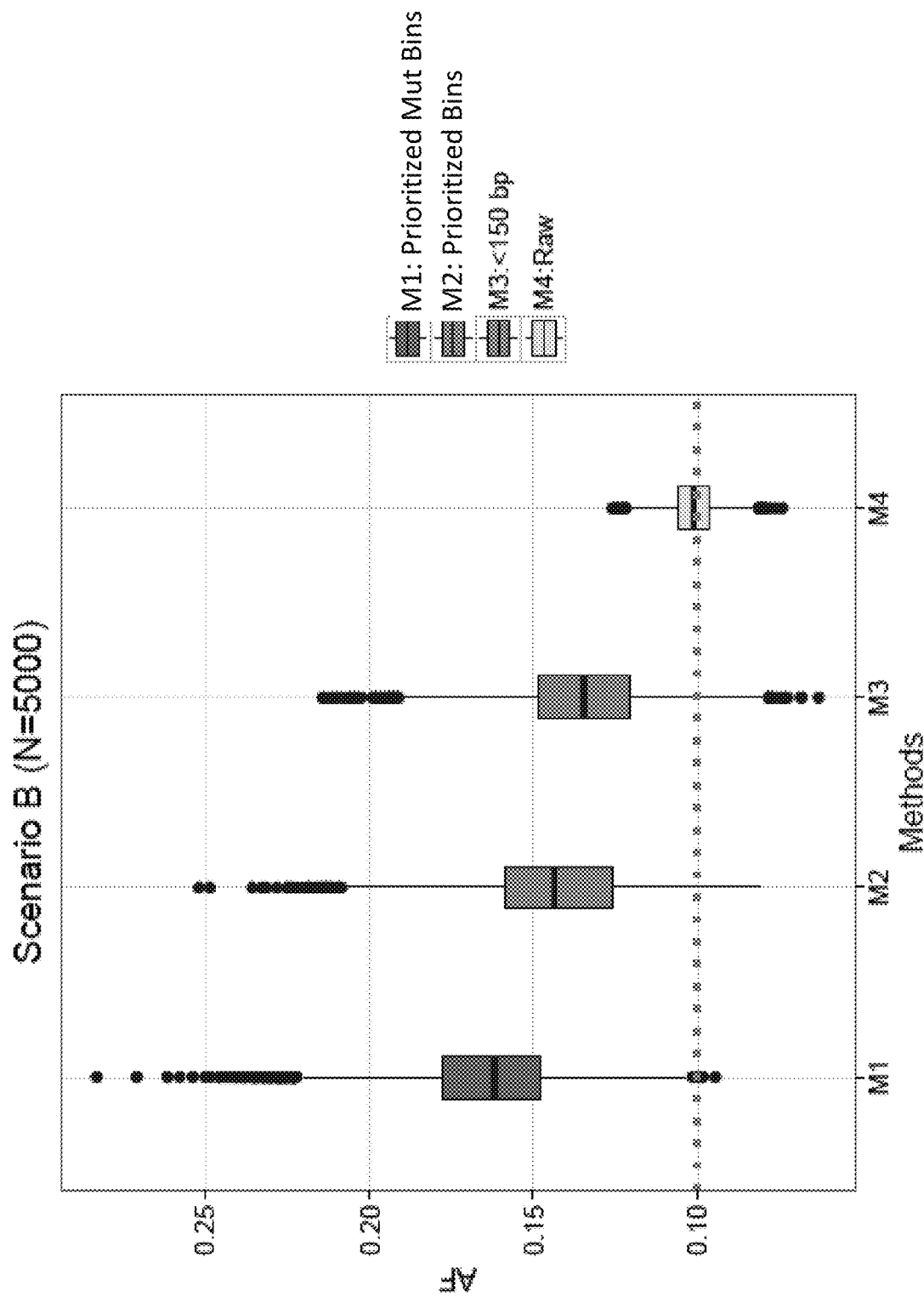
Figure 7C:
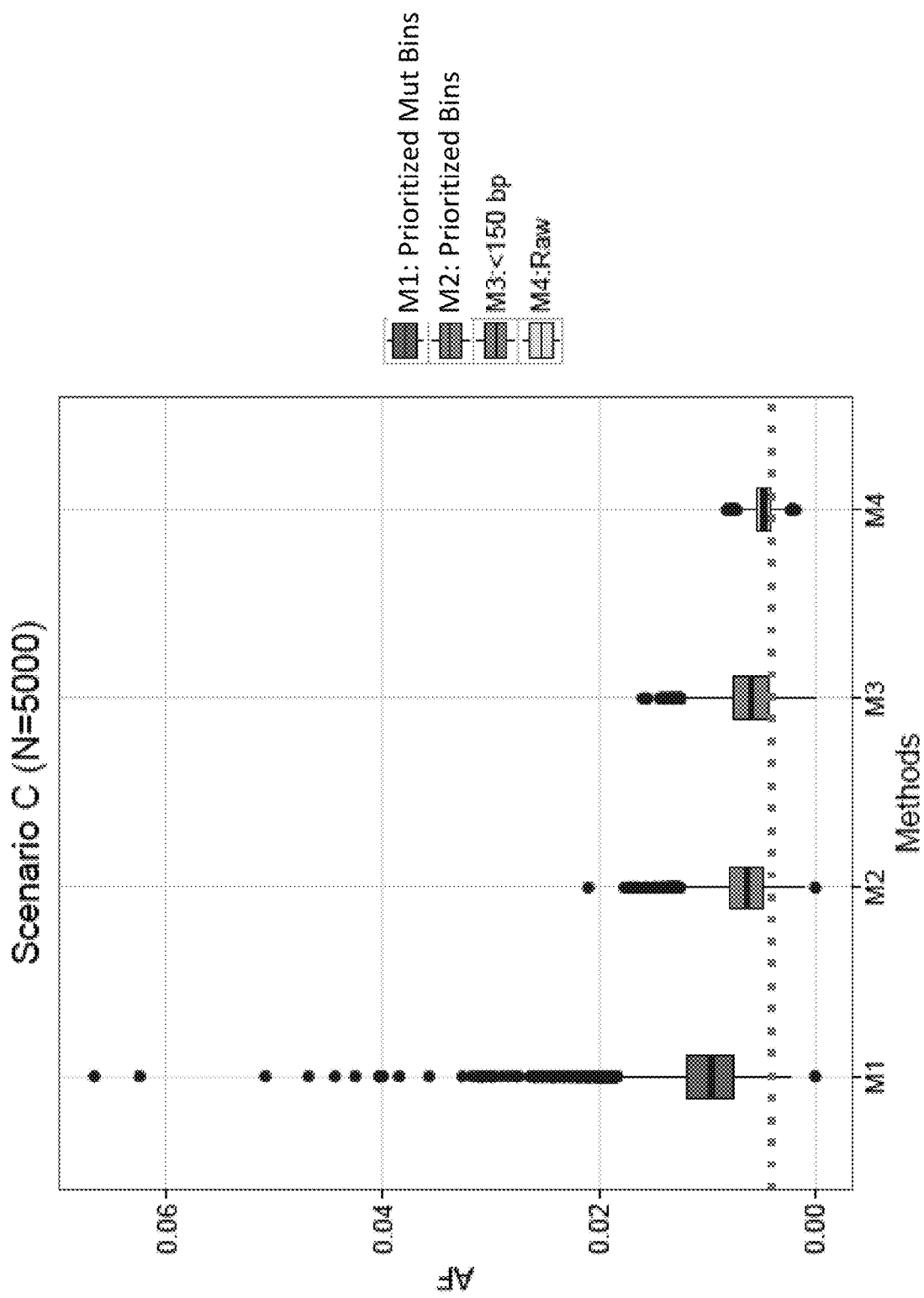
Figure 7D:
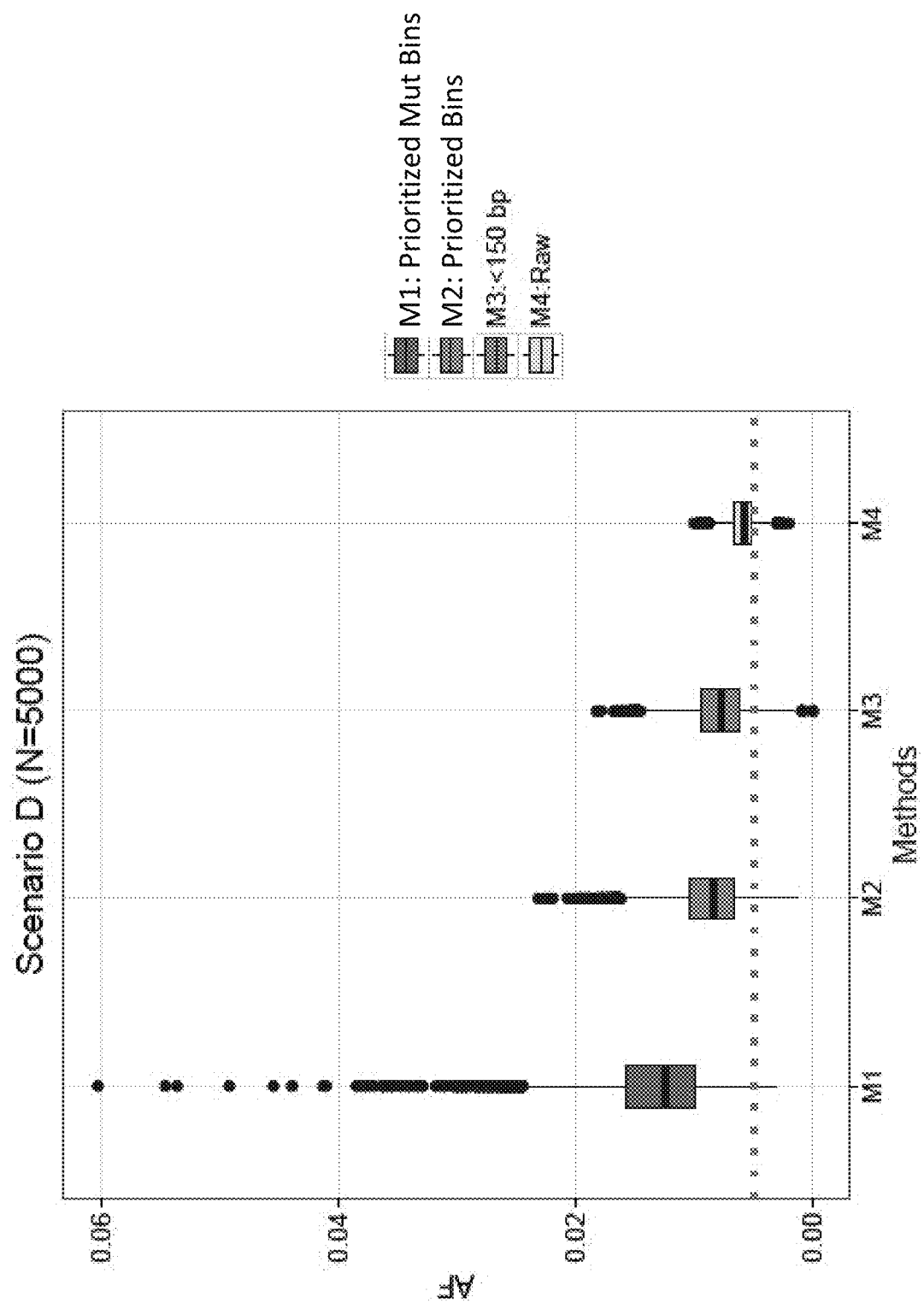

The data pattern observed above in FIG. 7A also appears in FIG. 7B-7D. Therefore, using prioritized bins obtained by methods described herein, one can boost signal level for detecting a tumor variant in various clinical conditions such as when the tumor burden is high in scenario B, when the tumor allele frequency is low in a metastasis state of tumor mutation that is treatment resistant (scenario C), and when the tumor is associated with a sub-clonal mutation having a relatively low tumor allele frequency and intermediate tumor fraction (scenario D).

Using the two prioritized sets of bins can not only increase the sensitivity for detecting the variant of interest, but can also potentially increase or maintain the selectivity for detecting the variant of interest. Table 2 shows the selectivity values for the four different types of bins used to analyze the cfDNA data in four rows. Selectivity=true negative/(true negative+false negative). The table shows data for three different tumor fractions in three columns (0.01, 0.0 0.1, and 0.2). A consistent data pattern among the four different bins emerged across different tumor fractions. Specifically, the analysis using all the bins has a high selectivity at 99.7%. The selectivity level is reduced to 94.6% when only bins containing fragments shorter than the 150 bp are used. The selectivity of the analysis using prioritized bins and prioritized and mutant bins remains at 99.7%. The same selectivity patterns across the four different bin sets remain the same for higher tumor fractions at 0.1 and 0.2. Therefore, it is apparent from the data in Table 2 that using prioritized bins can maintain the selectivity of variant detection.

Example 2

This example provides empirical data obtained from actual biological samples to illustrate that the method using prioritized bins as disclosed above can increase signal levels for detecting a variant of interest.

Figure 8:
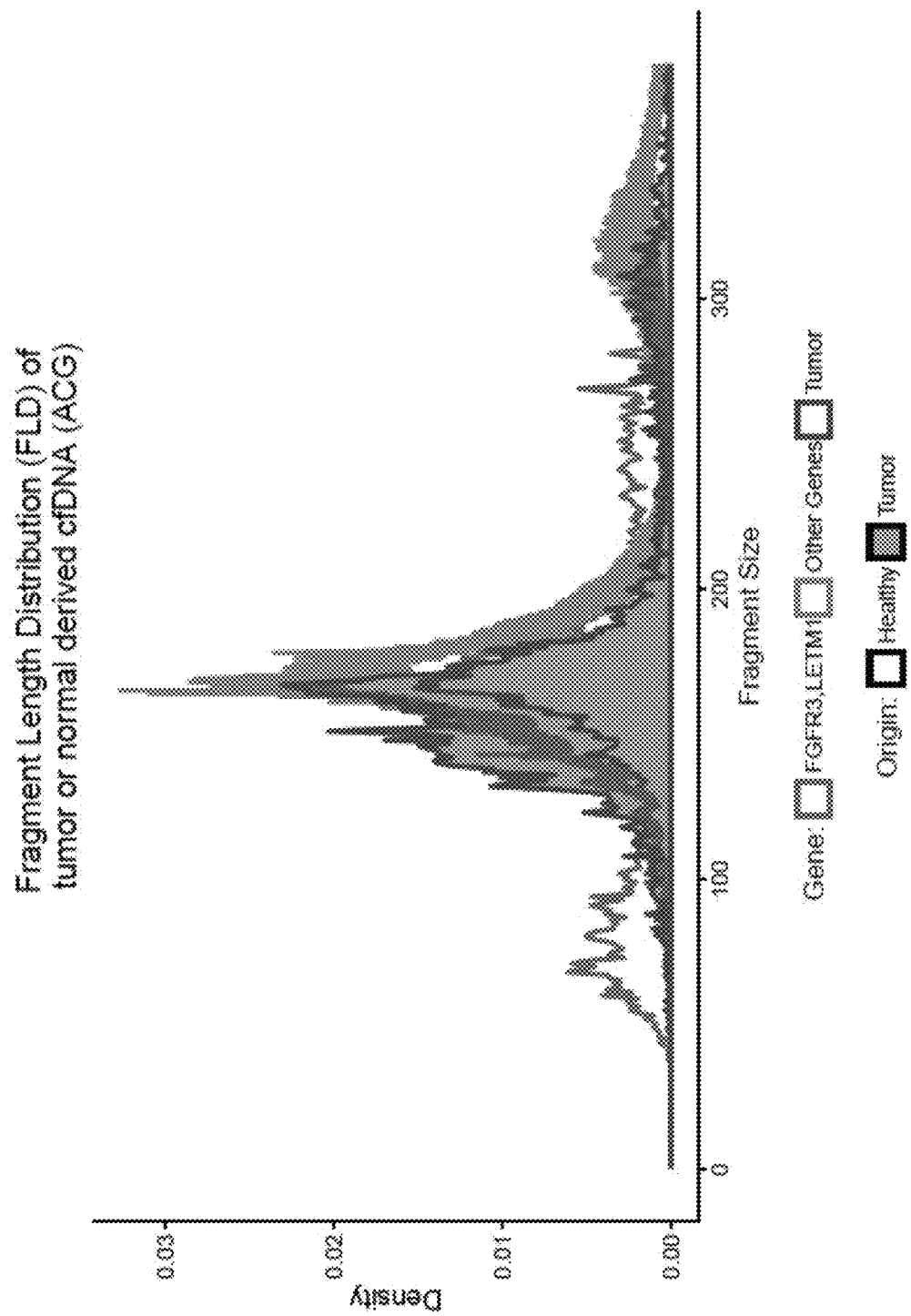
FIG. 8 shows fragment length distributions of cfDNA derived from tumor cells and from normal cells.

FIG. 8 shows fragment length distributions of cfDNA derived from tumor cells and from normal cells. A distribution of tumor cell derived cfDNA is shown by dark-gray lines. A distribution of normal cell derived cfDNA including genes FGFR3 and LETM1 is shown by mid-gray lines. A distribution of normal cell derived cfDNA containing other genes is shown by light-gray lines. The tumor derived cfDNA fragment distribution is also filled in with a gray shade. It is apparent from the three distributions in FIG. 8 that tumor derived cfDNA distribution has a main peak that is shifted towards the lower end.

FIG. 9 shows frequencies of cfDNA fragments assigned to bins having a bin size of 5 nt for tumor derived cfDNA and normal derived cfDNA. Tumor derived cfDNA frequencies are shown in dark gray bars, while normal cfDNA data are shown by a light gray bars. The two distributions are bimodal. The cancer derived distribution has a major peak at about 150 to 175 bp and a minor peak at about 315 bp. The distribution of normal cells has a major peak at 170 bp and a minor peak at about 320. The data in FIG. 9 also indicates that tumor derived cfDNA fragments can be shorter than normal cfDNA fragments.

Table 3 shows the fold change values of tumor allele quantity for the three types of bin sets, the fold change being relative to tumor allele quantities obtained using all bins. They are shown for 32 true positive mutations including simple nucleotide variants (SNV). The true positive mutations were known from an empirical study. Using the prioritized bins including mutant fragments, fold change values are larger than 1 in 31 of the 32 mutations. The fold change values obtained using all of the prioritized bins (including both bins containing mutant fragments and bins that do not contain mutant fragments) are larger than 1 in 28 out of 32 mutations. For a method using bins containing fragments shorter than 150 bp, 30 out of 32 true mutations can be detected with a fold change level larger than one. The bottom row of Table 3 shows that no mutations have a signal below the limit of detection. As such, data in Table 3 shows that using prioritized bins can boost signal level for detecting 32 true positive mutations in the biological samples.

Figure 10:
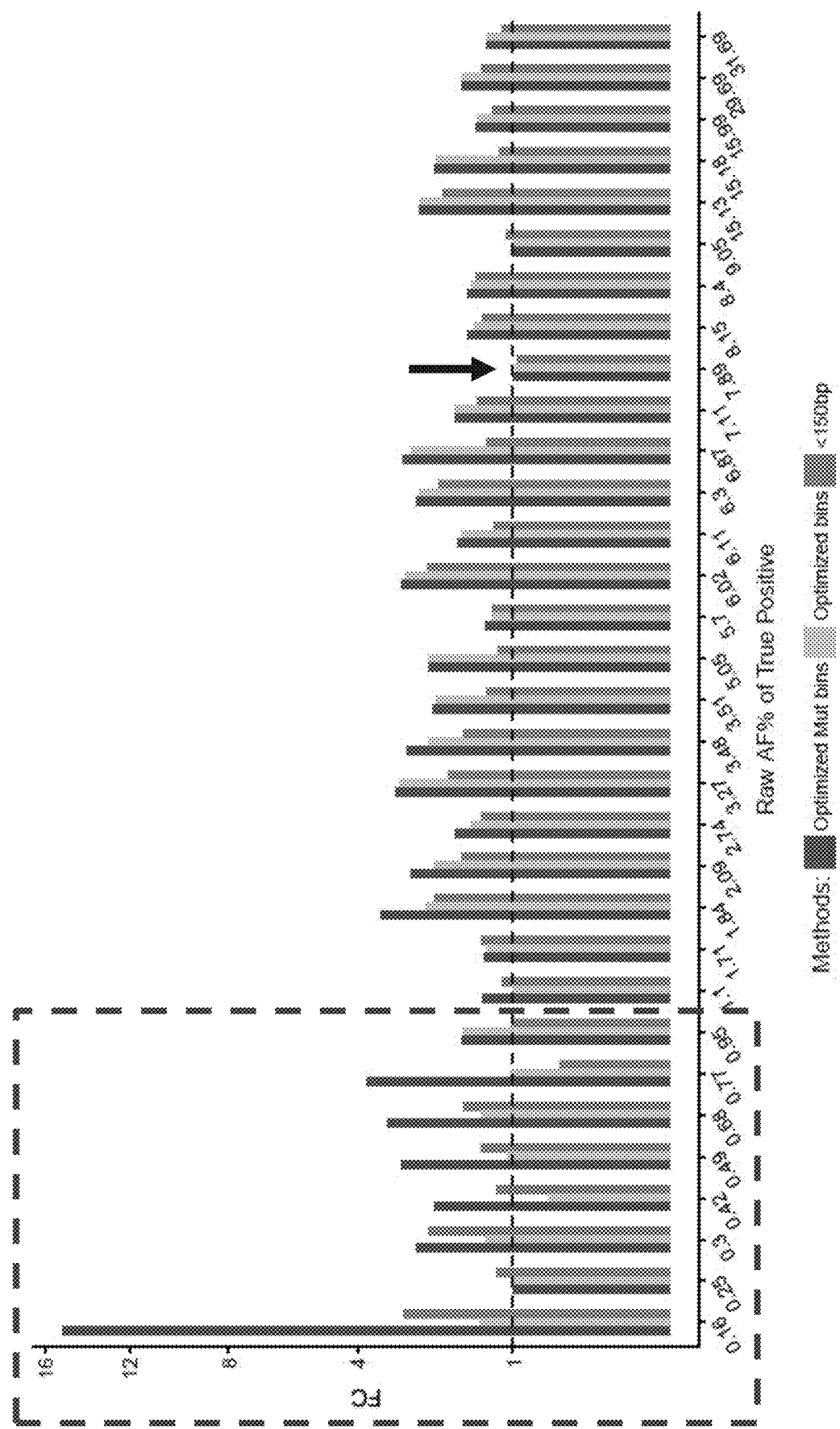
FIG. 10 shows fold change data for groups having different levels of raw allele frequencies for 32 true positive mutations.

FIG. 10 shows the fold change data broken down into groups having different levels of raw allele frequencies for the 32 true positive mutations. The horizontal axis of FIG. 10 indicates raw allele frequencies of the mutants for the biological samples. The Y axis of FIG. 10 indicates fold change. The dark-gray bars show fold change values obtained using the prioritized bins containing mutants. The light gray-gray bars show fold change values obtained using the prioritized bins. The mid-gray bars show data obtained using bins containing fragments shorter than 150 bp. The data in FIG. 10 indicates that methods using prioritized bins fold change values higher than 1, except for when the raw allele frequency is 7.89% as indicated by the arrow in the figure.

Furthermore, the fold change values appear larger when mutants have lower allele frequencies, such as when allele frequencies are lower than 1 as accentuated by a dashed box on the left of the figure.

Using prioritized bin sets can help to detect mutants that have allele frequencies lower than the limit of detection of 0.05%. Table 4 shows allele frequencies for five mutants in five rows, which have allele frequencies below the limit of detection when all bins are used to analyze the data (see the second column from the left). Using the prioritized bins containing the mutants of interest, the allele frequencies of mutants MDA_10134A:KRAS, MDA10070A:KRAS, and MSK080:KRAS were boosted to be above the limit of detection (see the third column from the left). Similar results were obtained for a method using all bins in the prioritized bin set (see the fourth column from the left). In contrast, the method using bins containing fragments shorter than 150 bp did not rescue any of the five mutations that fell under the limit of detection (see the fifth column from the lest). As such, data in Table 4 shows that using prioritized bins to analyze cfDNA fragments can help to detect of tumor variants having allele frequencies below limit of detection, effectively rescuing mutation detections that would have been otherwise missed.

What is claimed is:

1. A method, implemented on a computer system comprising one or more processors and system memory, of analyzing cell-free DNA (cfDNA) to determine a variant of interest, the method comprising:
   (a) retrieving, by the one or more processors, sequence reads and fragment sizes of cfDNA fragments obtained from a test sample;
   (b) assigning, by the one or more processors, the cfDNA fragments into a plurality of bins representing different fragment sizes; and
   (c) determining, using the sequence reads and by the one or more processors, an allele frequency of the variant of interest in a prioritized set of bins selected from the plurality of bins, wherein the prioritized set of bins was selected to (i) limit a probability that a quantity of the variant of interest in the prioritized set of bins is below a limit of detection and (ii) increase a probability that a quantity of the variant of interest in the prioritized set of bins is higher than in all bins of the plurality of bins, and wherein the prioritized set of bins was selected by a process comprising:
      providing a plurality of candidate sets, each candidate set including non-identical bins from the plurality of bins;
      for each candidate set, calculating a first probability that an allele frequency of the variant of interest in bins of the candidate set in a modeled sample is below a limit of detection, wherein the modeled sample includes both cfDNA originating from cells harboring the variant of interest and cfDNA originating from cells not harboring the variant of interest;
      for each candidate set, calculating a second probability that the allele frequency of the variant of interest in the bins of the candidate set in the modeled sample is above an allele frequency of the variant of interest in the plurality of bins in the modeled sample; and
      selecting a candidate set as the prioritized set based on the first probability and the second probability.

2. The method of claim 1, wherein the test sample is a plasma sample.

3. The method of claim 1, wherein the variant of interest is known or suspected to be associated with a cancer.

4. The method of claim 1, wherein the variant of interest is known or suspected to be associated with a genetic disorder.

5. The method of claim 1, further comprising comparing the allele frequency of the variant of interest in the prioritized set of bins to a criterion, and making, based on the comparing, a call of the variant of interest in the test sample.

6. The method of claim 1, wherein the prioritized set has a largest value of the second probability among candidate sets whose values of the first probability do not exceed a criterion.

7. The method of claim 1, wherein the plurality of candidate sets was obtained by a greedy process.

8. The method of claim 7, wherein the greedy process comprises:
   obtaining sequence reads and fragment sizes of cfDNA fragments obtained from one or more unaffected training samples known to not be affected by a condition of interest and one or more affected training samples known to be affected by the condition of interest;

assigning the cfDNA fragments obtained from the one or more unaffected training samples based on their sizes into the plurality of bins;

assigning the cfDNA fragments obtained from the one or more affected training samples based on their sizes into the plurality of bins;

ranking each bin of the plurality of bins based on a ratio of a frequency of fragments of the one or more affected training samples over a frequency of fragments of the one or more unaffected training samples;

selecting a bin having the highest rank as a candidate set;

adding a bin having a next highest rank to the last candidate set to provide a next candidate set; and repeating the last step until all bins of the plurality of bins are added, each repetition providing a candidate set.

9. The method of claim 8, wherein the condition of interest comprises one or more cancers.

10. The method of claim 9, wherein the condition of interest comprises a cancer associated with the variant of interest.

11. The method of claim 9, wherein the affected training samples comprise cancer tissues and the unaffected training samples comprise non-cancer tissues.

12. The method of claim 1, wherein the allele frequency of the variant of interest in the bins of the candidate set in the modeled sample is estimated as:

$$AF(L_{b1,b2\ldots bk}) = \frac{N_{mut}(L_{b1,b2\ldots bk})}{DP * [f_{tumor} * \Sigma_{b1}^{bk}\alpha(L_{bi}) + (1 - f_{tumor}) * \Sigma_{b1}^{bk}\beta(L_{bi})]}$$

wherein $AF(L_{b1, b2 \ldots bk})$ is an allele frequency for bins $L_{b1}$, $L_{b2} \ldots L_{bk}$, $N_{mut}(L_{b1, b2 \ldots bk})$ is a count of the variant of interest in bins $L_{b1}, L_{b2} \ldots L_{bk}$, DP is a sequencing depth, $f_{tumor}$ is a fraction of cfDNA from cells harboring the variant of interest, $\alpha(L_{bi})$ is a density of fragments in bin $L_{bi}$ in a fragment length distribution of one or more affected samples known to be affected by a condition of interest, and $\beta(L_{bi})$ is a density of fragments in bin $L_{bi}$ in a fragment length distribution of one or more unaffected samples known not to be affected by a condition of interest.

13. The method of claim 12, wherein the cells harboring the variant of interest are cancer cells, and the modeled sample comprises a plasma sample including cfDNA from cancer cells and cfDNA from non-cancer cells.

14. The method of claim 12, wherein the count of the variant of interest in bins $L_{b1}, L_{b2} \ldots L_{bk}$ is modeled as a binomial distribution:

$$N_{mut}(L_{b1,b2 \ldots bk}) \sim \text{Binomial}(\Sigma_{b1}^{bk}DP*f_{tumor}*\alpha(L_{bi}), AF_{tumor})$$

wherein $AF_{tumor}$ is the allele frequency of the variant of interest in the tissues harboring the variant of interest.

15. The method of claim 14, wherein $AF_{tumor}$ is calculated as:

$$AF_{tumor} = AF_{plasma}/f_{tumor}$$

wherein $AF_{plasma}$ is the allele frequency of the variant of interest in the modeled sample.

16. The method of claim 1, further comprises, after selecting the candidate set as the prioritized set, removing one or more bins that do not include a variant sequence of interest from the prioritized set.

17. The method of claim 1, wherein the limit of detection is about 0.05%-0.2%.

18. The method of claim 1, wherein the variant of interest comprises a simple nucleotide variant (SNV).

19. The method of claim 18, wherein the SNV is a single nucleotide variant, a phased sequential variant, or a small indel.

20. The method of claim 1, wherein the sequence reads are paired end reads, and the sizes of the cfDNA fragments are derived from read pairs.

21. The method of claim 1, wherein the cfDNA fragments obtained from the sample have been enriched.

22. The method of claim 1, further comprising, before (a), extracting the cfDNA fragments from the test sample.

23. The method of claim 1, wherein the cfDNA fragments comprise circulating tumor DNA (ctDNA) fragments.

24. A method of analyzing cell-free DNA (cfDNA) to determine a variant of interest, the method comprising:

(a) obtaining sequence reads and fragment sizes of cfDNA fragments obtained from a test sample;

(b) assigning the cfDNA fragments based on their sizes into a plurality of bins representing different fragment sizes; and (c) determining, using the sequence reads, an allele frequency of the variant of interest in a prioritized set of bins selected from the plurality of bins, wherein the prioritized set of bins are selected by a process comprising:

(i) providing a plurality of candidate sets, each candidate set including non-identical bins from the plurality of bins;

(ii) for each candidate set, calculating a second probability that an allele frequency of the variant of interest in bins of the candidate set in a modeled sample is above an allele frequency of the variant of interest in the plurality of bins in the modeled sample, wherein the modeled sample includes both tissues harboring the variant of interest and tissues harboring a wildtype sequence of the variant of interest; and (iii) selecting a candidate set having a largest value of the second probability.

25. The method of claim 24, further comprising, before (iii) and for each candidate set, calculating a first probability that the allele frequency of the variant of interest in the bins of the candidate set in the modeled sample does not exceed a limit of detection, wherein (iii) comprises selecting a candidate set having a largest value of the second probability among candidate sets whose values of the first probability do not exceed a criterion.

26. The method of claim 24, wherein the test sample is a plasma sample.

27. The method of claim 24, wherein the variant of interest is known or suspected to be associated with a cancer.

28. The method of claim 24, wherein the variant of interest is known or suspected to be associated with a genetic disorder.

29. The method of claim 24, further comprising comparing the allele frequency of the variant of interest in the prioritized set of bins to a criterion, and making, based on the comparing, a call of the variant of interest in the test sample.

30. The method of claim 24, wherein the variant of interest comprises a simple nucleotide variant (SNV).

31. The method of claim 30, wherein the SNV is a single nucleotide variant, a phased sequential variant, or a small indel.

32. The method of claim 24, wherein the cfDNA fragments comprise circulating tumor DNA (ctDNA) fragments.

33. A system for analyzing cell-free DNA (cfDNA), the system comprising: a sequencer for receiving a nucleic acid sample and providing nucleic acid sequence information from the nucleic acid sample; and one or more processors configured to:
(a) retrieve sequence reads and fragment sizes of cfDNA fragments obtained from a test sample;
(b) assign the cfDNA fragments into a plurality of bins representing different fragment sizes; and
(c) determine, using the sequence reads, an allele frequency of the variant of interest in a prioritized set of bins selected from the plurality of bins, wherein the prioritized set of bins was selected to (i) limit a probability that a quantity of the variant of interest in the prioritized set of bins is below a limit of detection and (ii) increase a probability that a quantity of the variant of interest in the prioritized set of bins is higher than in all bins of the plurality of bins, and wherein the prioritized set of bins was selected by a process comprising:
providing a plurality of candidate sets, each candidate set including non-identical bins from the plurality of bins;
for each candidate set, calculating a first probability that an allele frequency of the variant of interest in bins of the candidate set in a modeled sample is below a limit of detection, wherein the modeled sample includes both cfDNA originating from cells harboring the variant of interest and cfDNA originating from cells not harboring the variant of interest;
for each candidate set, calculating a second probability that the allele frequency of the variant of interest in the bins of the candidate set in the modeled sample is above an allele frequency of the variant of interest in the plurality of bins in the modeled sample; and
selecting a candidate set as the prioritized set based on the first probability and the second probability.

34. A computer program product comprising a non-transitory machine readable medium storing program code that, when executed by one or more processors of a computer system, causes the computer system to implement a method for determining a variant of interest in cell-free DNA, said program code comprising:
(a) code for retrieving sequence reads and fragment sizes of cfDNA fragments obtained from a test sample;
(b) code for assigning the cfDNA fragments into a plurality of bins representing different fragment sizes; and
(c) code for determining, using the sequence reads, an allele frequency of the variant of interest in a prioritized set of bins selected from the plurality of bins, wherein the prioritized set of bins was selected to (i) limit a probability that a quantity of the variant of interest in the prioritized set of bins is below a limit of detection and (ii) increase a probability that a quantity of the variant of interest in the prioritized set of bins is higher than in all bins of the plurality of bins, and wherein the prioritized set of bins was selected by a process comprising:
providing a plurality of candidate sets, each candidate set including non-identical bins from the plurality of bins;
for each candidate set, calculating a first probability that an allele frequency of the variant of interest in bins of the candidate set in a modeled sample is below a limit of detection, wherein the modeled sample includes both cfDNA originating from cells harboring the variant of interest and cfDNA originating from cells not harboring the variant of interest;
for each candidate set, calculating a second probability that the allele frequency of the variant of interest in the bins of the candidate set in the modeled sample is above an allele frequency of the variant of interest in the plurality of bins in the modeled sample; and
selecting a candidate set as the prioritized set based on the first probability and the second probability.

* * * * *

UNITED STATES PATENT AND TRADEMARK OFFICE
CERTIFICATE OF CORRECTION

PATENT NO. : 11,342,047 B2
APPLICATION NO. : 15/957622
DATED : May 24, 2022
INVENTOR(S) : Tingting Jiang, Chen Zhao and Han-Yu Chuang It is certified that error appears in the above-identified patent and that said Letters Patent is hereby corrected as shown below:

In the Claims

In Line 41 of Claim 12 (Column 49, Line 41) change "α (Lbi)" to -- α(Lbi) --.

Signed and Sealed this
Twenty-fifth Day of October, 2022

Katherine Kelly Vidal
*Director of the United States Patent and Trademark Office*